(12) United States Patent
Wang et al.

(10) Patent No.: US 12,415,051 B2
(45) Date of Patent: Sep. 16, 2025

(54) OXYGEN CONCENTRATOR

(71) Applicant: Roam Technologies Pty Ltd., Carlton (AU)

(72) Inventors: Shan-Shan Wang, Sydney (AU); Eugene Weng Hong Lai, Sydney (AU); Sisi Zheng, Sydney (AU); Jay Reginald Flack, Sydney (AU); Jeremy Travis Kwarcinski, Sydney (AU); Natalie Etain Ho, Sydney (AU); Gavin Dean May, Sydney (AU)

(73) Assignee: Roam Technologies Pty Ltd., Carlton (AU)

( * ) Notice: Subject to any disclaimer, the term of this patent is extended or adjusted under 35 U.S.C. 154(b) by 0 days.

(21) Appl. No.: 18/827,432

(22) Filed: Sep. 6, 2024

(65) Prior Publication Data

US 2025/0082886 A1   Mar. 13, 2025

Related U.S. Application Data

(60) Provisional application No. 63/581,102, filed on Sep. 7, 2023.

(51) Int. Cl.
  *B01D 53/02* (2006.01)
  *A61M 16/00* (2006.01)
  (Continued)

(52) U.S. Cl.
  CPC ........ *A61M 16/101* (2014.02); *A61M 16/024* (2017.08); *A61M 16/208* (2013.01);
  (Continued)

(58) Field of Classification Search
  CPC .............. A61M 16/101; A61M 16/024; A61M 16/208; A61M 2016/0027;
  (Continued)

(56) References Cited

U.S. PATENT DOCUMENTS

| 4,144,037 A | 3/1979 | Armond et al. |
| 4,422,456 A | 12/1983 | Tiep |

(Continued)

FOREIGN PATENT DOCUMENTS

| CA | 2627888 | 8/2011 |
| CA | 2656692 | 4/2013 |

(Continued)

OTHER PUBLICATIONS

International Search Report and Written Opinion mailed Jan. 9, 2025, from corresponding PCT Application No. PCT/IB2024/058723, filed Sep. 7, 2024 (12 pages).

(Continued)

*Primary Examiner* — Christopher P Jones
(74) *Attorney, Agent, or Firm* — Finnegan, Henderson, Farabow, Garrett & Dunner LLP

(57) ABSTRACT

A handheld portable oxygen concentrator device is disclosed. The device may comprise a first column and a second column, a product buffer, a plurality of valves in fluidly coupling the first column, the second column, the one or more pumps, and the product buffer. The device may comprise a controller configured to cycle repeatedly through the following phases: (a) raising pressure in the first column by connecting the first column to a positive pressure pump and releasing concentrated oxygen in the first column to the product buffer, (b) equalizing the pressure in the first column and the second column by connecting the first column to the second column, (c) lowering the pressure in the first column by connecting the first column to a negative pressure pump, and (d) equalizing the pressure in the first column and the second column by connecting the first column to the second column.

27 Claims, 24 Drawing Sheets

(51) Int. Cl.
*A61M 16/10* (2006.01)
*A61M 16/20* (2006.01)

(52) U.S. Cl.
CPC ............... *A61M 2016/0027* (2013.01); *A61M 2016/0033* (2013.01); *A61M 2205/3331* (2013.01); *A61M 2205/502* (2013.01)

(58) Field of Classification Search
CPC .. A61M 2016/0033; A61M 2205/3331; A61M 2205/502
See application file for complete search history.

(56) References Cited

U.S. PATENT DOCUMENTS

| | | |
|---|---|---|
| 4,535,767 A | 8/1985 | Tiep et al. |
| 4,572,177 A | 2/1986 | Tiep et al. |
| 4,859,217 A | 8/1989 | Chao |
| 5,156,657 A | 10/1992 | Jain et al. |
| 5,280,780 A | 1/1994 | Abel |
| 5,330,561 A | 7/1994 | Kumar et al. |
| 5,429,666 A | 7/1995 | Agrawal et al. |
| 5,531,808 A | 7/1996 | Ojo et al. |
| 5,656,068 A | 8/1997 | Smolarek et al. |
| 5,702,504 A | 12/1997 | Schaub et al. |
| 5,871,565 A | 2/1999 | Leavitt |
| 6,261,345 B1 | 7/2001 | Miyano et al. |
| 6,471,744 B1 | 10/2002 | Hill |
| 6,551,384 B1 | 4/2003 | Ackley et al. |
| 6,641,645 B1 | 11/2003 | Lee et al. |
| 6,709,486 B2 | 3/2004 | Lee et al. |
| 6,712,886 B2 | 3/2004 | Kim |
| 6,878,186 B2 | 4/2005 | Neary |
| 6,949,133 B2 | 9/2005 | McCombs et al. |
| 7,037,358 B2 | 5/2006 | Babicki et al. |
| 7,121,276 B2 | 10/2006 | Jagger et al. |
| 7,328,703 B1 | 2/2008 | Tiep |
| 7,438,745 B2 | 10/2008 | Deane et al. |
| 7,510,601 B2 | 3/2009 | Whitley et al. |
| 7,682,428 B2 | 3/2010 | Nawata et al. |
| 7,753,996 B1 | 7/2010 | Deane et al. |
| 7,875,105 B2 | 1/2011 | Chambers et al. |
| 8,016,925 B2 | 9/2011 | McCombs et al. |
| 8,020,553 B2 | 9/2011 | Jagger et al. |
| 8,177,886 B2 | 5/2012 | Draper et al. |
| 8,337,599 B2 | 12/2012 | Kiritake |
| 8,366,815 B2 | 2/2013 | Taylor et al. |
| 8,677,998 B2 | 3/2014 | Yamaura et al. |
| 8,702,841 B2 | 4/2014 | Taylor et al. |
| 8,808,426 B2 | 8/2014 | Sundaram |
| 8,894,751 B2 | 11/2014 | Galbraith et al. |
| 8,915,248 B2 | 12/2014 | Wilkinson et al. |
| 9,095,811 B2 | 8/2015 | Dolensky |
| 9,120,050 B2 | 9/2015 | Richey, II et al. |
| 9,132,377 B2 | 9/2015 | Richey, II et al. |
| 9,220,864 B2 | 12/2015 | Taylor et al. |
| 9,283,343 B2 | 3/2016 | Pizzini |
| 9,440,180 B2 | 9/2016 | Wilkinson et al. |
| 9,468,732 B2 | 10/2016 | Tiep et al. |
| 9,486,600 B2 | 11/2016 | Martin |
| 9,566,407 B2 | 2/2017 | Martin |
| 9,592,360 B2 | 3/2017 | Taylor et al. |
| 9,624,918 B2 | 4/2017 | Goertzen et al. |
| 9,630,895 B2 | 4/2017 | Sturm et al. |
| 9,717,876 B2 | 8/2017 | Wilkinson et al. |
| 9,776,129 B2 | 10/2017 | Heirman |
| 9,782,557 B2 | 10/2017 | Wilkinson et al. |
| 9,956,370 B2 | 5/2018 | Wilkinson et al. |
| 9,974,920 B2 | 5/2018 | Schneider et al. |
| 10,010,696 B2 | 7/2018 | Sprinkle et al. |
| 10,046,134 B2* | 8/2018 | DeVries ............ A61M 16/0883 |
| 10,255,647 B2 | 4/2019 | Rodman et al. |
| 10,300,427 B2 | 5/2019 | Richey et al. |
| 10,335,570 B2 | 7/2019 | Van Brunt et al. |
| 10,357,628 B2 | 7/2019 | Jagger et al. |
| 10,449,479 B2 | 10/2019 | Sundaram et al. |
| 10,561,863 B1 | 2/2020 | Dashevsky et al. |
| 10,583,265 B2 | 3/2020 | Whitcher et al. |
| 10,610,658 B2 | 4/2020 | Tiep et al. |
| 10,695,520 B2 | 6/2020 | Taylor et al. |
| 10,702,669 B2 | 7/2020 | Jagger et al. |
| 10,786,644 B2 | 9/2020 | Taylor et al. |
| 10,953,187 B2 | 3/2021 | Galbraith et al. |
| 11,052,213 B2 | 7/2021 | Romano |
| 11,278,697 B2 | 3/2022 | Galbraith et al. |
| 11,369,768 B2 | 6/2022 | Galbraith et al. |
| 11,389,614 B2 | 7/2022 | Jagger et al. |
| 11,491,438 B2 | 11/2022 | Körber et al. |
| 11,607,519 B2 | 3/2023 | Westfall et al. |
| 11,648,505 B2 | 5/2023 | Lei |
| 11,911,566 B2 | 2/2024 | Zapol et al. |
| 12,005,194 B2 | 6/2024 | Galbraith et al. |
| 2002/0096174 A1 | 7/2002 | Hill et al. |
| 2008/0006151 A1 | 1/2008 | Baksh et al. |
| 2008/0148938 A1* | 6/2008 | Rege .................... B01D 53/047 96/121 |
| 2010/0095841 A1 | 4/2010 | Naheiri |
| 2010/0300285 A1 | 12/2010 | Siew-Wah et al. |
| 2011/0017063 A1* | 1/2011 | Van Brunt ............ A61M 16/20 95/101 |
| 2016/0279372 A1* | 9/2016 | DeVries ............ A61M 16/207 |
| 2017/0340851 A1* | 11/2017 | Allum ............... A61M 16/0672 |
| 2018/0093219 A1 | 4/2018 | Monereau et al. |
| 2018/0228997 A1 | 8/2018 | Krentler et al. |
| 2020/0024065 A1 | 1/2020 | Barratt et al. |
| 2020/0164170 A1 | 5/2020 | Huttner et al. |
| 2020/0368667 A1 | 11/2020 | Obata et al. |
| 2021/0113801 A1* | 4/2021 | Wang ................. A61M 16/1015 |
| 2021/0260329 A1 | 8/2021 | Koerber et al. |
| 2021/0289854 A1* | 9/2021 | Popa-Simil .......... A62B 17/006 |
| 2022/0241540 A1* | 8/2022 | Wang ........................ B01J 20/18 |
| 2022/0313932 A1 | 10/2022 | Ahmad |
| 2022/0379066 A1 | 12/2022 | Navarro et al. |
| 2022/0379067 A1 | 12/2022 | Varga |
| 2023/0012016 A1 | 1/2023 | Miaralipour et al. |
| 2023/0045644 A1 | 2/2023 | Poon et al. |
| 2023/0104813 A1 | 4/2023 | Poon et al. |
| 2023/0120744 A1 | 4/2023 | Taylor et al. |
| 2023/0256185 A1 | 8/2023 | Chang |
| 2024/0123176 A1 | 4/2024 | Jagger et al. |

FOREIGN PATENT DOCUMENTS

| | | |
|---|---|---|
| CN | 206624639 U | 11/2017 |
| CN | 114956005 A | 8/2022 |
| CN | 115043380 A | 9/2022 |
| JP | 2005021297 | 1/2005 |
| JP | 2006205079 A | 8/2006 |
| WO | WO 2007/053494 A1 | 5/2007 |
| WO | WO 2008/005492 A1 | 1/2008 |
| WO | WO 2019/002075 A1 | 1/2019 |
| WO | WO 2022/023978 A1 | 2/2022 |
| WO | WO 2022/099350 A1 | 5/2022 |
| WO | WO 2022/167985 A1 | 8/2022 |

OTHER PUBLICATIONS

Ackley, Mark W., "Medical oxygen concentrators: a review of progress in air separation technology", Adsorption (2019) 25:1437-1474.

Chai, S.W. et al., "Rapid Pressure Swing Adsorption for Reduction of Bed Size Factor of a Medical Oxygen Concentrator", American Chemical Society, *Ind. Eng. Chem. Res.* (2011) 50:8703-8710.

Moran, A. et al., "Role of Pressure Drop on Rapid Pressure Swing Adsorption Performance", American Chemical Society, *Ind. Eng. Chem. Res.* (2017) 56:5715-5723.

Pan, M. et al., "Application of Nanosize Zeolite Molecular Sieves for Medical Oxygen Concentration", Nanomaterials (2017) 7, 195, 19 pages.

Rao, V.R. et al. "Design of a Two-Step Pulsed Pressure-Swing Adsorption-Based Oxygen Concentrator", American Institute of

(56) References Cited

OTHER PUBLICATIONS

Chemical Engineers, *AIChE Journal*, Feb. 2010, vol. 56, No. 2, pp. 354-370.

Rao, V.R. et al., "Experimental Study of a Pulsed-Pressure-Swing-Adsorption Process with Very Small 5A Zeolite Particles for Oxygen Enrichment", American Chemical Society, *Ind. Eng. Chem. Res.* (2014) 53:13157-13170.

Rao, V.R. et al., "Numerical simulation of rapid pressurization and depressurization of a zeolite col. using nitrogen", *Adsorption*, (2014) 20:53-60.

Santos, J.C. et al., "Optimization of Medical PSA Units for Oxygen Production", American Chemical Society, *Ind. Eng. Chem. Res.* (2006) 45:1085-1096.

Shin, H. et al., "Performance of a Two-Bed Pressure Swing Adsorption Process with Incomplete Pressure Equalization", *Adsorption*, (2000) 6:233-240.

Zhu, X. et al., "Effects of operating temperature on the performance of small scale rapid cycle pressure swing adsorption air separation process", *Adsorption*, (2021) 27:205-212.

Zhu, X. et al., "Study of a novel rapid vacuum pressure swing adsorption process with intermediate gas pressurization for producing oxygen", *Adsorption*, (2017) 23:175-184.

Lee, S. et al., "Parametric Study of the Three-Bed Pressure-Vacuum Swing Adsorption Process for High Purity 02 Generation from Ambient Air", Ind. Eng. Chem. Res., (2007) vols. 46: 3720-3728.

\* cited by examiner

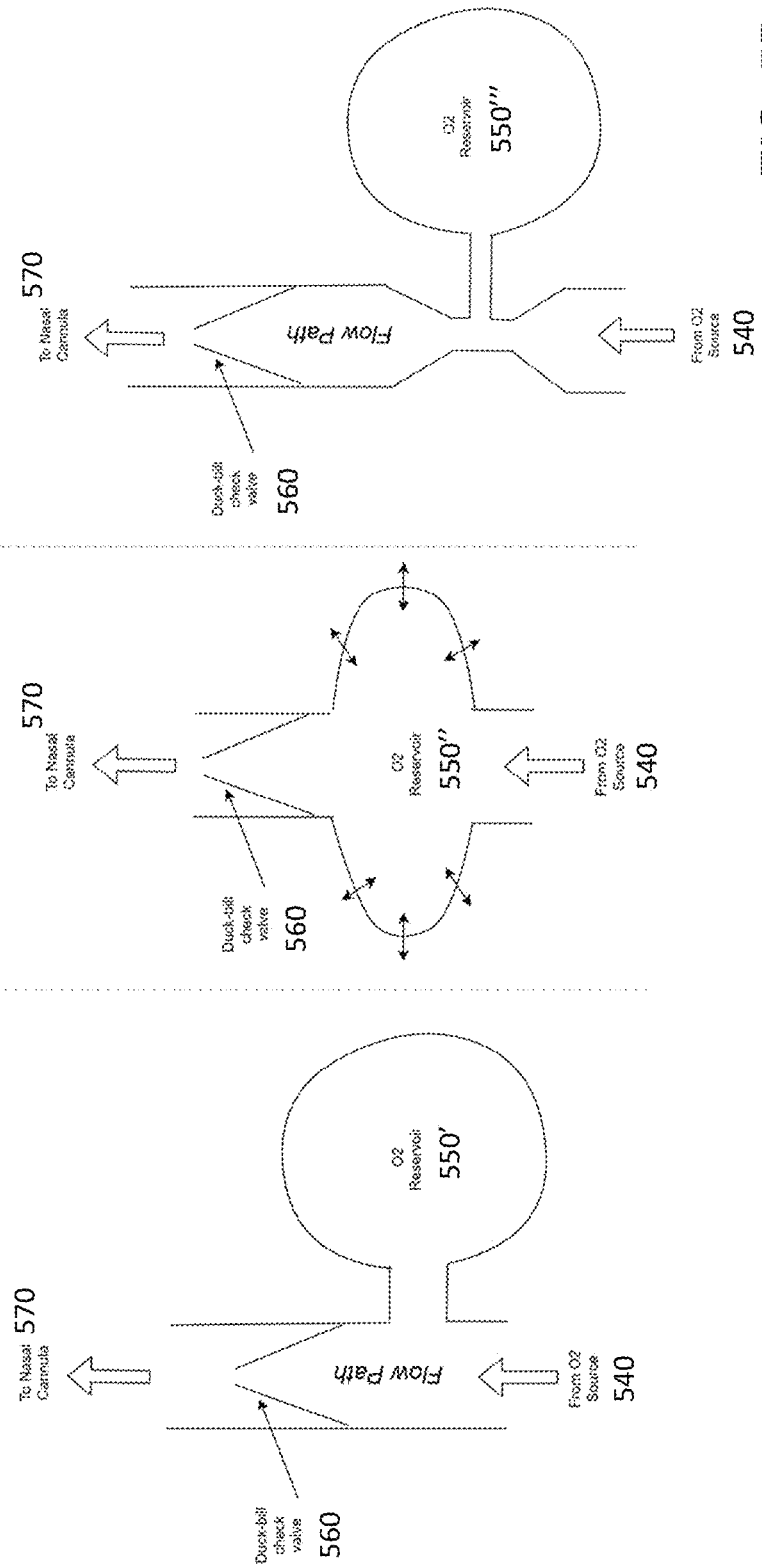

OXYGEN CONCENTRATOR

This application claims priority under 35 U.S.C. § 119 (e) to U.S. Provisional Application No. 63/518,102 63/581,102, filed Sep. 7, 2023, the contents of which are incorporated herein by reference in their entirety.

TECHNICAL FIELD

The disclosed systems and methods concern gas concentrators. In particular, the disclosed systems and methods concern handheld and portable oxygen concentrators using a pressure swing absorption process.

BACKGROUND

Oxygen ($O_2$) supplementation is a vital therapeutic intervention used to manage a variety of medical conditions, including chronic obstructive pulmonary disease (COPD), heart disease, emphysema, fibrotic lung disease, pulmonary hypertension, cluster headache, migraine and asthma. It is also employed in veterinary medicine to support animals with respiratory and cardiac conditions, as well as during surgeries and recovery. Additionally, oxygen supplementation plays a role in wound care, accelerating healing, and improving the health and appearance of the outer epidermis. It is also commonly used in recreational settings, including to alleviate symptoms associated with altitude sickness and to augment physical performance. Ambulatory oxygen supplementation is necessary in hospital, home, outdoor, and portable settings due to its extensive use.

Oxygen supplementation is typically delivered via high-pressure gas cylinders, liquid oxygen or medical oxygen concentrators also known as stationary oxygen concentrators. A portable oxygen concentrator is the portable version of a medical oxygen concentrator, and it has many advantages that make it increasingly favored over gas cylinders or liquid oxygen.

SUMMARY

The disclosed systems and methods relate to a portable oxygen concentrator. In some embodiment, the portable oxygen concentrator may be a handheld device. In some embodiments, the portable oxygen concentrator may include a first column and a second column, one or more pumps; a controller; a buffer; a reservoir; and a plurality of valves fluidly coupling the first column, the second column, and the one or more pumps. In some embodiments, the first column and the second column may include an adsorbent. In some embodiment, the controller may be configured to a) raising pressure in the first column by connecting the first column to a positive pressure pump and releasing concentrated oxygen in the first column to the product buffer, b) equalizing the pressure in the first column and the second column by connecting the first column to the second column, c) lowering the pressure in the first column by connecting the first column to a negative pressure pump, and d) equalizing the pressure in the first column and the second column by connecting the first column to the second column.

In some embodiments, a portable oxygen concentrator may comprise a first column and a second column and the first column and the second column include an adsorbent. The portable oxygen concentrator may further comprise one or more pumps, a plurality of valves fluidly coupling the first column, the second column, and the one or more pumps, and a removable module. The removable module may comprise a product buffer filled with adsorbent, an inflatable oxygen reservoir, and a duck-bill valve with cracking pressure that is configured to inflate the inflatable oxygen reservoir.

It is to be understood that both the foregoing general description and the following detailed description are exemplary and explanatory only and are not restrictive of the disclosed embodiments, as claimed.

BRIEF DESCRIPTION OF THE DRAWINGS

The drawings are not necessarily to scale or exhaustive. Instead, emphasis is generally placed upon illustrating the principles of the embodiments described herein. The accompanying drawings, which are incorporated in and constitute a part of this specification, illustrate several embodiments consistent with the disclosure and, together with the description, serve to explain the principles of the disclosure. In the drawings:

FIGS. 5B, 5C, and 5D depict three exemplary configurations utilizing balloon-like material as an oxygen reservoir within the removable module of the exemplary oxygen concentrator of FIG. 5A.

DETAILED DESCRIPTION

Figure 1:
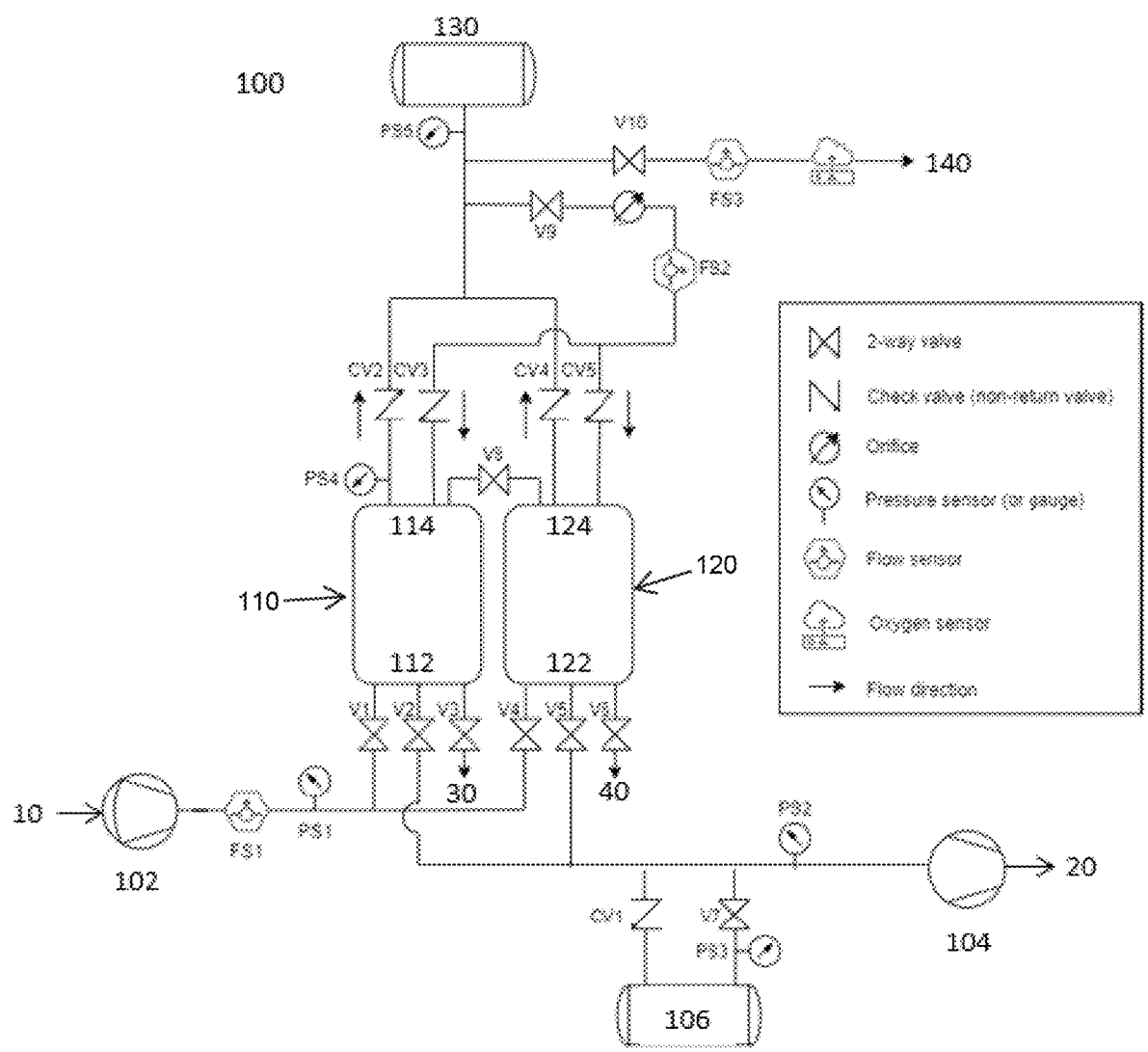
FIG. 1 depicts a schematic diagram of an exemplary oxygen concentrator according to some embodiments of the current disclosure.

Reference will now be made in detail to exemplary embodiments, discussed with regards to the accompanying drawings. In some instances, the same reference numbers will be used throughout the drawings and the following description to refer to the same or like parts. Unless otherwise defined, technical or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

It should be noted that all relative terms such as "about," "substantially," "approximately," etc., are used to indicate a possible variation of up to 15% (unless noted otherwise or another variation is specified). For example, a parameter (e.g., pressure, time, dimension, etc.) described and being substantially equal to, or about, "t" units covers a variation of up to 15%. Additionally, a described range (e.g., X-Y, X to Y, etc.) includes the two boundaries. That is, a parameter described as being between about X-Y units may have any value between X−15% to Y+15%. These small variations are intended to cover deviations that may occur, for example, during, fabrication, manufacture, and/or operation.

It should be noted that all following terms including "oxygen concentrated gas," "oxygen production," "oxygen product," "concentrated oxygen," "oxygenized air," "oxygen flow," "oxygen supply," "oxygen enriched gas," are used to indicate an oxygen product passed through adsorbent-filled column.

The disclosed system uses pressure swing adsorption (PSA), which means pressure swings from a relatively higher pressure that permits adsorption of a target gas into an adsorbent material, to a relatively lower pressure that permits desorption of the target gas from the adsorbent material. The disclosed system may include absolute pressure swing adsorption (APSA), which means the process pressure swings in between the adsorption pressure that is over-atmospheric (e.g., >1 bar) and the desorption pressure that is sub-atmospheric (e.g., <1 bar-under vacuum). In APSA, both pressures are described in an absolute manner (unit of bar absolute). In this document the terms "absolute pressure swing adsorption" (APSA) and "vacuum pressure swing adsorption" (VPSA) are used interchangeably.

High quality oxygen flow may be accomplished by PSA and absolute pressure swing adsorption APSA techniques. APSA and PSA are two different methods used for gas separation and purification processes. They both rely on the principle of adsorption to separate gases. One or more columns may contain an adsorbent like zeolite that are pressurised in turns by a pump, preferably adsorbing $N_2$ in the feed air and allowing oxygen to pass through as a product. At the end of a production cycle, the higher column pressure is released to the ambient or sub-atmospheric pressure, during which the adsorbed $N_2$ is also released. At the same time the column is purged using oxygen product from the other column as product, leaving a relatively clean batch of zeolite ready to start the next cycle.

APSA System

APSA technology incorporates a vacuum pump to increase the pressure swing range by utilizing sub-atmospheric pressure. It has several significant advantages over PSA technology, including: (1) the commonly used adsorbent in portable oxygen concentrator (LiX or LiLSX zeolite) has a steep $N_2$ isotherm curve at the sub-atmospheric pressure range, which means the working adsorption capacity is greater with the same pressure swing. APSA takes advantage of this steep segment of the isotherm curve, resulting in better efficiency of utilizing the adsorbent (lower bed-size factor). This leads to smaller columns and less cost spent on adsorbents. (2) APSA technology widens the pressure swing range by lowering the desorption pressure, rather than increasing the adsorption pressure as in the case of PSA technology. To obtain the same production, an APSA process requires a much lower adsorption pressure than that required by a PSA process. As a consequence, the pressure rating of all fluid componentry is significantly reduced, which means the device can be smaller and lighter. (3) The APSA technology doubles oxygen recovery of the process, meaning that the required feed air flowrate is only half of what is required by a PSA process. As a result, the adsorbent is exposed to less contaminant (mainly moisture and $CO_2$ in the ambient air) and would have a longer run time. (4) The lower feed required in APSA technology introduces a significantly lower pressure drop across the zeolite adsorbent columns. This means the pressure pump works with much lower back pressure and thus can deliver more feed at the same target adsorption pressure. (5) The APSA technology reduces zeolite column pressure to a sub-atmospheric level in each cycle. The desorption is more complete and therefore residual $N_2$ quantity is decreased. This process also better cleans the columns.

Conventionally, APSA systems have been applied in various industrial-scale adsorption processes. In the current disclosure, an APSA based system is used in portable oxygen concentrators. In some embodiments, the oxygen concentrators of the current disclosure may be portable devices. A portable device (or system) refers to a device that can be carried, moved, or transported from one place to another without significant difficulty. Portable devices can be carried by a person or transported from one place to another using relatively simple means (e.g., such as by hand, trolley, bag, vehicle, or another mechanism). A portable device is generally designed to be lightweight, compact, and convenient for mobility, allowing it to be used in various locations or situations as needed.

In some embodiments, the oxygen concentrators of the current disclosure may be a handheld device. A handheld device is a class of portable device that may be carried from place to place in a person's (user, clinician, technician, etc.) hand. A handheld device may be worn on person's belt, in a bag, backpack, tote or purse, hung from a strap that runs over a person's shoulder or back of neck without, or strapped to a person's arm or leg. In some embodiments, a handheld device may be worn on person's arm or leg by at least one of a silicone band, sports band, a sleeve band, and a spandex band. The band may keep the handheld oxygen concentrator in place. In some embodiments, such devices may be designed to be held and operated with one or both hands. These devices are typically compact and lightweight, making them easy to carry and use while on the move. While handheld devices are a subset of portable devices, not all portable devices are meant to be held in the hands and operated directly like handheld devices. Portable devices may have different user interfaces and interaction methods compared to handheld devices. In summary, one distinction between a handheld device and a portable device is in how they are intended to be used and interacted with. Handheld devices are specifically designed to be operated while held in the hands, whereas portable devices, while also designed for mobility, encompass a broader range of devices that can be transported, but may not necessarily require hand-held operation.

Oxygen concentrators that are small and light enough to be carried anywhere and that are easy to use, while still concentrating sufficient oxygen, are highly desired. To achieve sufficient oxygen output, current oxygen concentrators use a number of trade-offs that work to the detriment of the user or patient. To obtain sufficient oxygen output, current oxygen concentrators increase adsorption pressure by increasing the number of zeolites, by increasing the size of the pump, or by increasing the number of pumps. These result in increasing the power requirement of the device, which shortens runtime, and/or increasing the number of components, which increases cost to the user, and which result in heavier, larger, and bulkier oxygen concentration devices.

A handheld oxygen concentrator may be used to treat acute episodes of chronic headaches. Inhaled oxygen delivered through this portable device provides rapid relief during acute attacks of cluster headaches and migraines. Beyond headache management, supplemental oxygen delivered by a handheld oxygen concentrator can play a role in wound healing, ensuring that living tissue receives the oxygen necessary for regenerating healthy tissue and promoting faster recovery. Additionally, a handheld oxygen generator of the current disclosure can be used as part of first aid, offering immediate oxygen support in emergency situations to address a range of medical needs. Living tissue requires oxygen and nutrients to thrive, and for wounds, oxygen is essential for regenerating healthy tissue. In normal wound healing, the process alternates between conditions of hypoxia and normoxia, which are critical in all phases of healing. The supply of oxygen to the wound tissue, determined by pulmonary gas exchange and blood hemoglobin levels, plays an essential role in reconstructing new vessels and connective tissue, as well as in the migration of epithelial cells. Oxygen also facilitates normal local metabolism and enhances resistance to infection. A handheld oxygen generator of the current disclosure is particularly beneficial in these applications. It provides a portable and convenient means to deliver oxygen where it's needed most, whether for treating headaches or supporting wound healing. In the context of wound care, the handheld device may be employed for topical oxygen therapy (TOT), a set of techniques that deliver oxygen directly to wounds or ulcers, promoting tissue healing. A handheld oxygen concentrator of the current disclosure may be used to increase oxygen tension and support tissue regeneration. Rapid oxygen delivery has significant positive impacts on wound healing unlike hyperbaric oxygen, a handheld oxygen concentrator may be quickly applied to wound dressings, saturating the dressing with high-purity oxygen, or used to provide oxygen to a higher cyclical or low-constant-pressure bags, or bandages, ensuring continuous oxygen delivery to the wound site, and promote faster recovery and accelerated healing. Handheld oxygen generators of the current disclosure offer the ability to generate high purity oxygen flow more efficiently from ambient air, utilising the adsorption capacity of zeolite particles in a more compact and portable design, as well as the ability to operate continuously, allowing for a steady supply of purified gas without frequent interruptions or limitations on mobility and enhancing the effectiveness of oxygen therapy for managing acute headache episodes, particularly in portable and emergency settings. They may also be tailored for different gas compositions. Further portable and handheld applications include a remote or temporary gas supply, where a device could be deployed in remote locations or areas where access to a stable on-site gas supply is limited, eliminating the need for gas transportation and storage logistics. This could be particularly valuable for military forces during deployment in remote areas or active conflict zones, providing a self-sustained gas supply for various needs, replacing bulky oxygen cylinders and large oxygen production equipment for in field hospitals, during the evacuation of the wounded, on the road, and on the battlefield. A handheld device could be adapted for drone deployment or air-dropped in, ensuring rapid and flexible deployment to personnel in critical situations as well as emergency response or mobile medical services, where a unit may be quickly deployed to provide oxygen for medical facilities or various military operations and emergency situations, operating on multiple power sources, including AC, DC, and rechargeable batteries, ensuring continuous operation in diverse environments. Biogas upgrading or mining operations may be used to generate oxygen or nitrogen for ventilation, inerting, or processing applications. In animal veterinary clinics, a handheld oxygen concentrator allows for a higher level of personalised animal care, where an adequate oxygen supply is crucial for the successful treatment and recovery of animals. Any land and marine mammals that may require oxygen outside normal veterinary clinic and in the local environment of the animal due the size, location, handling difficulties. For example, a racehorse that has suffered from severe exercise-induced pulmonary hemorrhage (EIPH) could benefit from oxygen therapy. EIPH occurs when small blood vessels in the lungs rupture during intense exercise, leading to bleeding into the airways. This condition may cause the horse to experience breathing difficulties, decreased oxygen levels, and overall poor performance. Administering supplemental oxygen through a handheld oxygen concentrator may help stabilize the horse by increasing oxygen levels in the blood, promoting faster recovery, and reducing the risk of further complications. This therapy could also be crucial during transport to a veterinary clinic or while waiting for more intensive medical treatment. A handheld oxygen concentrator may be seamlessly portable and integrated into existing veterinary clinic setups, producing oxygen continuously, which eliminates the need for inventory management and minimizes downtime.

In some embodiments, releasing higher column pressure to lower pressure after an equalization cycle may be achieved by a single-stage process. For example, once an equalization cycle is completed, the adsorbent column is connected to ambient air. In some embodiments, releasing higher column pressure to lower pressure may be achieved by a two-stage process. For example, once an equalization cycle is completed, the adsorbent column is first connected to ambient air, to allow the higher pressure in the adsorbent column to drop to a lower pressure (e.g., to approximate 1 atm). This step is referred to as "positive pressure release." The adsorbent column may then be connected to a vacuum pump that brings the pressure down further (e.g., to between about 0.3-0.7 bar). Lowering desorption pressure in this manner is beneficial because it enhances desorption of the residual $N_2$ and reduces the oxygen purge time. This shorter purge duration requires less oxygen to purge the column of nitrogen, as the receiving column is at a lower pressure, and enables a shortened cycle time. In some embodiments, the reduction of column pressure from higher to lower levels may be accomplished through a two-stage process operating in parallel. As an illustration, upon completion of an equalization cycle, the adsorbent column may be vented to the surrounding atmosphere while being concurrently connected to a vacuum pump.

Using the same adsorption pressure, feed volume, and quantity of adsorbents, an exemplary benchtop prototype of an exemplary disclosed oxygen concentrator produced up to about 59% more oxygen product. The recovery of oxygen, defined as the ratio of product oxygen output over feed oxygen, is an important parameter in comparing the efficiency of feed flow and the adsorption process. Due to constraints in size and maximum adsorption pressure, portable oxygen concentrators typically have a recovery rate of 30-35%. Some embodiments of the disclosed oxygen concentrators may achieve a recovery rate of 54%. Additional adjustments like use of a stronger vacuum pump could achieve still higher recovery rates.

Six Steps APSA

FIG. 1 depicts an exemplary dual-column system flow diagram of an oxygen concentrator, according to some embodiments of the current disclosure. As shown in FIG. 1, the system 100 may include a pressure pump 102, a vacuum pump 104, two zeolite containing columns 110 and 120, a vacuum storage tank 106, a product oxygen tank (or oxygen storage tank) 130, and a plurality of valves, manifolds, and sensors, to provide oxygen concentrated gas from air. It should be noted that FIG. 1 illustrates an exemplary embodiment, and several variations are possible. For example, the depicted components in FIG. 1 are merely exemplary and other embodiments of the disclosed system may have additional or fewer components. For example, in some embodiments, a different number and/or type of valves may be used. As another example, in some embodiments, more than two adsorbent columns may be used.

In some embodiments, the system 100 may include a controller (not shown) configured to control the sequence and flow of the steps in the oxygen concentrator system. The controller may control the opening and closing of the gas inlet, outlet, a plurality of valves, and the timing of opening and closing these components. The controller may control the pressure and gas flow of at least two columns containing the adsorbent. The controller may be configured to control the pressure and gas flow of oxygen tank 130 and vacuum storage tank 106. In some embodiments, the pressure changes and gas flow between different sequence and steps may be controlled by the controller.

In some embodiments, inlet air (e.g., atmospheric air, room air, air from a tank, or from any other air source) is directed into system 100 through inlet 10. The inlet air may be mostly comprised of nitrogen and oxygen. In some embodiments, the inlet air may be compressed in pressure pump 102 before delivered to column 110, 120. System 100 may separate the nitrogen from the oxygen and direct air having a higher concentration of oxygen (e.g., about 85-96% oxygen in some embodiments) out of system 100 via outlet 140 to a user. Although an oxygen concentrator is described herein, in general, system 100 (with suitable modifications) may be used to separate any type of gas molecule from feed air. In other words, in some other embodiments, system 100 may separate a different type of gas molecule from the feed gas and direct the purified gas out of system 100 via outlet 140 to a user.

As schematically illustrated in FIG. 1, system 100 may include a pair of columns 110, 120 that may assist in separating the nitrogen from the inlet air. Columns 110 and 120 may contain an adsorbent (e.g., zeolite). Zeolites are a group of naturally occurring minerals and synthetic compounds with a unique crystalline structure. They are often referred to as "molecular sieves" due to their ability to selectively adsorb and trap molecules based on their size and shape. Zeolites are primarily composed of aluminium, silicon, and oxygen atoms arranged in a three-dimensional framework, with regularly spaced pores and channels. The air may be drawn in through inlet 10, filtered, compressed, and directed to one of the columns 110, 120. Each column may include a feed end 112, 122, which may receive feed air from inlet 10, passing through a pressure pump 102, a flow sensor FS1, a pressure sensor PS1, and valves V1 or V4. In some embodiments, the feed end of columns 110, 120 may further include the outlets 30, 40 (respectively) for discharging the gas to ambient. Each column 110, 120 further includes a product end 114, 124 (respectively), which may direct purified product gas, such as oxygen, to the oxygen tank 130 or the user 140.

Figure 2:
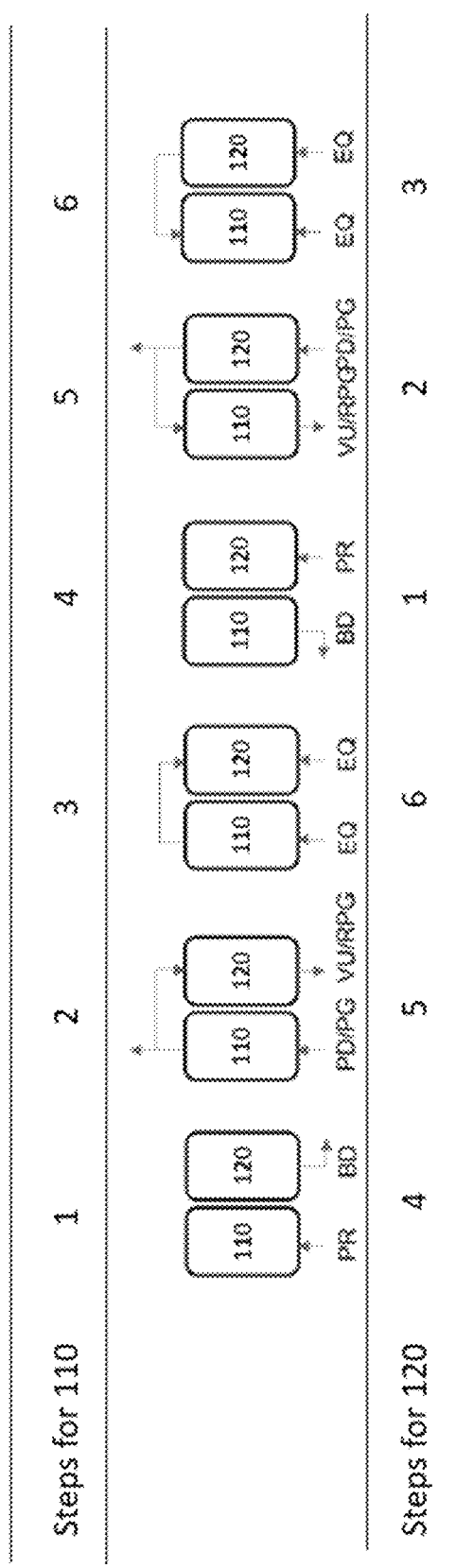
FIG. 2 depicts a schematic of the cycle sequence and steps for use in the exemplary oxygen concentrator of FIG. 1.

FIG. 2 is a schematic of an exemplary cycle sequence and steps for use in the exemplary two-column system of FIG. 1. The cycle phase for one of the columns includes the following steps: Step 1—Pressurisation (PR); Step 2—Production and Purge (PD/PG); Step 3—Equalisation (EQ); Step 4—Blowdown (BD); Step 5—Vacuum and Receiving Purge (VU/RPG); and Step 6—Equalisation (EQ). In some embodiments, the cycle time to complete one round of all six steps for one of the columns may be between about 2-15 seconds or 5-12 seconds (based on the selected parameters). In some embodiments, the cycle time may be about 9.4 seconds for one of the columns. The disclosed oxygen concentrator system may achieve a shorter cycle time with smaller zeolite adsorbent particle size, such as, smaller than about 1 mm. The disclosed oxygen concentrator system results in higher productivity, and better suitability for small-scale, handheld, portable, and ambulatory devices.

In some embodiments, in a pressurization step (Step 1), for column 110, with reference to the two-column configuration in FIG. 1 and the sequence and steps in FIG. 2, inlet air (including oxygen and nitrogen) may be compressed in pump 102, and then directed to column 110 via valve V1. When the compressed inlet air is directed into column 110, the pressure in column 110 may be increased. The pressure changes of column 110 may be monitored by a pressure sensor 4. In some embodiments, the pressurisation step time may refer to the time taken for the air in column 110 to be pressurized. In some embodiments, the pressurization step time may determine how long adsorbent column 110 may be pressurised by the inlet air. The inlet air is compressed using a given pressure pump 102 to a chosen adsorption pressure or a predetermined adsorption pressure. In some embodiments, the pressurization step time may be set in the range of between about 1 to 10 seconds or between about 2 to 4.8 seconds. In some embodiments, the pressurization step time may be less than about 5 seconds, or less than about 3.55 seconds.

Generally, the adsorption process may take place under high pressure called adsorption pressure ($P_{ads}$), where the feed gas is fed through an adsorbent bed in a column and some of the adsorbable gas molecules are trapped by the adsorbent. In contrast, the pressure when the adsorbed gas is released or desorbed is the desorption pressure ($P_{des}$). In some embodiments, $P_{ads}$ using in the disclosed oxygen concentrator system may be between about 2 to 3 bar or preferably, between about 2.4 to 2.5 bar. The relatively low $P_{ads}$ may also allow more feed air to be delivered by a pressure pump at any given pressure. The higher $P_{ads}$ results in higher recovery of oxygen from the process, but high-pressure equipment is normally bulky and heavy. Conventional industrial PSA systems typically use an absorption pressure up to about 10 bar, However, in a portable device and in particular a handheld device intended for use by an ambulatory person, the adsorption pressure needs to be achievable by small or miniature pressure pumps.

Step 2 production may begin for column 110 when the pressure in the column 110 reaches $P_{ads}$. Nitrogen of the compressed inlet air may be adsorbed by adsorbent when column 110 reaches the adsorption pressure. High-pressure oxygen product may flow to the product end 114, which may later be delivered to three destinations, including outlet 140 to a user, oxygen tank 130, and column 120.

In some embodiments, the oxygen product may be delivered to outlet 140, when triggered by the user, such as, when breathing. The oxygen product may be delivered via valve V10. The flowrate and purity of the oxygen gas may be measured by a flow sensor and an oxygen sensor. The system 100 may adjust the system accordingly when the flowrate and purity of the oxygen results does not meet the predefined requirements.

In some embodiments, production of oxygen may be delivered into oxygen tank 130 by the pressure differences between column 110 and oxygen tank 130, which is called differential pressure. Oxygen tank pressure (PB) is the pressure at oxygen tank 130 as shown in FIG. 1, which may be maintained above a certain level, such as between about 1.5 to 2.5 bar, or preferably, between about 1.9 to 2.0 bar. In some embodiments, product gas may be allowed to flow into oxygen tank 130 only when pressure of column 110 exceeds PB. In some embodiments, the initiation and the flow of oxygen production may be solely controlled by pressure differences between the column and the oxygen tank. In some embodiments, a pressure regulator and a flow controller may be not incorporated into system 100, for example, to reduce the size and/or weight for a portable or handheld system. Consistent with disclosed embodiments, the exemplary oxygen concentrator system illustrated in FIG. 1 may regulate flow by using differential pressure, which may be a spontaneous process, rather than with the use of the pressure regulator and flow controller.

In some embodiments, regarding purge step as a part of Step 2, a portion of oxygen product in production end 114 of column 110 may be sent to column 120 through valve V9 as a purge gas to column 120. The purge gas, which, in some embodiments, may be part of the product gas from column 110 and may have 90% oxygen, may be directed through the receiving column, which is column 120 for this case, to help regenerate the adsorbents in preparation for the following cycle. The purge step may ensure that high purity oxygen fills the product end and cleans the adsorbent surface. In the disclosed oxygen concentrator system of FIGS. 1 and 2, purge may occur at the end of desorption of the vacuum step when the receiving column pressure is at $P_{des}$. In some embodiments, purge pressure (PPG), which refers to the pressure of the column that is receiving the purge, may be set between about 0.3-0.8 bar, preferably between about 0.45 to 0.55 bar. When in this pressure, the oxygen required in purge gas may be low, as it occurs when the receiving column is at the lowest pressure point in each cycle. Having the purge flow pass through the receiving column increases its pressure by only a small amount, for example 0.05 bar.

Consistent with disclosed embodiments, the purge volume may be set between about 50-100 std cm$^3$/cycle, in some embodiments, preferably to be about 75 std cm$^3$/cycle, a purge volume optimized by test results. It is found that if the purge volume is held constant, altering either the purge flowrate or purge time within the range specified hereafter, there is no significant impact on the process production.

In some embodiments, the purge flowrate may be set between 4 to 23 standard litres per minute (slpm) and purge time may be set between 0.2 to 1.2 seconds. Varying purge flowrate and varying purge time within the range has negligible impact on oxygen production if purge volume is kept constant. Further, purge gas may be delivered via the equalisation channel, and thus controlled by the equalisation valve V8 as shown in FIG. 1, or via a separate purge channel. Both configurations have been tested and similar results are obtained. In some embodiments, the oxygen concentrator system may implement an instant purge step with a purge time of less than 1 second. Test results indicate that the instant purge step helps reduce the oxygen product required for purging and shorten the cycle time.

Consistent with the disclosed embodiments, the two evacuation steps for column 120 (Step 4 and Step 5) occur when column 110 is running Step 1 and Step 2. Step 4 is a blowdown step. For column 110, the blowdown step (Step 4), occurs after Step 3, the equalisation step. For column 120, as shown in FIG. 2, the blowdown step (Step 4), occurs when column 110 is running on Step 1, the production step. When the pressure of column 120 is reduced, the adsorbed gas may be released or desorbed from the adsorbent and at the end of the step, the inside of column 120 may be rich in nitrogen. In some embodiments, the blowdown step may discharge the desorbed nitrogen to ambient through outlet 30 via valve V3 for column 110, or through outlet 40 via valve V6 for column 120. In Step 4, the column feed end 112 and 122 may be open to ambient environment, and the column pressure may be dropped to near-ambient pressure, which is about 1.0-1.2 bar, more preferably, 1 bar. After that, the vacuum pump is used to further reduce the column pressure. The incorporation of the blowdown step prevents the exposure of the vacuum pump to positive pressure and helps in achieving a higher level of vacuum. This benefit is found to be significant in the tests when the given vacuum pump capacity is considerably less than the pressure pump capacity. Blowdown time may be 0.5 to 1.5 second, which is enough to drop the column pressure to near-ambient pressure. A blowdown step longer than 1.5 second is not desirable because it takes up the available vacuum time within the overall production cycle, thus reducing the vacuum level that the process may achieve.

Step 5 is a vacuum and receiving purge step. During this step, the desorbed gas (e.g., nitrogen) from the column undergoing desorption is removed using vacuum pump 104 via valves V2 and V5 for columns 110 and 120, respectively. Meanwhile, the column undergoing desorption receives the purge gas from the other column (the column undergoing adsorption). Consistent with the disclosed embodiments, Step 5 for column 120 may include evacuation of the desorbed nitrogen by vacuum pump 104 via valve V5 and receive the oxygen from column 110 as the purge gas to clean the adsorbent. The time the vacuum pump works during the vacuum step is called vacuum step time.

In the present disclosure, it is to be noted that Step 4 (the blowdown step) and Step 5 (the vacuum and receiving purge step) are executed sequentially. However, it should be noted that this is not the sole operation model. In some embodiments, after an equalization cycle, Step 4 and Step 5 may be performed at the same time. Alternatively, Step 4 may be omitted, and only Step 5 may be executed by directly connecting the column 120 to vacuum pump 104 after an equalization cycle. In some other embodiments, Step 4 may be carried out after an equalization cycle, and the column feed end 112 and 122 may be open to ambient environment, while Step 5 may be eliminated.

In some embodiments, $P_{des}$ is the desorption pressure when the adsorbed gas is released or desorbed, using the oxygen concentrator system. $P_{des}$ may be between about 0.3 to 0.8 bar, preferably, between about 0.4 to 0.5 bar. In some embodiments, the desorption pressure, $P_{des}$, may be achieved using miniature vacuum pumps. Generally, such a miniature vacuum pump may have difficulties operating below 0.3 bar. Using the disclosed oxygen concentrator system, the miniature vacuum pumps reach desorption pressure more quickly, more effectively matching the desired pressurisation time, and keeping the entire cycle time for all the six steps below a desired maximum, such as, for example, a cycle time of all six steps of about 12 seconds. The vacuum buffer or vacuum storage tank 106 (see FIG. 1) also helps in making the desorption process more efficient and reducing cycle time. For example, with reference to FIG. 1, when the columns 110 and 120 are not connected to the vacuum pump 104 (e.g., during the blowdown step), the vacuum pump 104 pumps down (e.g., reduces the pressure in) the vacuum storage tank 104. Consequently, during the vacuum step, when one of these columns 110, 120 is connected to the vacuum pump 104 to pump down the pressure in the column to sub-atmospheric pressure, the column may be purged more quickly and efficiently.

In some embodiments, vacuum step time may be set in a range of about 2.5 to 4.3 seconds, preferably about 3.05 seconds. The selection of vacuum step time may allow the adsorbent column to reach the chosen desorption pressure using a given vacuum pump. In some embodiments, vacuum step time may be slightly shorter than pressurisation time (for example, about 0.5 second less in some embodiments) to accommodate the blowdown step.

In some embodiments, a vacuum release step occurs after the vacuum step. During the vacuum release step, column 110 is open to the ambient environment at its feed end 112 to raise pressure to near-ambient pressure before the pressurisation step takes places. The incorporation of the vacuum release step prevents the exposure of the pressure pump 102 to vacuum. It may also assist in achieving higher adsorption pressure. The vacuum release step may be in the range of 0.2 to 0.5 second, during which the column pressure increases to near-ambient. A vacuum release step longer than 0.5 second results in lower adsorption pressure and thus negatively impacts the oxygen production.

In some embodiments, Step 3, the equalization step may start for column 110 and column 120 when the product gas, such as, high-pressure oxygen of column 110 is sent to column 120 to purge the column 120, and at the same time, inlet gas is admitted to columns 110 and 120 from the inlet 112 and 122, until the pressures between the two columns 110 and 120 are approximately equal to each other. When column 110 is under Step 3, column 120 undergoes step 6. The equalization steps are terminated when the pressures in the two beds are roughly equal at a predetermined equalisation pressure, and the second half of the cycle, in which column 120 goes through Steps 1-3 and column 110 goes through Steps 4-6, begins.

In some embodiments, equalisation pressure ($P_{EQ}$), which refers to pressure at the column product end when the equalisation step ends, may be set between about 1.3 to 2 bar, preferably between about 1.4 to 1.5 bar. The equalisation step may increase oxygen recovery and reduce the consumption of power throughout the process. The optimum $P_{EQ}$ in the process is found to be 1.4 to 1.5 bar implying near-complete equalisation, which is known to give higher oxygen recovery than using in-complete equalisation. In some embodiments, the equalisation time may be between about 0.2 to 0.5 second, and preferably about 0.45 second. Based on the test results, the gas exchange during the equalisation step takes place predominantly, but not completely, within the first 0.2 second. An equalisation step shorter than 0.2 second is not sufficient to reach the optimum $P_{EQ}$ range. Equalisation is typically complete by 0.5 second, which means the two columns have reached equal pressure and there is no more gas exchange occurring. Further increase of the equalisation time has a detrimental impact on the efficiency of oxygen production, as it results in longer cycles.

Generally, there are three equalisation schemes, including top-top, bottom-bottom, and cross. A top-top equalisation scheme is found to result in the highest oxygen production. Further, during the equalisation step, the feed end 112, 122 of columns 110, 120 may be connected to the pressure pump (P), the vacuum pump (V), the ambient environment (A), or it may be sealed(S). Various combinations of these configurations are tested, such as P/P, P/V, A/S, etc. The optimum combination is found to be P/P and A/P, such that the pressure pump delivers feed air to both columns, or the pressure pump delivers feed air to the lower-pressure column and the high-pressure column is open to ambient environment. In a small-scale device, the pump capacity, constrained by its size and weight, is often the limiting factor of process production. Hence, in order to maximize production, the pump capacity must be utilized to its maximum potential. The column feed-end 112, 122, configuration of P/P or A/P ensures that there is no idle time for the pressure pump. During the equalisation step, the low-pressure column is being pressurised on both ends-feed air from the feed end 112, 122, and the high-purity oxygen being exchanged at the product end 114, 124. Furthermore, the pressure reduction in the high-pressure column is slowed down by feed air supply in P/P configuration, thus less $N_2$ is desorbed and passed on to the alternative column.

In some embodiments, a feed flowrate may be on average about 7 to 8 slpm, which may be equivalent to about 300 to 800 std $cm^3$/cycle. In some cases, a higher feed flowrate may be desirable, as the column 110, 120 may be pressurised to the given adsorption pressure in less time, or the column may reach a higher adsorption pressure in a given step time. The stated flowrate is the maximum for currently existing off-the-shelf miniature pressure pumps at the chosen pressure range, which is between $P_{EQ}$=1.4 bar and $P_{ads}$=2.5 bar. Consistent with disclosed embodiments, the process may operate with partial feed. During partial feed, after column pressure reaches a certain $P_{ads}$, a portion of the feed flow may be directed to vent during pressurisation and/or a purge step. Tests conducted by venting 3-7% of the feed in each cycle (which keeps adsorption pressure at a given level for a longer period) indicated no significant effect on the production. The pressure of the column may be controlled by the volume of feed gas in each cycle. Pressure increases with pressurisation time because more feed gas is delivered. By using partial feed, the column may be maintained at a given pressure while running over a longer cycle time.

Four Phases APSA

In an alternative embodiment, the APSA system may include four phases, phase 1, phase 2, phase 3, and phase 4. Phase 1 and phase 3 are oxygen production phases, during which oxygen is concentrated at columns 110 and 120, respectively. Columns 110 and 120 are connected to either a positive pressure pump or a negative pressure pump delivered to removable module 150 and output 140. In phase 1, column 110 is undergoing an adsorption process to output the concentrated oxygen product, and column 120 is undergoing a desorption process to discharge the saturated nitrogen or adsorbed air filled in column 120. During phase 3, column 110 is undergoing a desorption process to discharge the saturated nitrogen or adsorbed air filled in column 110, and column 120 is undergoing an adsorption process to output concentrated oxygen product. Phase 2 and phase 4 are equalization processes, during which system 300 may be configured to equalize the pressures in both columns. Four phases may constitute a cycle of oxygen production. During operation of the portable oxygen concentrator, the system 300 may keep cycling through the four phases to provide the concentrated oxygen.

Figure 3A:
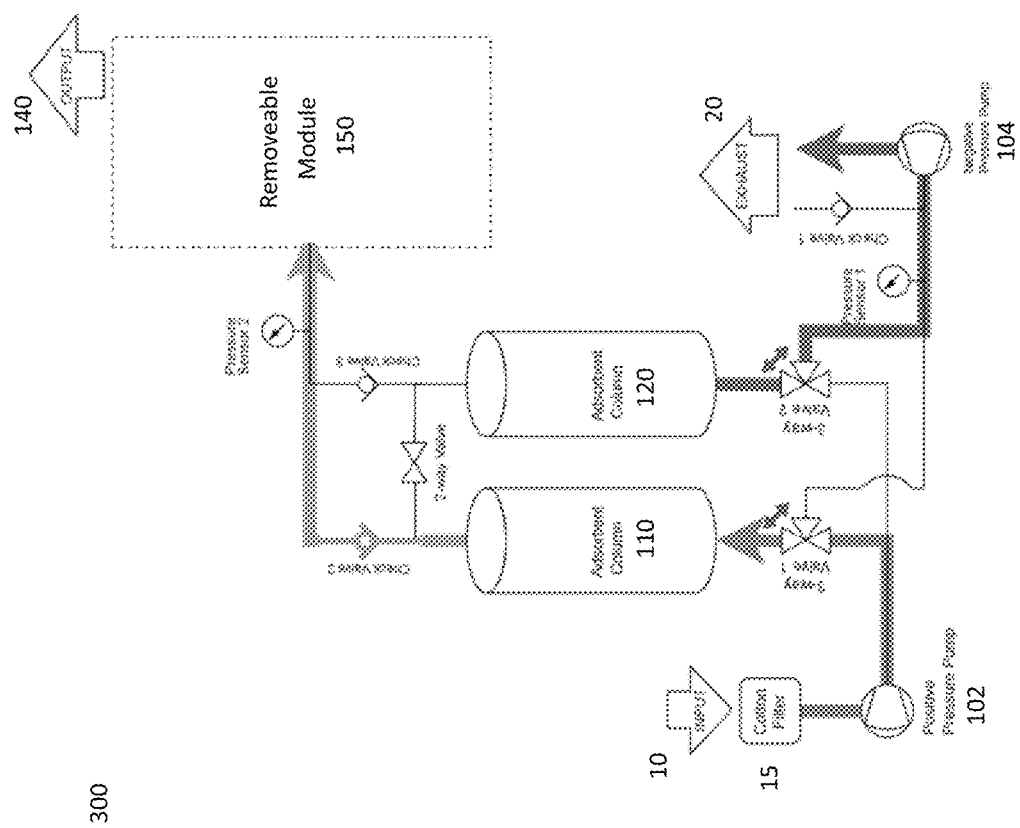
FIGS. 3A and 3B depict the exemplary diagram flows for phase one and phase three, respectively, of an exemplary oxygen concentrator according to an alternative embodiment of the current disclosure.

FIG. 3A illustrates a flow diagram corresponding to phase 1 of an oxygen concentrator of the alternative embodiment. As shown in FIG. 3A, the system 300 may include an input 10, a filter 15, a positive pressure pump 102, a negative pressure pump 104, at least two adsorbent columns 110, 120, an exhaust 20, a removable module 150, a product output 140, and a plurality of valves, manifolds, and sensors, to provide oxygen concentrated gas from air. The depicted components in FIG. 3A are merely exemplary, and other embodiments of the disclosed system may have additional or fewer components. For example, in some embodiments, a different number and/or type of valves may be used. As another example, in some embodiments, more than two adsorbent columns may be used. The valves, manifolds, and sensors may provide similar features as described in the previous embodiment.

In some embodiments, the system 300 may include a controller (not shown) configured to control the sequence and flow of the phases in the oxygen concentrator system. The controller may control the opening and closing of the gas inlet, outlet, a plurality of valves, and the timing of opening and closing these components. The controller may include similar features as described in the previous embodiment.

As schematically illustrated in FIG. 3A, system 300 may receive inlet air (e.g., atmospheric air, room air, air from a tank, or from any other air source) containing approximately 21% oxygen through inlet 10. The inlet air may be filtered by filter 15 located at input 10. Filter 15, in certain instances, may be a cotton filter. In some embodiments, filter 15 may be an electrostatic and hydrophobic polypropylene material, or any other suitable material.

During phase 1, column 110 is under the adsorption process, the inlet air may be pressurized in positive pressure pump 102 and substantially channeled into column 110 through 3-way valve 1. In some embodiments, pressure pump 102, which functions as a compressor, is responsible for pressurizing the column to a predetermined level with the pressurized air flow through. Column 110, containing an adsorbent (e.g., zeolite), may separate mixture components by virtue of the mixture components' chemical and physical properties. In some embodiments, column 110 filled with an adsorbent (e.g., zeolite) may separate the oxygen product from the pressurized air with the other gas (e.g., nitrogen). The adsorbent may remove nitrogen from pressurized air.

3-way valve 1 is a valve with three ports. 3-way valve 1 may be used to divert or switch flow between sources. In some embodiments, during phase 1, 3-way valve 1 may permit compressed air to pass through and enter column 110, where the air is separated into oxygen and nitrogen by the adsorbent material. At the same time, 3-way valve 1 may be configured to serve the connection between column 110 and negative pressure pump 104. As we will explain in phase 3 and FIG. 3B, 3-way valve 1 may open the connection between column 110 and negative pressure pump 104, while closing the connection between column 110 and positive pressure pump, thereby releasing the saturated nitrogen from column 110 to exhaust 20 via check valve 1.

Referring to phase 1, column 110 is under an adsorption process to output the concentrated oxygen to removable module 150. The adsorbents within column 110 adsorb nitrogen molecules from the feed, resulting in a product rich in oxygen concentration, with a purity level exceeding 90%. The concentrated oxygen product may then be transferred from column 110 to removable module 150 via check valve 2. The concentrated oxygen product may be stored in removable module 150 and eventually directed to output 140, corresponding to a user's inhalation. Meanwhile, the adsorbed nitrogen is collected in column 110 during the adsorption process.

During phase 1, column 120 may undergo a desorption process facilitated by its connection to negative pressure pump 104 through 3-way valve 2. 3-way valve 2 opens two ports between column 120 and negative pressure pump 104 while simultaneously closing the connection to positive pressure pump 102. Negative pressure pump 104 may generate a sub-atmospheric pressure condition where the pressure inside a closed system 300 is less than that of the external atmosphere. This condition creates a suction or vacuum effect, which is the foundation for various types of vacuum pumps. By harnessing this sub-atmospheric pressure, the nitrogen previously adsorbed in column 120 during the adsorption process may be effectively extracted through the vacuum line and ultimately expelled through exhaust 20.

Check valve 1 may be used to provide protection to negative pressure pump 104 given the high positive pressure of the column at the start of the desorption process. Sometimes, due to the significant pressure difference between columns and negative pressure pump 104, keeping the positive pressure may damage negative pressure pump 104. Having a check valve 1 next to negative pressure pump 104 may alleviate the risk by releasing high pressure in columns after the adsorption process.

Pressure sensor 1 may be used to monitor the pressure of the vacuum line or the column that connects to negative pressure pump 104 at any given time. Pressure sensor 1 may also be configured to monitor the desorption pressure achieved by a column, monitor the vacuum leak detection, and predict the column's lifespan. As the column achieves a deeper vacuum, the adsorbent becomes cleaner and may adsorb more nitrogen in the next cycle. The duration of the desorption process is determined by the adsorption process, which is based on the time it takes to achieve a predetermined target adsorption pressure. The negative pressure monitored by pressure sensor 1 may indicate how "clean" the columns are at the end of the desorption process. Accordingly, the negative pressure measurement results are one of the key factors to automation algorithm used to determine the column's lifespan, as explained hereafter. Pressure sensor 1 may also detect negative pressure leaks when the columns fail to reach expected negative pressure levels corresponding to the duration it receives negative pressure pump time.

Figure 3B:
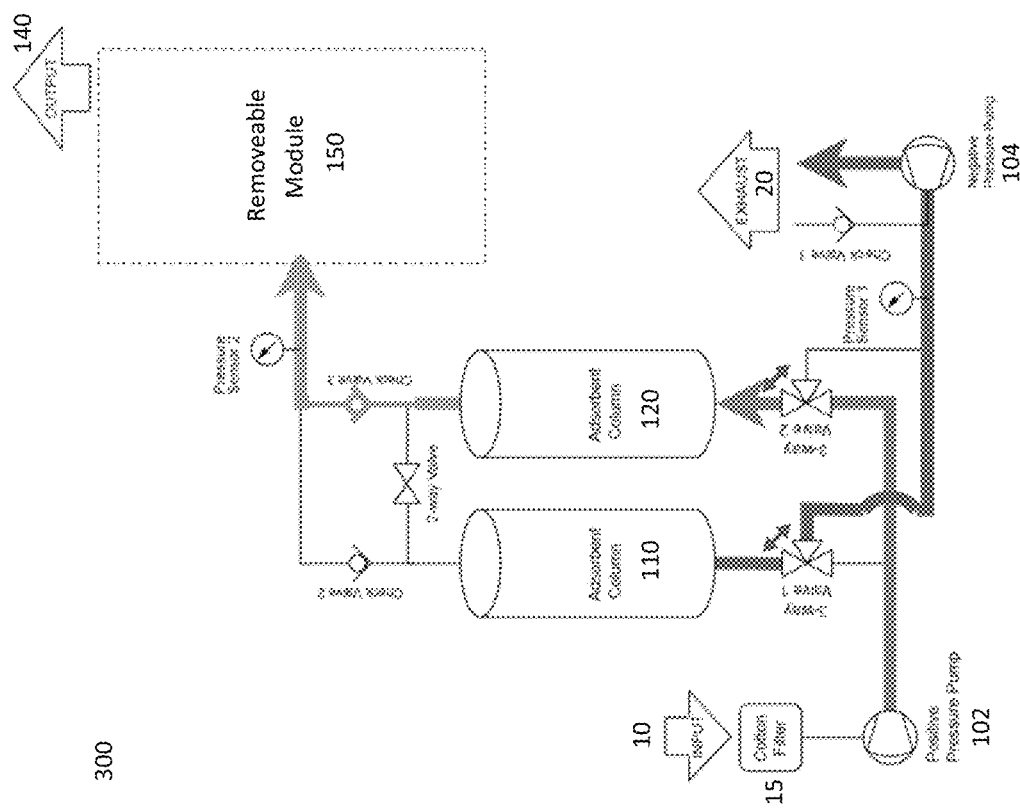

FIG. 3B illustrates a flow diagram corresponding to phase 3 of an oxygen concentrator. In phase 3, the connection between column 110 and positive pressure pump 102 is closed, and the connection between column 110 and negative pressure pump 104 is open via 3-way valve 1. Similar to column 120 in phase 1, column 110 may undergo a desorption process, the nitrogen previously adsorbed in column 110 during the adsorption process of phase 1 may be effectively extracted through negative pressure provided by negative pressure pump 104 and ultimately expelled through exhaust 20.

As shown in FIG. 3B, column 120 may be configured to connect to positive pressure pump 102 through 3-way valve 2, while the connection between column 120 and negative pressure pump 104 remains closed. During phase 3, column 120 may undergo an adsorption process by taking the pressurized input air from positive pressure pump 102. The adsorbent, such as zeolite, contained within column 120 may effectively separate oxygen from the input air and output the concentrated oxygen to removable module 150. Meanwhile, the adsorbent may adsorb the nitrogen. The adsorbed nitrogen may be collected in column 120 during the adsorption process.

Figure 4:
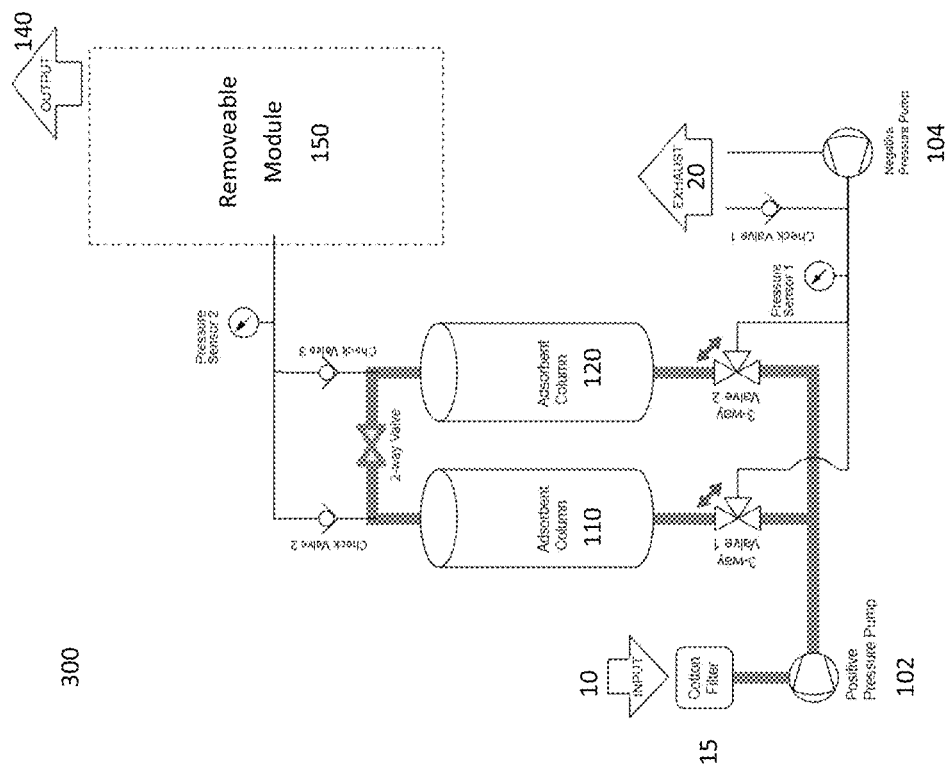
FIG. 4 depicts another exemplary diagram flow of phase two and phase four of the exemplary oxygen concentrator of FIGS. 3A and 3B.

FIG. 4 illustrates phase 2 and phase 4, the equalization process, to equalize the pressures in both columns. By implementing the equalization process, system 300 may reduce the time required for the columns to reach the predetermined target adsorption pressure. The duration of phase 2 and phase 4 may be typically less than one second. During the equalization process, both columns 110 and 120 are connected to positive pressure pump 102, while their connections to negative pressure pump remain closed. The output ends of columns 110 and 120 may be configured to connect to each other via a 2-way valve. The 2-way valve may only open the connections of the two output ends during the equalization process of phase 2 and phase 4. During phase 1 and phase 3, the 2-way valve between column 110 and column 120 remains closed.

Removable Module

In some embodiments, a removable module within the disclosed oxygen concentrator may be used to receive the concentrated oxygen from the columns. The removable module may be used to facilitate modification, purification, or replacement of the components within the module, for reasons related to the patient's usage need, product upgrades, or user convenience. Specifically, the removable module may be configured to enhance the purity of the oxygen and regulate the oxygen flow to the user.

Figure 5A:
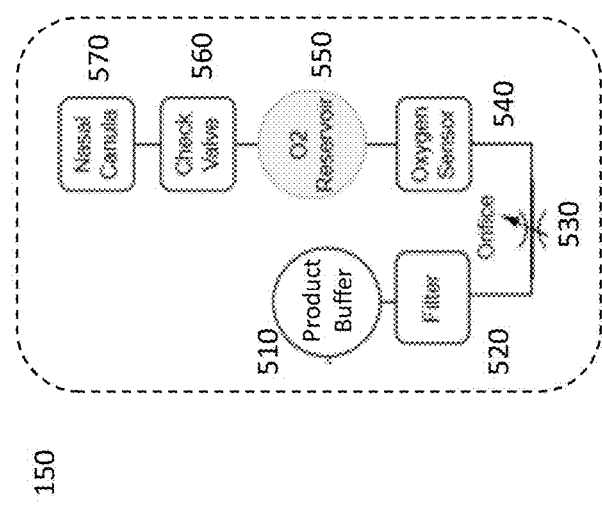
FIG. 5A depicts a flow diagram of the removable module of the exemplary oxygen concentrator according to some embodiment of the current disclosure.

FIG. 5A illustrates a schematic flow diagram of a removable module of the oxygen concentrator according to the current disclosure. As shown in FIG. 5A, removable module 150 may include product buffer 510, filter 520, orifice 530, oxygen sensor 540, at least one oxygen reservoir 550, check valve 560, and nasal cannula 570, consistent with disclosed embodiments.

In some embodiments, product buffer 510 may be configured to contain adsorbent material, such as zeolite, in order to increase storage capacity and further enhance the purity of the oxygen product subsequent to the initial adsorption process that occurs in the adsorbent-filled columns. The material used to fill product buffer 510 may include molecular sieves; activated carbon, silver, and copper bases adsorbents, perovskite oxides, polymeric membranes, zirconium-based adsorbents, etc. Moreover, product buffer 510 may play an important role in facilitating the flow of concentrated oxygen. Calibrating the product buffer, including the amount of adsorbent used, may help protect against the buffer being charged up by oxygen product and being depleted by oxygen delivery to the user. Such balance may help to maintain a consistent flow of oxygen, which is important for medical and industrial applications. In some embodiments, product buffer 510 filled with an adsorbent may be able to stabilize a flow rate of the oxygenized air. The flow rate of concentrated oxygen passing through the adsorbent-filled product buffer 510 may be more stable than if it were to bypass the product buffer 510.

In some embodiments, filter 520 may trap the particulates and contaminants that may arise within the system or enter from external sources. Filter 520 serves to promote seamless and effective operation while safeguarding the user against inhalation of these harmful substances. Filter 520 may filter out zeolite leakage from the product buffer. Filter 520 may be any type of material, such as a bio-compatible filter material, cotton, or more.

As shown in FIG. 5A, orifice 530 may be a precisely sized aperture that restricts the flow of concentrated oxygen. In particular, orifice 530 may act as a precise flow regulator, enabling a specific amount of oxygen to flow while also measuring the rate of flow, reducing pressure, or limiting the flow.

In some embodiments, oxygen sensor 540 may be used to measure the percentage of oxygen following the passage of oxygen flow through orifice 530, but prior to its entry into oxygen reservoir 550. The measurement of oxygen percentage may guarantee that the oxygen quantity administered to a patient is within the desired or predetermined range as specified by the user. Oxygen sensor 540 may be programmed to activate an alarm to notify the user in the event of low oxygen percentages being detected. The alarm may take any form, such as sound, light, a message on a user interface, and so on.

In some embodiments, oxygen reservoir 550 may take the form of a balloon or a plastic-bag like material. Oxygen reservoir 550 may be configured to inflate with a low pressure of oxygen flow and to expand during user exhalation as it fills with oxygen product, subsequently deflating during user inhalation. Two exemplary embodiments of the oxygen reservoir 550' and 550" are depicted in FIG. 5B and FIG. 5C.

As shown in FIG. 5B, oxygen reservoir 550' may be an expandable balloon-like receptacle, capable of stretching from a single spot or a solitary juncture in a flow path tube of the concentrated oxygen. In some embodiments, the single spot may be a single circular spot. In some embodiments, the single circular spot may comprise inflatable material. In some embodiments, the single spot or juncture may be located between oxygen sensor 540 and check valve 560, which precedes nasal cannula 570. The flow path tube may be a conduit through which oxygen product flows between oxygen sensor 540 and check valve 560. In some embodiments, the flow path tube may connect different components inside removable module 150. In some embodiments, the flow path tube may be a conduit that comprises a section of an inflatable material. This inflatable material may be made of a flexible and resilient material that can be inflated or deflated as needed. The inflatable material may be made of any suitable material, such as rubber, plastic, or other similar materials. The inflatable material may be designed to be inflated to a predetermined size and shape, which may be determined based on the specific application or use of the flow path tube. Additionally, the inflatable material may be deflated when not in use, which may help to reduce the overall size and storage requirements of the flow path tube.

In an alternative embodiment, as shown in FIG. 5C, oxygen reservoir 550" may comprise an expandable balloon-like material seamlessly integrated into the flow path tube of the concentrated oxygen. The flow path tube may include at least two distinct materials, with one being a balloon-like material that inflates during user exhalation. This balloon-like material may be configured to connect to the other tubular plastic material, which has limited or no inflatable or shape-changing properties.

In some other embodiments, as shown in FIG. 5D, oxygen reservoir 550" may include an expandable, balloon-like material that may be inflatable from a connection point from a main flow path tube. The flow path tube may have a reduced inner path diameter, or reduced cross-section area around the opening of oxygen reservoir 550"'. This narrower flow path may facilitate the passage of the oxygen product around oxygen reservoir 550"', thereby generating a venturi effect. As a fluid flows through a reduced cross-section area of a tube, pipe or channel, its velocity increases, resulting in a reduction in pressure (vacuum). This decrease in pressure may draw the oxygen stored in oxygen reservoir 550"' to merge with the oxygen product flow. The diameter of the pathway may be adjusted to have a minimal or negligible vacuum pressure under regular oxygen output flow so that it will not impede the "filling up" of oxygen in oxygen reservoir 550"'. When a user inhales, the venturi effect may become significant as the oxygen product flow across the narrow path increases. This may create a vacuum effect that draws out the oxygen stored in the reservoir.

In some embodiments, check valve 560 may take the form of a duckbill check valve. As shown in FIGS. 5B and 5C, check valve 560 may be positioned downstream of oxygen reservoir 550 and function as a unidirectional conduit for oxygen delivery to a patient further via nasal cannular 570. By effectively obstructing user exhalation and preventing the ingress of contaminations into removable reservoir 150, this valve may ensure the purity and efficacy of the oxygen supply. In some embodiments, as shown in FIGS. 5B and 5C, check valve 560 is situated at a more distal location along the flow path tube. Notably, check valve 560 does not cover or obstruct a filling aperture of oxygen reservoir 550, nor does it obstruct the interconnections or material transaction areas between oxygen reservoir 550 and the flow path tube. In some embodiments, the filling aperture of the oxygen reservoir 550 may refer to the opening through which oxygen product is filled into the reservoir. Additionally, in some embodiments, a single check valve 560 located downstream at a distal point along the flow path tube may regulate a plurality of oxygen reservoir 550 situated upstream along the flow path tube.

In some embodiments, check valve 560 may require a cracking pressure to enable the flow of oxygen product across check valve 560. The cracking pressure may be defined as a pressure of oxygen product flow that may open the valve. In some embodiments, cracking pressure is the pressure differential between the inlet and outlet ports of a valve when flow is first detected on the output side. The cracking pressure may induce a slight back pressure, compelling the oxygen product in the flow path tube to fill and expand oxygen reservoir 550 first. Once oxygen reservoir 550 is filled and built-up pressure may have reached the cracking pressure and oxygen product may propel through check valve 560. As a result, the oxygen product from the source may bypass oxygen reservoir 550 and stream through to nasal cannula 570 and outlet 140.

In some embodiments, the inhalation of a user may generate a negative or vacuum pressure on nasal cannular 570. The suction effect may facilitate the flow of the oxygen product from oxygen reservoir 550 into nasal cannula 570, thereby depleting oxygen reservoir 550. In some embodiments, one-way check valve 560 may be configured to impede the entering of contamination, such as $CO_2$, bacteria, and moisture, from user exhalation into oxygen reservoir 550 and dilute the oxygen concentration therein. In addition, avoiding moisture may reduce the risk of bio-organism growth inside oxygen reservoir 550, therefore reducing the frequency of replacement for removable module 150. A UV-C LED light (not shown) may be added to sterilize contamination in the oxygen reservoir 550.

Removable module 150 may be periodically replaced. In some embodiments, replacement frequency may vary, ranging from daily, weekly, to biannually, or annually, with options for replacement every two or three weeks, one, two, three, four, or five months, every half year, or every year. Additionally, the replaced removable module 150 may come in various models, each with its own product buffer size, adsorption amount in product buffer 510, oxygen storage capacity, and quantity of oxygen reservoir 550. This allows users or patients to select the most suitable model for their needs.

As shown in FIGS. 3A-4, a pressure sensor 2 is located next to removeable module 150. More specifically, pressure sensor 2 is positioned adjacent to product buffer 510 which is filled with adsorbent. Pressure sensor 2 may be used to measure the pressure that flows from the adsorbent columns 110, 120 to product buffer 510 within the removable module. In some embodiments, pressure sensor 2 may detect a low pressure change rate near the entrance of product buffer 510, indicating a high oxygen storing capacity at product buffer 510. On the other hand, a high pressure change rate detected by pressure sensor 2 next to the entrance of product buffer 510 may indicate a low oxygen storing capacity at the product buffer 510, indicating that product buffer 510 is approaching its time for needing replacement.

Figure 5E:
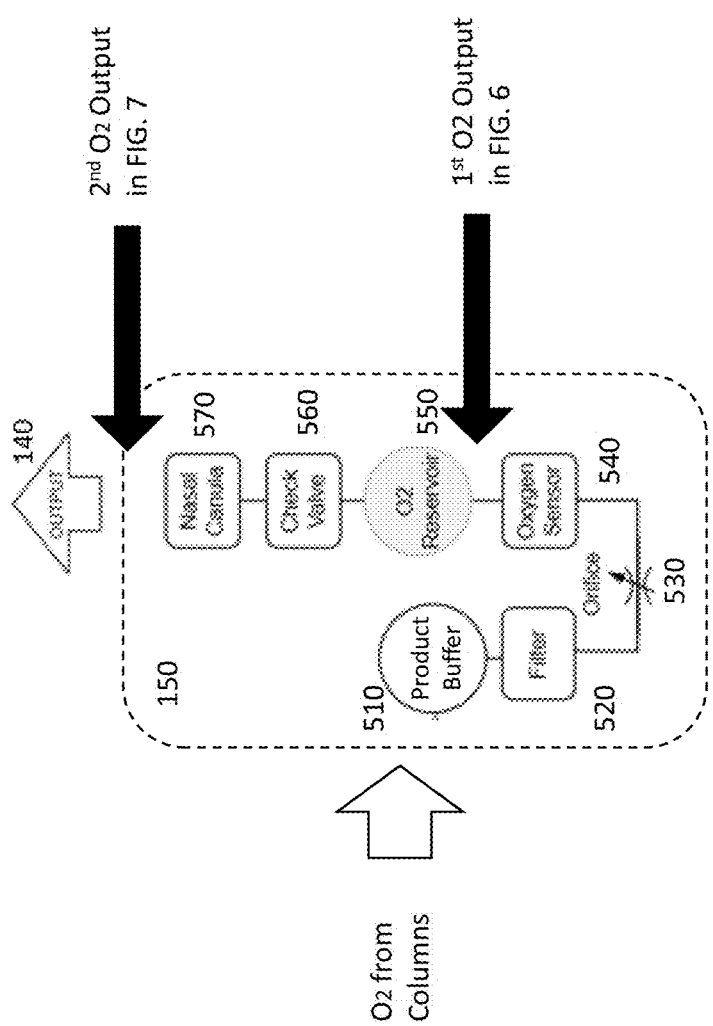
FIG. 5E depicts a diagram of the removable module highlighting the first and second measurement points utilized for measuring the oxygen product flow in the exemplary oxygen concentrator depicted in FIG. 5A.

FIG. 5E depicts a diagram of the removable module highlighting the first and second measurement points utilized for measuring the oxygen product flow in the exemplary oxygen concentrator depicted in FIG. 5A. As shown in FIG. 5E, the first point is prior to the introduction of the oxygen product into oxygen reservoir 550. The second point, on the other hand, is situated after the oxygen product has travelled through oxygen reservoir 550, check valve 560, and nasal cannula 570. The measurement outcomes of the first point are illustrated in FIG. 6; while the measurement outcomes of the second points are illustrated in (c), (d), and (e) of FIG. 7.

Figure 6:
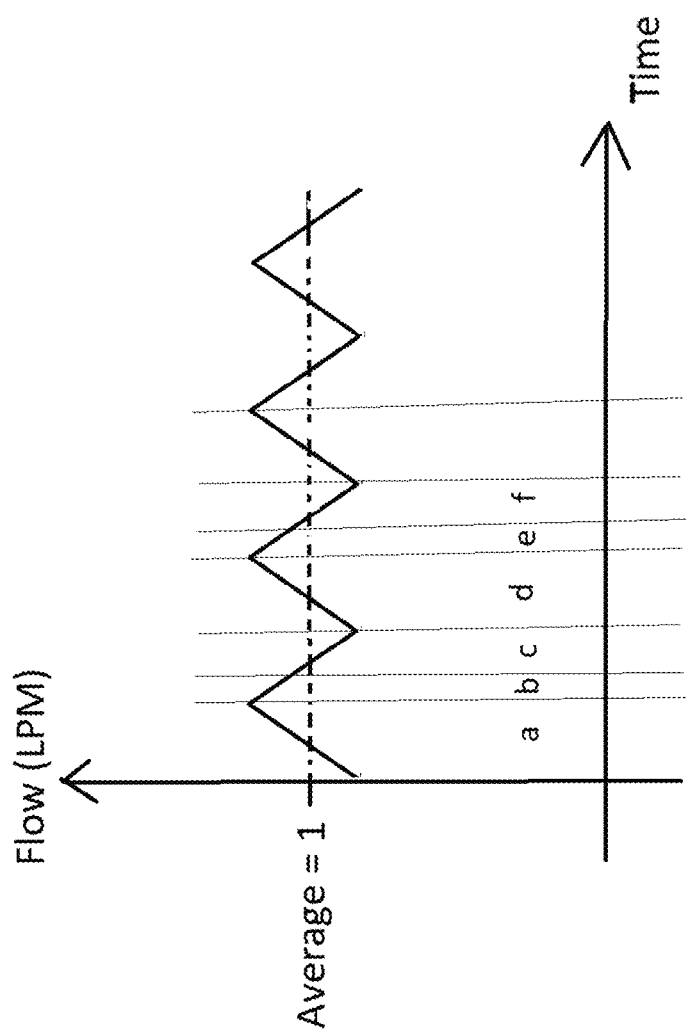
FIG. 6 depicts an exemplary output flow of oxygen product, which is measured at the first point of the removable module of FIG. 5E.

FIG. 6 depicts an exemplary oxygen product flow, which is measured at the first point of removable module 150. As shown in FIG. 6, the oxygen flow may exhibit fluctuation. In order to provide a more comprehensive understanding of the underlying reasons for these fluctuations, the flow is divided into distinct regions, namely a, b, c, d, e, and f.

In region a (phase 1), column 110 may be subjected to an adsorption process, wherein the pressure within column 110 may gradually increase until it reaches a predetermined target adsorption pressure, preferably in the range of 1.7 to 3 bar absolute. Meanwhile, product buffer 510 may be temporarily storing the oxygen product. Orifice 530 may be used to limit the oxygen product flowing downstream to output 140. In some embodiments, orifice 530 may be calibrated to maintain an average output of 1 LPM throughout the entire APSA process.

In region b (phase 2), columns 110 and 120 may undergo an equalization process in order to equalize the pressure between the two columns. During this process, a 2-way valve, which connects the two output ends of columns 110 and 120, is opened, causing an instantaneous drop in pressure in column 110. As a result, the pressure in columns will be lower than the pressure in the product buffer. Check valve 2 at the output end of column 110 is now closed due to the pressure difference. Therefore, the output flow during region b starts to drop. This rate of drop may be influenced by the amount of oxygen stored in product buffer 510, with the bigger product buffer capacities resulting in slower drops and smaller fluctuations in the output.

In region c (phase 3), the equalization process ends. At this point, column 120 may be ready to undergo the adsorption process. Check valve 3 remains closed as the pressure in column 120 is still lower than that of product buffer 510. Consequently, no new oxygen product is being delivered to product buffer 510. The output flow is gradually decreasing, sustained by the stored oxygen in product buffer 510.

As column 120 continues to build up pressure, it may eventually surpass the cracking pressure of check valve 3, leading to a transition into a new region d that is still in phase 3, involving the adsorption and production of column 120. Once this occurs, column 120 will begin to deliver oxygen product to product buffer 510 until it reaches target adsorption pressure.

In region e (phase 4), the process of equalizing two columns recommences. As in the previously described region b, 2-way valve that connects the two output ends of columns for equalization is opened. Once the 2-way valve opens, the pressure of column 120 may drop instantly, causing check-valve 3 to close due to the pressure differential. The output flow is sustained by the oxygen product stored in product buffer 510.

In region f (phase 1), where column 110 starts to undergo the adsorption process again. During this time, check valve 2 associated with product output remains closed due to the lower pressure of column 110 in comparison to the pressure of product buffer 510. Column 110 may build up pressure until it exceeds the cracking pressure of check valve 2, following which we proceed to repeat region a.

Figure 7:
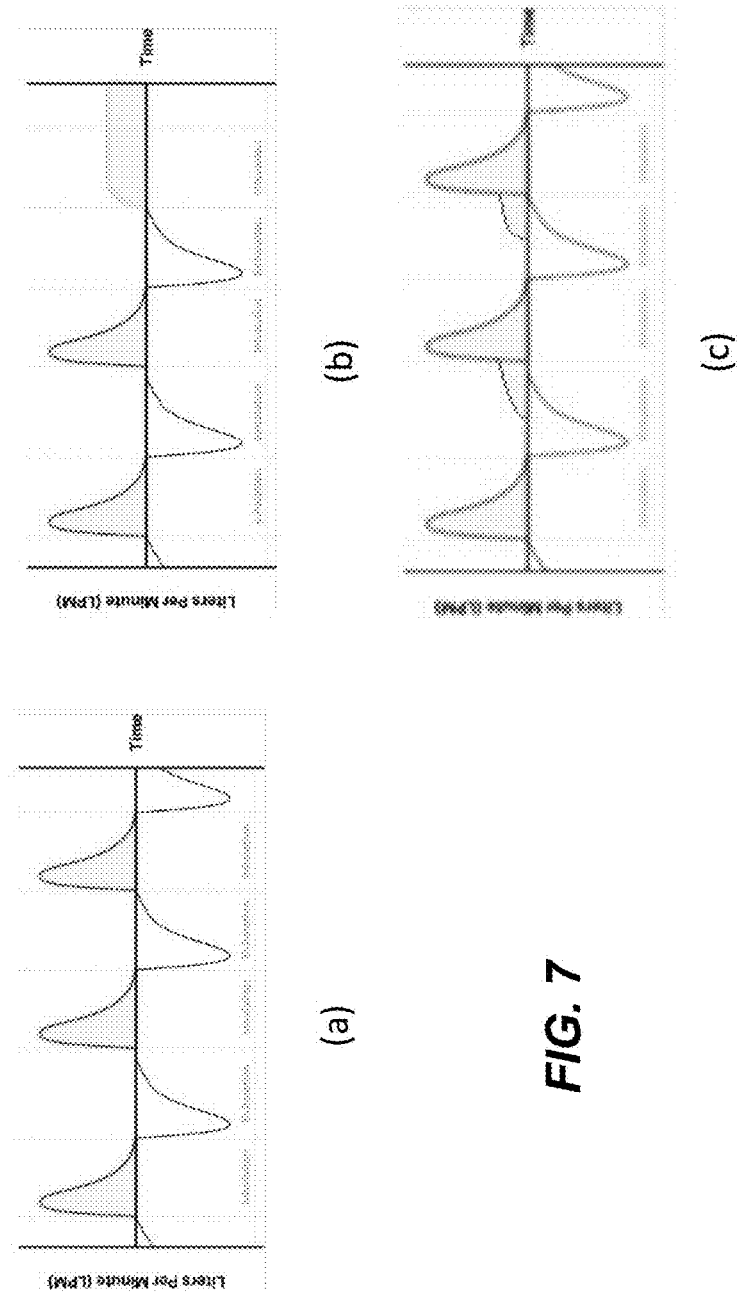
FIG. 7 depicts the exemplary oxygen product outputs measured at the second point of the removable module of FIG. 5E, under various circumstances.

FIG. 7 depicts exemplary oxygen product outputs measured at the second point, which is positioned after the oxygen product has traveled through oxygen reservoir 550, check valve 560, and nasal cannula 570, of the removable module of FIG. 5E, under various circumstances. The gray-shaded regions represent the oxygen product discharged from the device output 140. Output (a) depicts the most optimal scenario, wherein oxygen reservoir 550's additional storage capacity and check valve 560's opening mechanism correspond to the user's breathing pattern, allowing removable module 150 to dispense oxygen product without any wastage during exhalation or triggering by extra electronic devices.

In some embodiments, as shown in output (b), if no breath is detected for a specific duration, oxygen reservoir 550 will become completely filled, and the oxygen product accumulated in front of check valve 560 will exceed the cracking pressure. As a result, the oxygen product will flow directly through the nasal cannula in a continuous manner.

In some embodiments, the output of oxygen may be influenced by various factors, including the oxygen storage capacity of oxygen reservoir 550, the cracking pressure of check valve 560, the user's exhalation pressure on the user's end of nasal cannula 570, and the duration of the user's exhalation. If the user's exhalation duration is sufficiently long and oxygen reservoir 550 is fully filled, the pressure of the accumulated oxygen product in front of check valve 560 may exceed the cracking pressure, causing the oxygen to exceed the check valve before the user's inhalation, as depicted in output (c) of FIG. 7.

In some embodiments, the portable oxygen concentrator may include removable module 150 that may be affixed to the main body of the concentrator, which includes columns, pumps, batteries, valves, conduits, and other essential components. Alternatively, in some embodiments, removable module 150 may be optionally connected to the main body of the portable oxygen concentrator or extended away from the main body using retractable oxygen supply tubes.

In this particular embodiment, removable module 150 is integrated by linking it to a portable oxygen concentrator that employs a four-phase absolute pressure swing adsorption system. However, it is worth noting that alternative systems, including six-step absolute pressure swing adsorption, pressure swing adsorption, vacuum pressure swing adsorption, or any other oxygen adsorption system, may also be attached to removable module 150.

Pumps and Pump Buffer

In some embodiments, the capacity of the pressure pump may be in the range of 6 to 11 slpm at a pressure range of 1.4 to 2.5 bar. With a given amount of zeolite adsorbent and flowrate, the pressure pump may deliver gas to the adsorbent columns with a pressure between $P_{EQ}$ and $P_{ads}$, in conjunction with the choice of cycle time. Cycle time reflects the number of cycles in a minute and affects the production level in the form of a combination with feed flowrate. Working pressure range for the pressure pump ($\Delta P$) is defined as the gap between equalization pressure and adsorption pressure in the disclosed oxygen concentrator system. $\Delta P = P_{ads} - P_{EQ}$. The stated capacity combination (average 6 to 11 slpm at 1.4 to 2.5 bar) is optimum for the oxygen concentrator system within the constraint of available equipment.

In some exemplary embodiments, the capacity of the vacuum pump 104 may be set between 3 to 14 slpm at the pressure range of 0.3 to 1.0 bar. The vacuum level that may be achieved is positively correlated to the vacuum pump capacity. The specified capacity is the minimum required to attain the stated oxygen production. In some embodiments, a vacuum pump with higher capacity may be used in a disclosed system.

Figure 8A:
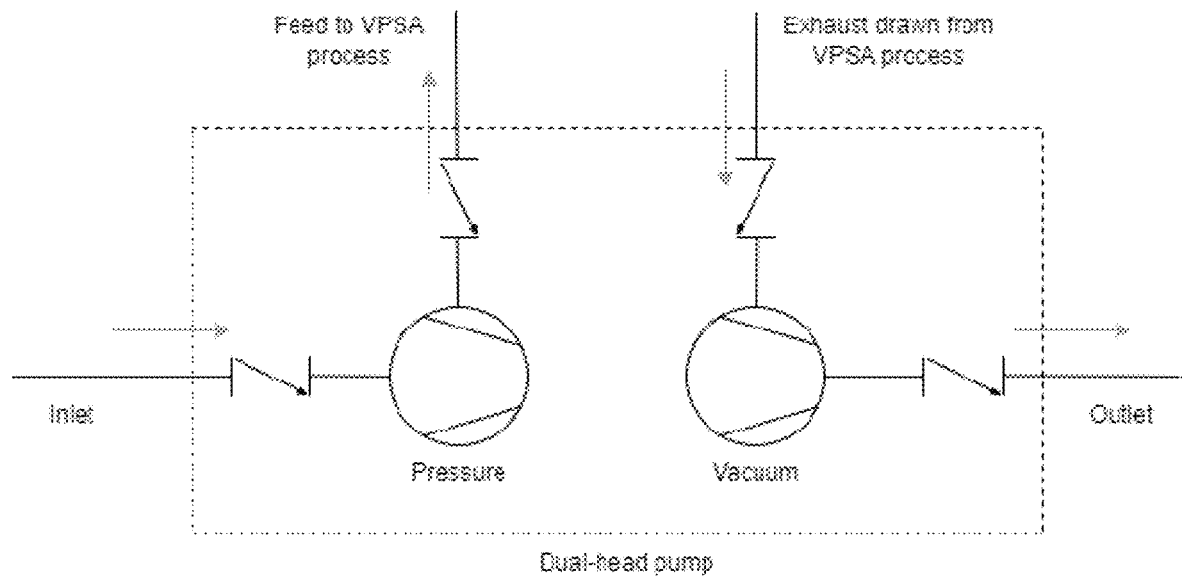
FIG. 8A depicts an exemplary setup using the dual-head pump as two separate pumps for pressure and vacuum.
Figure 8B:
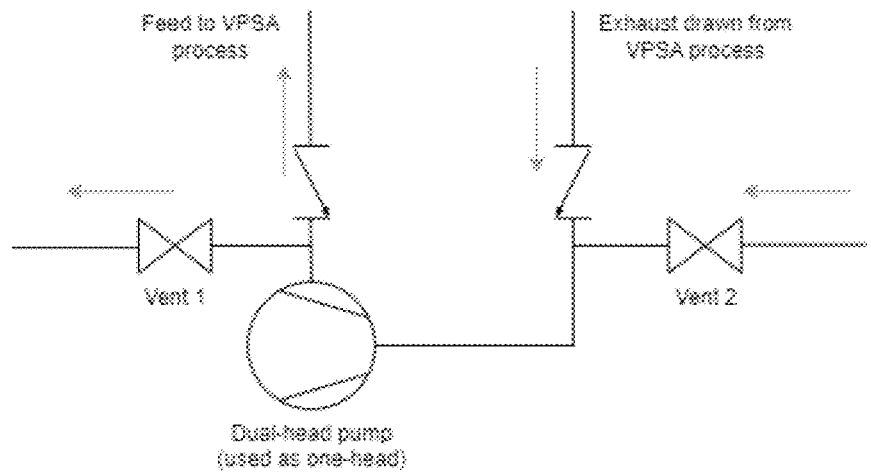
FIG. 8B depicts an exemplary setup of using the dual-head pump as one pump that provides either pressure or vacuum at any given time.

In some embodiments, as shown in FIGS. 8A-8B, the oxygen concentrator system may be configured to use a single pump that provides both positive pressure flow and vacuum exhaustion. A suitable pump needs to be selected to accommodate the needs of pressure and vacuum capacities. The step sequence needs to be adjusted so that the pressurisation and vacuum steps do not overlap. The use of a single pump allows for the portable device to become smaller, lighter, and more energy efficient. Three examples of incorporating the dual-head pump in a disclosed oxygen concentrator system are introduced.

FIG. 8A depicts an exemplary setup using the dual-head pump as two separate pumps for pressure and vacuum. In this case, one head of the pump is used to provide pressurised gas for the oxygen concentrator system (with inlet connected to the ambient environment to take in fresh air); the other head of the pump is used to provide vacuum suction to extract waste gas from the oxygen concentrator system (with waste gas vented through the outlet, which is connected to the ambient environment). In this setup, the pressure and vacuum side are completely separated and do not interfere with each other. Therefore, the dual-head pump supplies pressure and vacuum at the same time.

FIG. 8B depicts an exemplary setup of using the dual-head pump as one pump that provides either pressure or vacuum at any given time. The dual-head pump is used as a single pump, where two inlets are connected as a single inlet (which draws exhaust gas from the oxygen concentrator system); and the two outlets are connected as a single outlet (which delivers pressurised gas to the oxygen concentrator system). At any given moment, the pump is either providing pressurised gas or vacuum, but not at the same time. The sequence of cyclic phases has to be designed in such a way that the pressurisation phase and the vacuum phase do not overlap. In order to prevent the waste gas being recycled into the oxygen concentrator system, two valves are implemented to communicate with the ambient environment. When the pump is used to deliver pressurised gas, as shown in FIG. 5B, Vent 2 valve is open to allow introduction of fresh air into the process. When the pump is used for vacuum, Vent 1 valve is open to allow extraction of waste gas from the process. There may be benefits to overlap pressurisation and vacuum for a short period of time at the beginning of the vacuum phase, while closing both Vent 1 and 2 valves. The adsorbent column that undergoes vacuum still has relatively high pressure during this narrow period of time. The exhaust gas may have relatively high purity and could potentially be pressurised and recycled into the alternative column. The overlapping phase could serve as a secondary equalisation step, or even could replace the equalisation step or/and the purge step.

In another embodiment, a single dual-head pump may be used to provide pressure or vacuum at any given time, coupled with a single adsorbent column. The setup is the same as that illustrated in FIGS. 1 and 3, but instead of two adsorbent columns, only one is used in the oxygen concentrator system. Because of the single pump set up, the pump may only provide pressure or vacuum at any given moment. This means one column has to be in an idle mode when the other column undergoes pressurisation or vacuum, which results in a cycle time longer than otherwise necessary. The issue is addressed by using a single column instead of two. As disclosed herein, the purge and equalisation may be performed using oxygen tank gas rather than gas from the alternative adsorbent column. Therefore, the oxygen concentrator system is completely operable with a single column and an oxygen tank. The advantage of single column includes reduction of device size and weight, and simplified manufacture.

Consistent with disclosed embodiments, the oxygen concentrator system includes a vacuum storage tank 106 to store the vacuum capacity during periods when the vacuum pump 104 is not connected to the system and it is in idle mode. The vacuum storage tank 106 may enhance the level of vacuum achievable in the process, and thus may increase the production. During the blowdown step, the vacuum pump may be connected to a vacuum storage tank when it is not connected to either of the columns. During the vacuum step, the vacuum storage tank is connected to the column together with the vacuum pump. Testing indicates that the use of the vacuum storage tank 106 as a reservoir to conserve vacuum capacity improves process efficiency. For example, test results show that use of a vacuum storage tank with a size of 15-30 $cm^3$ produces an additional 10-20 std $cm^3$/min of oxygen.

In some embodiments, similar to the use of the vacuum storage tank, a pressure buffer may be connected to the pressure pump when it is not connected to either of the columns during the vacuum release step. The gas stored by the pressure buffer may be directed into the column during the pressurisation step to help increase the process pressure. It is contemplated that in some embodiments (e.g., when the pressure pump has significantly less capacity than the vacuum pump), the use of a pressure buffer may increase the adsorption pressure by recycling the pressure pump capacity. In some embodiments, the size of the pressure buffer may be 10-20 $cm^3$. In some embodiments, as will be described later, the pressure buffer may be configured to include an adsorbent, such as zeolites. The vacuum release step typically takes 0.1-1.0 second, which is the required time to bring vacuum pressure up to ambient pressure by connecting the column to the surrounding environment. Given the pressure pump capacity, the air delivered during this period is 25-250 $cm^3$. The size restriction of a portable and/or ambulatory device means that it may be advantageous for the pressure buffer to include adsorbent to increase the stored gas volume. If the adsorbent selectively adsorbs $N_2$ (such as Li-LSX zeolite), the system configuration may be modified to supply oxygen into the column and vent the waste $N_2$. For example, a valve connecting the pressure buffer to the surrounding environment may be provided. This valve may be closed when the pressure buffer is being charged up by the pressure pump and may remain closed for some time after the charge phase, so that the pressure buffer supplies gas (oxygen-enriched air) into the column, assisting in increasing the adsorption pressure. As the pressure buffer gradually loses its pressure, the oxygen concentration within it will decrease. When it is below some pre-determined threshold (e.g., around 21%), the pressure buffer may be cut off from the columns and the valve may be opened to release the remaining gas ($N_2$-enriched air) to the surrounding environment. In this way the pressure buffer may operate similar to an adsorbent column. Alternatively, the adsorbent in the pressure buffer could be a material that adsorbs $N_2$ and $O_2$ (e.g., non-selectively).

In some embodiments, the process gas may be used as a coolant, including the feed air and the vented waste $N_2$. In some embodiments, feed air and vented $N_2$ may be directed by a cooling fan to cool down the pumps before entering the process or leaving the device. In some embodiments, the disclosed device may not include a cooling fan. Depending on the cooling efficiency, a separate fan may or may not be needed.

In some embodiments, an oxygen tank may provide oxygen when oxygen delivery may not otherwise be provided from the columns during the process. An oxygen tank that may be injected with high-purity product gas, such as oxygen, may be configured with an oxygen tank pressure between, e.g., 1.8 to 2.5 bar and with a size of, e.g., 45-60 cm$^3$. It is found in the tests that maintaining the oxygen tank pressure slightly higher than the equalisation pressure ($P_{EQ}$) is beneficial. Specifically, this approach preserves the high-purity gas contained within the oxygen tank during the equalization process, preventing it from flowing into the column and subsequently being vented as waste. In some embodiments, at the start-up of the oxygen concentrator system, there is a transient state when the oxygen purity in product gas slowly goes up until it reaches a steady state, for example, 90% purity over a typical transient time of 5-10 minutes. Use of an oxygen tank at the start-up phase may significantly shorten the transient state to 30-60 seconds, or to 3-6 cycles. In some embodiments, the vacuum pump 104 may be used to pump down the columns 110, 120 to a sub-atmospheric pressure prior to shutdown of the system 100. Tests indicate that pumping down the columns prior to shutdown increases the efficiency of the system (e.g., by enhancing the residual $N_2$ desorption) during a subsequent start-up.

Consistent with disclosed embodiments, the production gas flow is initiated only when column pressure exceeds oxygen tank pressure. There is a brief period such as, for example, 0.1 s to 3.0 s in each cycle that the oxygen tank pressure is above column pressure, and thus does not receive product supply from the oxygen concentrator system. If a pulse oxygen delivery occurs during this period, for example, triggered by the user breathing, the oxygen tank must be capable of sustaining the bolus volume required, which is 30-50 cm$^3$/breath. If a continuous oxygen delivery is required, the oxygen tank must be capable of sustaining the continuous oxygen flow during this period. The oxygen tank pressure should not drop below the minimum oxygen tank pressure, such as 1.8 bar as disclosed herein, after the bolus volume is withdrawn. On the other hand, the selection of oxygen tank volume needs to take into account the size of a portable device.

In some embodiments, pressure equalisation may be conducted using the product gas in the oxygen tank, rather than the gas directly from the alternative column. In this way, equalisation may be performed via the purge valve (V9 in FIG. 1). Equalisation using the oxygen tank gas and using gas from the alternative column achieves a similar effect. This approach may reduce the number of valves needed, as the equalisation valve (V8 in FIG. 1) may be removed.

Columns

Figure 9A:
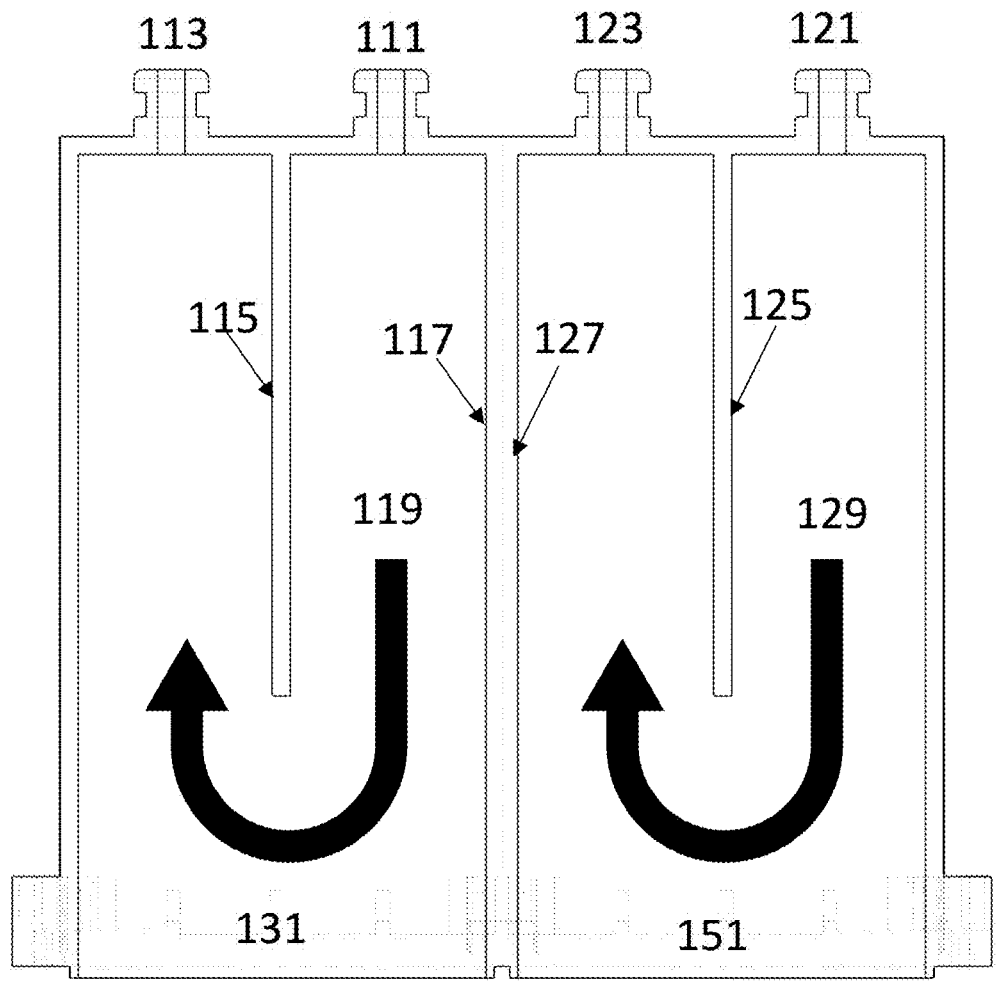
FIGS. 9A and 9B depict a cross-section view of an exemplary U-shaped column of an exemplary oxygen concentrator according to the embodiments of the current disclosure.
Figure 9B:
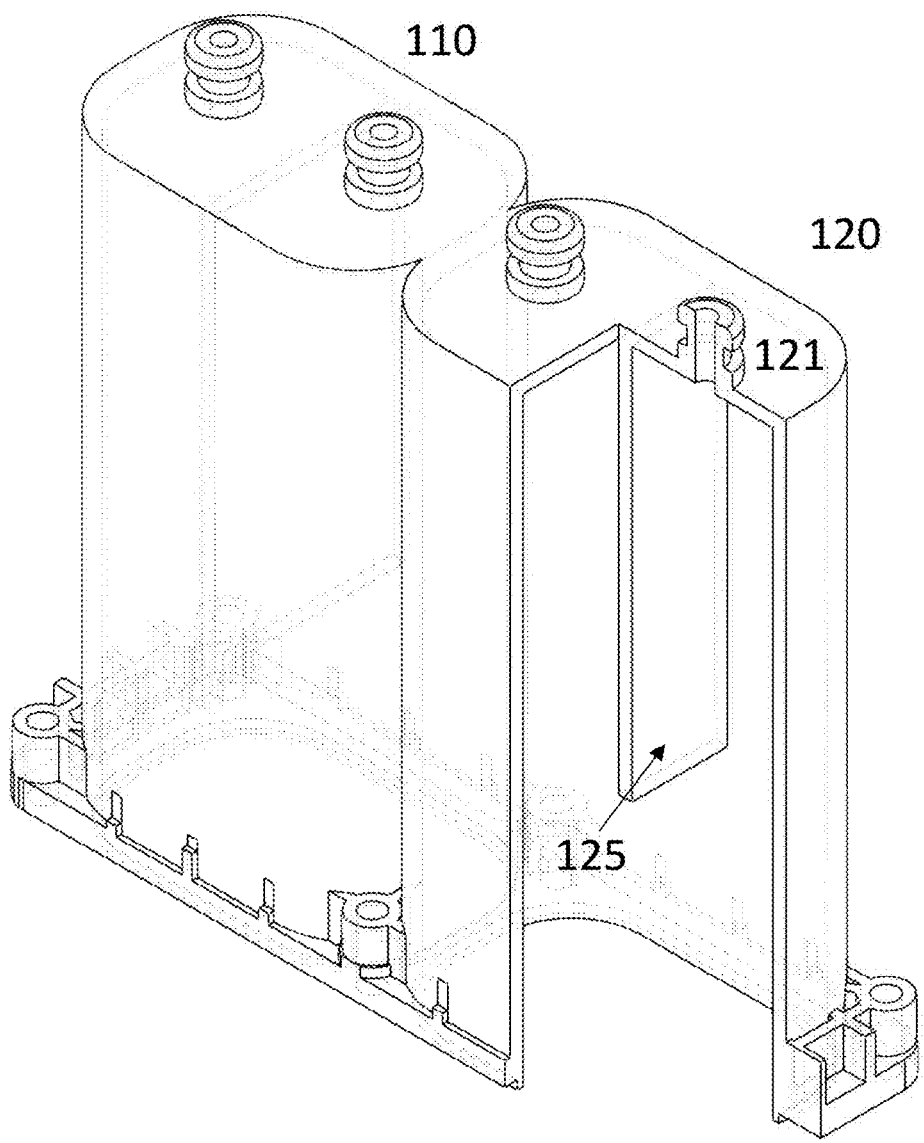

In some embodiments, as shown in FIGS. 9A and 9B, the columns 110 and 120 may be rounded-rectangular shape with a length-to-hydraulic diameter (L/D) ratio of about 3.5. Packed-bed adsorption columns may be typically cylindrical in large-scale adsorption processes. This is because a cylindrical shape offers a high surface-area-to-volume ratio, which allows for more efficient transfer of mass between adsorbent and fluid. However, in the case of compact miniature devices (such as the disclosed devices), integrating columns with curved surfaces in close proximity to other components may be difficult. As a result, use of rounded-rectangular column shapes better balances the need for efficient mass transfer and compatibility with other components in a miniature device. Further, the volume of the columns may be in a range of 95 to 100 cm$^3$. Column volume may be heavily dependent on the amount of zeolite adsorbent required in each column. The stated volume may be enough to contain the desired amount of zeolite together with other necessary componentry inside the column. In addition, the stated volume may be feasible for a portable device.

In some embodiments, the product end of the column (also referred to as column closure) has a protruding cylindrical extension that allows for easy insertion and removal of the column into a corresponding 3D-printed socket. In some embodiments, a cap equipped with a groove for an O-ring is used for column closure at the feed end. The O-ring is compressed when the end cap is screwed onto the column body, creating a tight seal. The columns need to hold at least 3.0 bar for safe operation of the process. An endcap may be smaller and lighter compared to other types of column closures, such as flanges. The above description is with reference to a column having a tube configuration which has one side feed end and the other side product end (not shown). The U-shaped column of FIGS. 9A and 9B have two protruding cylindrical extensions on one side for both feed (111/121) and product (113/123), while the column is "closed up" on the other side by the groove-cap.

The columns include a product-end extension, which is positioned at the centre of the column end face to ensure the uniform distribution of the fluid. The diameter is 2 to 4 mm. The diameter of the extension should be maximised to the greatest extend possible to prevent any restriction on flow pathway.

FIG. 9A and FIG. 9B depict an exemplary U-shaped dual column 110 and 120, consistent with disclosed embodiments. Each column includes at least two openings, an inlet and an outlet, on the top of the column. The inlet (111, 121) may be configured to guide the flow of gas into the column and the outlet (113, 123) may be configured to guide the flow of oxygen enriched gas out of the column. Each column also includes a panel (115, 125) configured to separate the column and guide the gas flow from one side of the panel to the opposite side of the panel to outlet (113, 123) through an opening (passage or clearance) at the bottom of the panel. With reference to FIG. 9A, adjacent columns 110 and 120 may have separate walls 117, 127 or the two columns may share a single wall.

Consistent with the disclosed embodiments, U-shape columns may be used to increase the length-to-diameter (L/D) ratio achievable in a portable device. A higher L/D ratio generally has negative impact on product production, as it may result in higher pressure drops across the columns. However, in a portable device where flow regime is predominantly laminar, column pressure drop is insignificant due to the short column length and relatively low flowrate compared to large-scale process. In this case, it is suggested that using a column with higher L/D ratio results in higher oxygen recovery.

In some embodiments, the oxygen concentrator system may be configured to include three or more columns. Each cycle in the oxygen concentrator system has 3 steps regarding the column feed end, pressurisation, vacuum, or connecting to ambient pressure (blowdown and/or vacuum release). It may be beneficial to have 3 columns to synchronise with each phase.

Adsorbent

In some embodiments, the adsorbent used in the columns are zeolite Li-exchanged low-silica X type (Li-LSX) zeolite, with the ratio of Si over Ai equal to 1. Li-LSX has high $N_2$ adsorption capacity and high selectivity of $N_2$ over $O_2$. It is widely acknowledged as a superior option obtainable in the portable oxygen concentrator market. Furthermore, the particle size of Zeolite is 300 to 600 µm. The particle size of zeolites is selected to ensure sufficient surface area, reasonably tight packing, and convenience of manufacture. In some embodiments, zeolite adsorbent may be sieved via a sieving process prior to being assembled into the columns, which may improve the uniformity of zeolite particle sizes. Using zeolite particles with a narrower range of sizes, as well as larger sized particles (over 400 µm), may reduce the column pressure drop by 15 to 20%, which may have a positive impact on oxygen production.

In some embodiments, the volume of zeolite is in the range of 55 to 65 grams per column, which is 110 to 130 grams in total when there are two columns. The selection of zeolite volume is correlated to several factors: 1) the size and shape of columns. Adequate bed length is necessary to avoid $N_2$ breakthrough in each cycle. On the other hand, column size needs to be feasible in a portable device. 2) The pressure and vacuum pump capacity. The volume of zeolite per column determines the volume of feed air required to pressurise the column to the desired adsorption pressure, and the volume of waste gas that needs to be withdrawn to reach the desired desorption pressure. Zeolite is filled into the columns using the following procedures: 1) pouring zeolite particles in layers, while vibrating the columns to ensure uniform distribution; 2) after the column is fully filled, consolidate the column by tapping the bed to settle the particles. The process is developed to achieve tight packing of zeolite particles, for the purpose of preventing fluidisation of the particles during pressure swing adsorption.

In some embodiments, product storage tank 130 and/or product buffer 510 may include the same type of zeolite as included in the adsorbent columns. In some embodiments, the columns, the product storage tank and/or the product buffer may include different material from each other.

Other than zeolites, different materials may include one or more of carbon molecular sieve, graphite, activated carbon organic frameworks (COFs) and metal organic frameworks (MOFs). In some embodiments, the columns, the product storage tank, and the product buffer may include hydrogen-bonded organic frameworks (HOFs) as a type of adsorbent to produce production gas and increase storage capacity. HOFs are a type of polymeric porous material that may be self-assembled through H-bonding between organic linkers. H-bonding may have unique properties including being weak, flexible, poorly directional, and reversible. These unique properties may give HOFs distinct advantages, such as ease of solution processing and characterization, simple purification, and the ability to heal through recrystallization, over materials like zeolites, MOFs, and COFs.

Additionally, HOFs may be highly selective towards oxygen over nitrogen and argon. As a result, it may be used for a second stage pressure swing adsorption to further purify the oxygen product. In some embodiments, HOFs are hydrophobic. Therefore, the adsorption capacity of HOFs is not affected by humidity present in room air. As such, replacement of columns and product buffer is not required due to the absence of moisture induced degradation.

Bottom and Top Manifolds

Figure 10A:
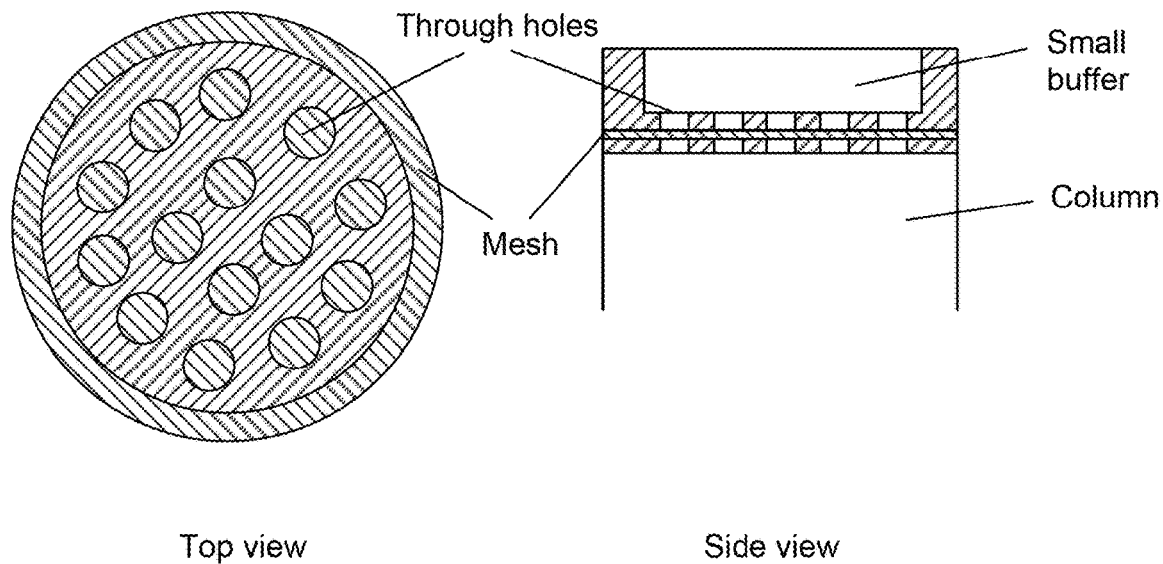
FIG. 10A depicts a column top filter piece incorporating a filter component, that may be used in exemplary oxygen concentrators, according to the embodiments of the current disclosure.

As shown in FIGS. 10A, the column top filter piece may incorporate a filter component that is the same shape as the column cross section, featuring an integrated mesh structure centrally printed within. The mesh may have a hole size smaller than the zeolite particles used (<200 µm), and therefore may act as an air-permeable barrier to prevent the zeolites from leaking out of the column. The filter component has larger holes (2-5 mm) to restrict flow as little as possible. Using a small buffer on top of the filter piece minimises pressure drop. In some embodiments, a material (e.g., a filter sheet/membrane) that's an electrostatic and hydrophobic polypropylene material, may also be used as a filter. An ideal filter should provide no (or minimal) pressure drop, allow free flow of air, and filter out zeolites. Testing indicates that filter sheet/membrane to be most effective. Advantages of such a material include easy to cut and place as it's a sheet of material without having to worry of tolerance problems as opposed to an O-ring design filter. Further, these filter sheets are also used as Bacterial/Viral Mouthpiece Filters.

Figure 10B:
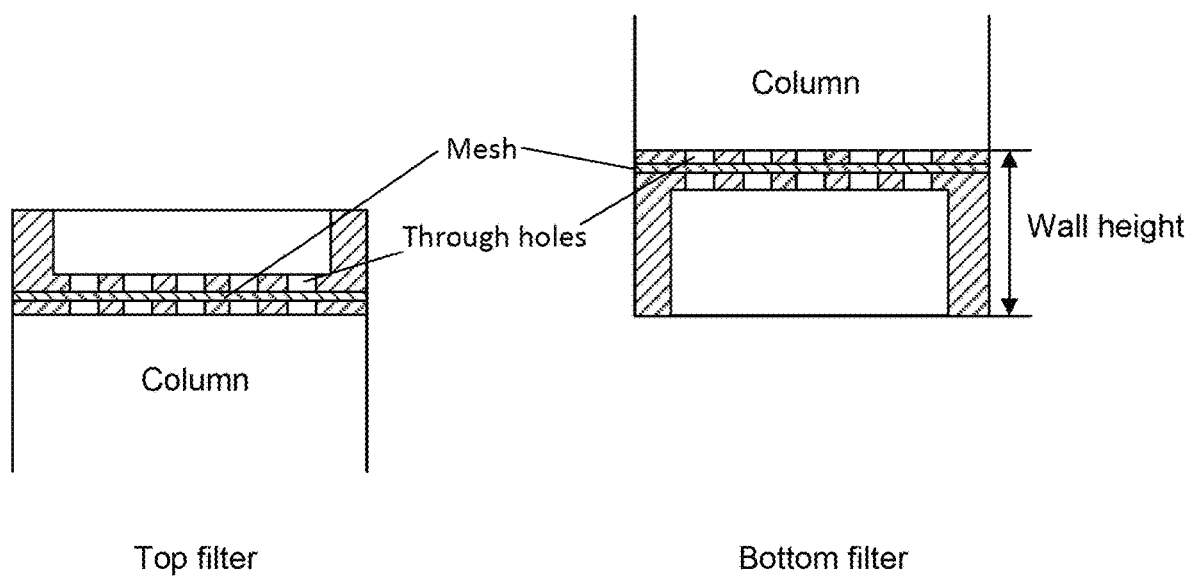
FIG. 10B depicts wall height differences between a top filter piece and a bottom filter piece that may be used in exemplary oxygen concentrators of the current disclosure.
Figure 10C:
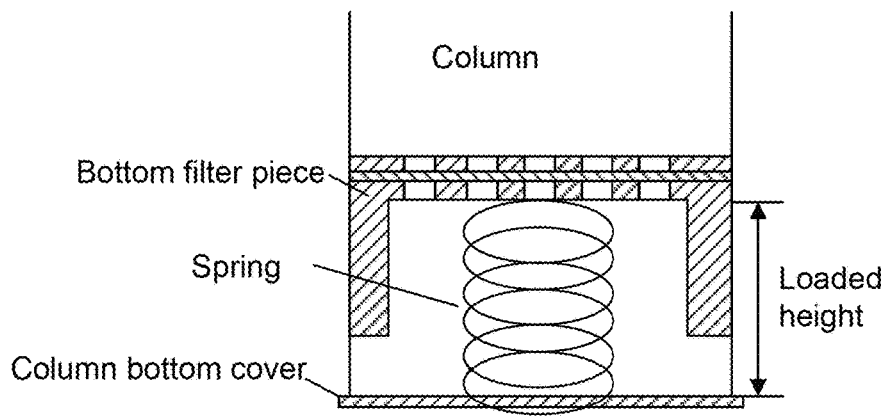
FIGS. 10C and 10D depict a cross-section view of a spring installed between a bottom cover and a bottom filter piece, according to the embodiments of the current disclosure.
Figure 10D:
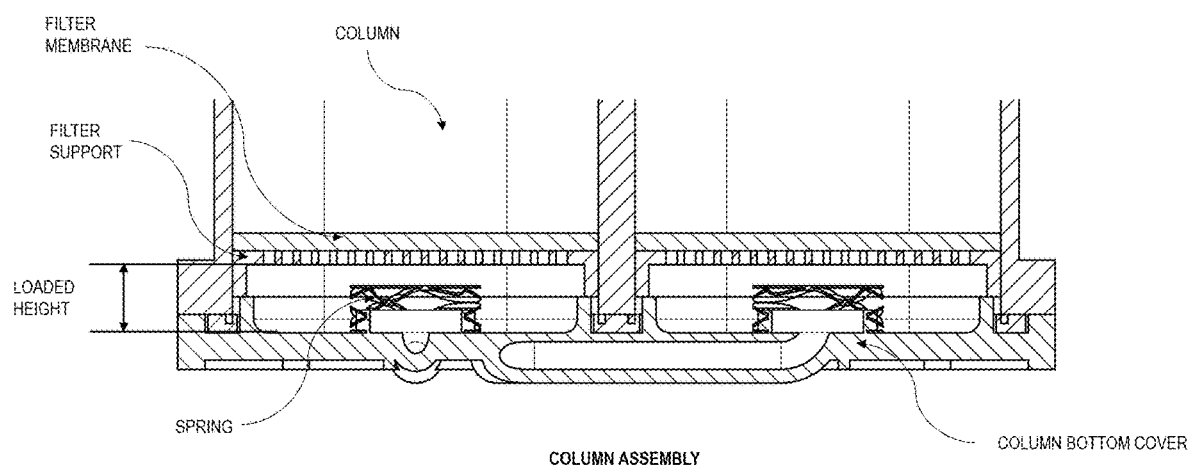

As shown in FIGS. 10B, 10C, and 10D, the bottom filter piece may be similar to the top filter piece having a filter component that is the same shape as the column cross section. The bottom filter piece may have a greater wall height, the greater wall height (the taller wall) may inhibit the tilting of the filter component during installation. For example, the filter wall may align the filter piece to the column inner wall, and a longer wall may make the alignment better and reduce the possibility of the filter tilting and getting stuck. Further as shown in FIGS. 10C and 10D, a spring may be installed between the bottom cover of the column and the bottom filter piece. The spring keeps the bottom filter in place and applies a compressive pressure on the zeolite packed bed to prevent fluidisation. The loaded height of the spring needs to match the distance between the column bottom cover and bottom filter piece.

In some embodiments, as shown in FIG. 1, the oxygen concentrator system may include six C15 solenoid valves at the feed end of the columns to allow pressurisation using the pressure pump (V1 and V4), blowdown (exhaust) to ambient pressure (V3 and V6), and depressurisation using the vacuum pump (V2 and V5). In some embodiments, the oxygen tank and the four check valves (CV2, CV3, CV4, and CV5) may be integrated together as one component. The integrated design of the oxygen tank and check valves may reduce device size and weight, as well as minimise the end-space void volume. The end-space void volume, which is a void volume at both feed end and product end of the columns, should be minimised to the greatest extent possible. Feed end-space voids result in gas being compressed but not processed through the column, thereby decreasing oxygen recovery and increasing power consumption. Product end-space voids contain product gas that is not delivered to the user and may be vented when column pressure drops.

In some embodiments, the oxygen concentrator system may include a plurality of control valves, while in other embodiments the number of valves may be reduced by using suitable bi-directional, 2-way, 3-way, 4-way or rotary valves, and by combining some of the flow channels. Using fewer valves may reduce the size, weight, and power consumption in a portable device.

In general, the control valves may have any size. In some exemplary embodiments, the control valves have an orifice size over about 1.5 mm. The disclosed handheld oxygen concentrator system operates with fast cycles (e.g., 5-12 seconds). In some embodiments, the pressurisation and/or depressurisation may take less than 4 seconds to complete. Therefore, it is advantageous to have minimum flow restriction across the control valves to accommodate higher gas speed, especially for valves at the column feed end, which handle larger amounts of gas. Test results suggest that use of control valves with larger orifices and/or shorter cycle time are possible and may lead to more oxygen production.

Consistent with some exemplary disclosed embodiments, the response time of the control valve is less than about 10 ms. A quick response of the control valves may result in reduced delay when switching gas direction. Due to the nature of the short cycle time, consistent delays in each cycle accumulate quickly over time and may interrupt cycle operations.

In some embodiments, inner diameter of the tubing or connector pieces may be over about 2 mm. In some applications, a tubing wall thickness of greater than about 1 mm may avoid kinking. As explained previously, it may be advantageous to have reduced flow restriction along the flow channels. To achieve low restriction, in some embodiments, the inner diameter of tubing/connector may be larger than the size of the control valve orifice. The lengths of the tubing/connector may also be limited in order to minimise pressure drops. In some embodiments, it may be desirable to have a circular cross-section for both the tubing and the connector pieces. Circular cross-sections may provide uniform flow distribution and better prevent turbulent flow compared to other shapes. Circular tubing/connectors may also be cost effective as they are readily available in market. In general, shorter and wider tubing/connectors may be preferable over longer and narrower pieces to reduce flow restriction. The selection of size and length should aim to minimise pressure drop across the tubing/connectors.

The recovery, which is defined as the ratio of product oxygen over feed oxygen, describes the effectiveness of utilising the feed flow and is an important parameter in adsorption process. Due to the constraint in size and maximum adsorption pressure, recovery is typically 30-35% in portable oxygen concentrators. The disclosed oxygen concentrator system as disclosed herein is able to achieve recovery of 54%.

$$\text{Recovery} = \frac{(y_{O_2} \times Q)_{product}}{(y_{O_2} \times Q)_{feed}}$$

Another important characteristic of the adsorption process is bed size factor (BSF), which describes the effectiveness of utilising the adsorbent (e.g., zeolite). BSF is defined as the ratio of adsorbent weight over product weight, as shown in the equation below. A smaller BSF indicates a more efficient use of adsorbent.

$$BSF = \frac{W_{adsorbent}(\text{in lbs})}{w_{O_2\ product}(\text{in tons of } O_2 \text{ produced per day} - TPDO)}$$

At an industrial scale, a BSF for high recovery (e.g., BSF corresponding to 50-60% oxygen recovery) is typically around 350 lbs/TPDO. During prototype benchtop testing, a disclosed system achieved a BSF of 140 lbs/TPDO and was overall more efficient both in the use of feed flow and adsorbents (zeolites). To achieve the same amount of oxygen production as a conventional PSA process, embodiments of the disclosed oxygen concentrator devices may: 1) use a lower adsorption pressure-meaning that it is not necessary for the column material and connection joints to be pressure-rated as high as required by a PSA process; 2) use a lower feed flow-meaning the pressure pump may be smaller, lighter and consumes less power; 3) the adsorbents are exposed to less contaminant (mainly moisture and $CO_2$ in the feed air), therefore column life time is longer; and 4) use fewer zeolite particles, meaning smaller columns may be used and the device may weigh less.

Pressure Buffer and Product Buffer with Adsorbent

In some embodiments, the pressure buffers and gas storage tanks (e.g., product storage tank 130 as shown in FIG. 1, product buffer 510 as shown in FIG. 5A, etc.) of the disclosed oxygen concentrators may include an oxygen-adsorbent material to increase the storage capacity of the gas in the tank. In the case of the product storage tank 130 as shown in FIG. 1, the gas that goes into the buffer is product gas from the adsorption process (e.g., oxygen at a selected purity-87%-95%, etc.). Therefore, any adsorbent material that may adsorb oxygen may be provided in the tank 130. In general, the amount of adsorbent in the tank may depend on the application. In some embodiments, the tank (e.g., product storage tank 130) may be filled with the adsorbent to maximize gas storage. Non-limiting examples of adsorbents that may be provided in the storage tank 130 include: various types of zeolites; LiLSX-which is the zeolite typically used in oxygen concentrator columns; LiX; NaX; NaA; other zeolite that adsorbs oxygen; metal organic framework that adsorbs oxygen; hydrogen-bonded organic framework that adsorbs oxygen; molecular sieves; activated carbon, silver and copper bases adsorbents, perovskite oxides, polymeric membranes, zirconium-based adsorbents, etc.

Similarly, in the case of the product buffer 510 as shown in FIG. 5A, the gas that goes into the buffer is product gas from the adsorption process (e.g., oxygen at a selected purity—87%-95%, etc.). Therefore, any adsorbent material that may adsorb oxygen may be provided in product buffer 510. In general, the amount of adsorbent in product buffer 510 may depend on the application and may be a plurality options to the user during the replacement of removable module 150. In some embodiments, product buffer 510 may be filled with the adsorbent to maximize gas storage. Non-limiting examples of adsorbents that may be provided in product buffer 510 include: various types of zeolites; LiLSX-which is the zeolite typically used in oxygen concentrator columns; LiX; NaX; NaA; other zeolite that adsorbs oxygen; metal organic framework that adsorbs oxygen; hydrogen-bonded organic framework that adsorbs oxygen; molecular sieves; activated carbon, silver and copper bases adsorbents, perovskite oxides, polymeric membranes, zirconium-based adsorbents, etc.

It should be noted that the terms "tank," "storage tank," "product storage tank," and "product buffer" may be interchangeable and may serve the same function and the same design. In some embodiments, a portable oxygen concentrator may only include a product buffer in the main body of the portable oxygen concentrator. In some embodiments, a portable oxygen concentrator may include a product buffer in the main body of the portable oxygen concentrator and a product buffer in a removable module. In some embodiments, a portable oxygen concentrator may only include a product buffer in a removable module. The number and placement of product buffers may be tailored to meet the user's requirements.

As the pressure in the product buffer fluctuates between the highest and the lowest buffer pressure (Pb-max and Pb-min), its storage capacity depends on the oxygen adsorption capacity of these two pressures.

$$\Delta V = (C(P\_(b\text{-max})) - C(P\_(b\text{-min})))m$$

Where C(P) is the adsorption capacity at pressure P (in ml/g), m is the mass of the adsorbent that is put into the product buffer, and $\Delta V$ is the buffer storage capacity. In the case of our disclosed process, Pb-max is slightly lower than the process adsorption pressure $P_{ads}$ (about 2.2 bar) and Pb-min is usually slightly lower than the column pressure when purge step starts (about 1.8 bar).

When using LiLSX and 5A zeolite to fill the product storage tank 130 during benchtop testing, the storage capacity of the tank 130 was found to be 2-2.5 times that of an empty buffer. As a result of the increased storage capacity, a much smaller buffer (40-50% of its original size) may be used to achieve the same amount of gas storage. This makes the disclosed oxygen concentrator smaller and lighter. Product storage tank 130 is used to supply the user with product gas when the adsorption process is still approaching steady state, or (in the case of pulse delivery) when the process is not able to maintain the high flowrate required in that instant. For a fixed-size buffer (e.g., tank 130), the presence of adsorbent allows a longer period of product gas supply. The cyclic nature of pressure swing adsorption means that the product gas flowrate fluctuates in each cycle. The storage tank 130 smooths the gas delivery and potentially allows the elimination of an electronic valve for controlling the product flowrate. The humidity level in the product gas is very low (<1% relative humidity) as the gas has passed through the whole adsorbent column in which moisture is removed. As a consequence of this, the adsorbent inside the storage tank 130 undergoes minimum contamination over time, which means minimum effort of maintenance or replacement of the tank is required over the lifetime of the oxygen concentrator.

It should be noted that, although the use of adsorbent in a gas storage tank is described with reference to the product storage tank 130 (or product buffer 150) of an oxygen concentrator, it is not so limited. In general, an adsorbent may be provided in a gas storage tank used in any application that requires temporary gas storage. Gas storage tanks are used in a wide range of applications across various industries. These tanks are designed to store gases in a compressed or liquefied form for later use. Some non-limiting applications where gas adsorbents may be included in gas storage tanks include: oxygen tanks used in healthcare (e.g., to provide supplemental oxygen to patients); industrial gas storage (e.g., storage tanks that store, e.g., nitrogen, hydrogen, helium, and argon for welding, cutting, and various other industrial processes); LPG tanks that are commonly used in residential and commercial settings for storing propane and butane gases (e.g., for heating, cooking, and powering appliances); cryogenic tanks used to store gases (e.g., liquid nitrogen, liquid oxygen, and liquid hydrogen) at extremely low temperatures; underground natural gas storage tanks or caverns that store natural gas for distribution to homes and businesses; compressed air tanks that are used in various applications (e.g., including pneumatic tools, scuba diving, and industrial processes) that require a consistent source of compressed air; hydrogen storage tanks are used in fuel cell vehicles; acetylene storage tanks; $CO_2$ tanks used for a variety of applications (e.g., including carbonation of beverages, firefighting, etc.); anhydrous ammonia tanks that are used in agriculture to store and transport ammonia (e.g., for use as a fertilizer); gas storage cylinders or tanks that store various specialty gases (e.g., calibration gases for laboratory equipment, etc.); emergency breathing air tanks that provide a supply of breathable air for workers in emergency situations; gas storage tanks that store propulsion gases, life support gases, and scientific instrument gases in space exploration applications, etc.

In each of these gas storage tanks, an adsorbent configured to adsorb the gas stored in the tank and is suited for the application may be provided. For example, in an oxygen tank, an adsorbent that adsorbs oxygen (e.g., zeolites, molecular sieves, activated carbon, silver-based adsorbent, copper-based adsorbent) may be provided, and in a nitrogen tank, an adsorbent that adsorbs $N_2$ (e.g., zeolites, molecular sieves, carbon molecular sieves, polymeric membranes, metal-organic frameworks, carbon nanotubes, silica gel, etc.) may be provided. In some embodiments, the adsorbent used in the gas storage tank may not change or affect the composition of the gas stored in the tank. In other words, the composition of the gas entering the tank and the composition of the gas exiting the tank may be substantially the same. The amount of adsorbent provided may depend on the application. In some embodiments, the tank may be filled with the adsorbent. In some embodiments, the tank may not be filled with the adsorbent. Instead, a smaller amount (e.g., 25%, 50%, 75%, etc., of the tank volume) may be provided. The adsorbent in the gas storage tank may increase the amount of gas stored in the tank.

Exemplary Automation Process of a Disclosed Oxygen Concentrator

Further in this application, an automating process is introduced here. The automating process may generate the optimum process parameters and control the operation accordingly. The device and its automation are not limited to the production of oxygen-they may be applied to automate any gas separation process, given use of the appropriate adsorbents and sensors. The addition of one or more automation algorithm vitalizes the portable ambulatory oxygen concentrator system and enables it to be used on the production of different gas, at different concentrations, in different applications, and with greater flexibility.

In some embodiments, the disclosed portable and handheld oxygen concentrators may be configured to receive feed air and discharge oxygenated air and may comprise a user interface, a plurality of sensors; one or more pumps (e.g., two pumps), at least two adsorbent columns, and a controller. The user interface may enable the user to interact and communicate with the portable ambulatory oxygen concentrator. The user interface may be a graphical user interface (GUI) that is an interface through which a user interacts with electronic devices such as computers and smartphones through the use of icons, menus and other visual indicators or representations (graphics). The user interface may further include display screens, keyboards, buttons, a mouse and an application or a website to send a user interacts through wireless network. The sensors may include at least a temperature sensor, a humidity sensor, a pressure sensor, a product purity sensor, a flow sensor, and other relevant sensors (e.g., $CO_2$ sensor). In some embodiments, at least one of the sensors may be a built-in sensor on the body of the portable ambulatory oxygen concentrator. In some embodiments, the sensors may not be included in the portable ambulatory oxygen concentrator, especially for the sensors measuring the atmosphere and the environment around the portable ambulatory oxygen concentrator, such as the temperature sensor, the humidity sensor, and the $CO_2$ sensor. The portable ambulatory oxygen concentrator may be configured to use a single pump that provides both positive pressure flow and vacuum exhaustion. In some embodiments, the portable ambulatory oxygen concentrator may be configured to use a pump to provide positive pressure flow, and another pump to provide vacuum exhaustion.

Figure 11:
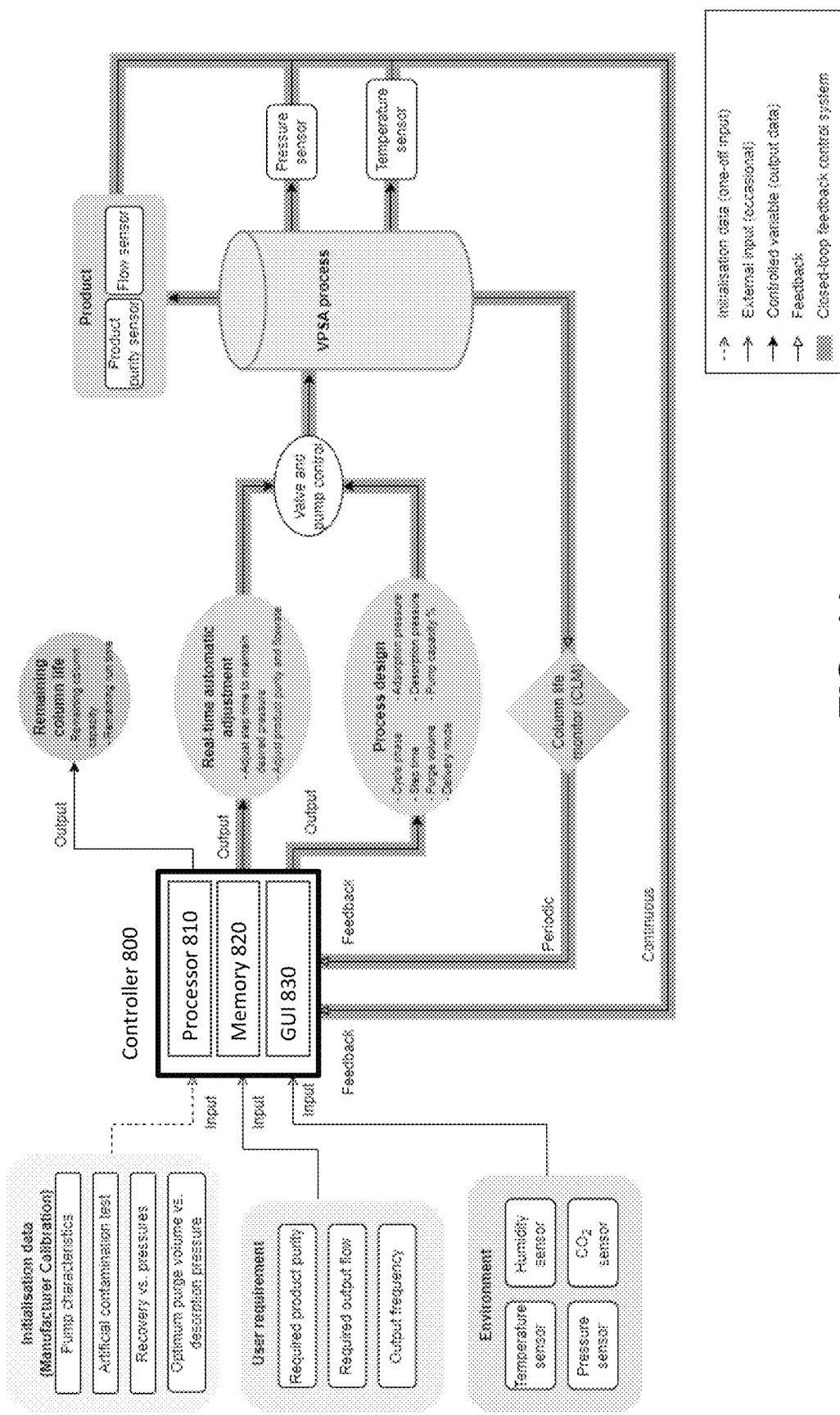
FIG. 11 depicts an exemplary flow chart of an exemplary automation process of an exemplary oxygen concentrator according to the embodiments of the current disclosure.

In some embodiments, the controller is electrically coupled to various components of the portable ambulatory oxygen concentrator, such as, a plurality of valves, a plurality of sensors, the user interface, and the pump. Methods used to operate and monitor the portable ambulatory oxygen concentrator may be implemented by programs stored in memories. As shown in FIG. 11, in some embodiments, the controller 800 may include one or more processors 810, operable to execute programs stored in one or more memories 820. The controller may further include one or more GUI 830 that may collect instructions or input from a user or a user's caregiver and display the information output by the one or more processors. In some embodiments, the controller may be associated with a non-transitory computer readable storage medium that may include instructions for controlling the operation of the portable oxygen concentrator. As used herein, a non-transitory computer-readable storage medium (or similar constructs such as a non-transitory computer-readable medium) refers to any type of physical memory on which information or data readable by at least one processor may be stored. Examples include Random Access Memory (RAM), Read-Only Memory (ROM), volatile memory, non-volatile memory, hard drives, CD ROMs, DVDs, flash drives, disks, any other optical data storage medium, any physical medium with patterns of holes, markers, or other readable elements, a PROM, an EPROM, a FLASH-EPROM or any other flash memory, NVRAM, a cache, a register, any other memory chip or cartridge, and networked versions of the same. The terms "memory" and "computer-readable storage medium" may refer to multiple structures, such as a plurality of memories or computer-readable storage mediums located within the portable oxygen concentrator or at a remote location. Additionally, one or more computer-readable storage mediums may be utilized in implementing a computer-implemented method. Accordingly, the term computer-readable storage medium should be understood to include tangible items and exclude carrier waves and transient signals.

The computer readable storage medium may contain instructions that when executed by at least one processor may cause the at least one processor to perform operations including switch valves, monitor and control the pump. The term "at least one processor" may involve any physical device or group of devices having electric circuitry that performs a logic operation on an input or inputs. For example, the at least one processor may include one or more integrated circuits (IC), including an application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory. The memory may include a Random Access Memory (RAM), a Read-Only Memory (ROM), a hard disk, an optical disk, a magnetic medium, a flash memory, other permanent, fixed, or volatile memory, or any other mechanism capable of storing instructions. In some embodiments, the at least one processor may include more than one processor. Each processor may have a similar construction, or the processors may be of differing constructions that are electrically connected or disconnected from each other. For example, the processors may be separate circuits or integrated in a single circuit. When more than one processor is used, the processors may be configured to operate independently or collaboratively and may be co-located or located remotely from each other. The processors may be coupled electrically, magnetically, optically, acoustically, mechanically, or by other means that permit them to interact.

FIG. 11 depicts an exemplary flow chart for the portable ambulatory oxygen concentrator automation process to generate improved process parameters, consistent with disclosed embodiments. In some embodiments, there may be three categories of input data: a first input including user requirements, a second input including environment conditions, and a third input including initialisation data provided by the manufacturer. The third input may be configured to initiate the automation system and may be supplied only once before the automation system starts working. Other types of input data such as user requirement and environment data, may be requested, required, and/or provided periodically.

The automation process may be configured to receive the first input data through the user interface, from at least one of a user, an operator, a clinician, or the user's care provider, and an equipment measuring the user's health parameters from the user interface. The automation process may also be configured to receive input data from a connected external device, wired or wireless, which device may also be configured to display user health parameters, sensor data, and/or the performance of the concentrator. In some embodiments, the first input includes one or more of a desired oxygen concentration in the discharged oxygenated air, a desired flowrate of the discharged oxygenated air, or a desired discharge frequency of the oxygenated air. In some embodiments, a first input data may be saved into a memory of the portable ambulatory oxygen concentrator. The saved first input data may be retrieved by the controller later.

User requirements may comprise desired inputs of oxygen concentration (e.g., 90% oxygen), output flowrate (e.g., 1 standard litre per minute (slpm), or increased or decreased flowrate), and gas delivery frequency (e.g., continuous output, or pulse output at 5 second intervals). For example, in the case of a portable ambulatory oxygen concentrator the user or clinician may state that the user needs 1 slpm of 90% oxygen, delivered in continuous output, or delivered in pulse output at 5 second interval.

The gas volume delivered in each pulse may be calculated automatically as output flowrate divided by the number of pulses in 1 minute. The user may also specify product requirements at different settings, e.g., 0.5 slpm at user setting 1, 1.0 slpm for user setting 2, and 1.5 slpm for user setting 3. A user requirement may be provided whenever the user wishes, as well as at a certain time interval, or in response to external changes (e.g., changes in humidity or reductions in external air quality). For instance, the user may be prompted to reconfirm user requirements once every week.

Consistent with the disclosed embodiments, the automation process may be configured to receive a second input from one or more of sensors of the portable ambulatory oxygen concentrator. In some embodiments, the second input may include signals indicative one or more of temperature, humidity, pressure, or $CO_2$ level in the feed air, and from the sensors of surrounding environment.

In some embodiments, the portable ambulatory oxygen concentrator constantly monitors its surrounding environment using a plurality of in-built sensors including a temperature sensor, a humidity sensor, a pressure sensor, and other relevant sensors (e.g., $CO_2$ sensor). These data may be collected mainly to obtain information on the moisture and $CO_2$ level present in feed air. The information is subsequently used to estimate remaining column lifetime.

Specifically, environment temperature may be configured to assist in predicting the real-time adsorbent capacity of the adsorbent material. Typically, adsorption capacity reduces at higher temperatures. Environment pressures may be configured to assist in predicting performance of pressure and vacuum pumps. Although ambient pressure is relatively consistent during daily activities, it could vary when the user's latitude changes, e.g., when the user travels on a plane or climbs a mountain. Ambient pressure also changes with weather changes, and in cycles through a day, with larger daily changes the closer the user is to the Equator. The presence of moisture in feed air is known to contaminate adsorbents such as zeolites over time, thus it is important to obtain data on the moisture level in feed air. Data about moisture levels could be achieved by measuring the relative humidity and temperature of the surrounding environment. Similarly, $CO_2$ in feed air is also known to be a contaminant to adsorbents such as zeolites. Data regarding $CO_2$ concentration in the environment may be configured to assist in predicting the remaining lifetime of adsorbent in columns. Environment input may be required periodically, such as once per day, whenever the device is turned on (such as through initialisation), or on changes in external conditions such as changes in the weather.

Consistent with the disclosed embodiments, the automation process may be configured to receive a third input from the pre-set manufacturer calibration data, including one or more of a pressure pump characteristic, a vacuum pump characteristic, a moisture contamination, an oxygen concentration, a recovery rate, a flow rate and a humidity.

In some embodiments, the pre-set initialisation manufacturer calibration data, may include information extracted from equipment datasheet and calibrations on adsorbent and the portable ambulatory oxygen concentrator. In some embodiments, the calibrations may be conducted manually by the manufacturer. In some embodiments, initialisation data may be generated digitally in simulations by mathematical modelling and machine learning models. In some embodiments, the pre-set initialisation manufacturer calibration data may be a one-off input supplied at initial stage. In some embodiments, the pre-set initialisation manufacturer calibration data may be updated or retrieved by the device at any time. In some embodiments, the pre-set initialisation manufacturer calibration data may be provided at any other time on the device's demand or a user request.

A controller may be configured to receive at least one of the first input data and the second input data and determine one or more of the remaining capacities of the at least two adsorbent columns and the estimated remaining run time of the at least two adsorbent columns on a display, which may be a screen, a panel, a monitor a television, or an interface. Consistent with the disclosed embodiments, the controller may receive the first input data from a user input or retrieve the first input data from the memory. The controller may be configured to receive the second input data from sensors on the portable ambulatory oxygen concentrator. In some embodiments, the controller may be configured to obtain the second input data based on average sensor data measured from a past period, such as, a day, a week, two weeks, or a month.

Consistent with disclosed embodiments, the portable ambulatory oxygen concentrator may receive a first input through the user interface from a user or a user caregiver, including one or more of a desired oxygen concentration in the discharged oxygenated air, a desired flowrate of the discharged oxygenated air, and a desired discharge frequency of the oxygenated air. Configured to combine with other data, such as one or more of sensors' data and initialisation manufacturer calibration data, the portable ambulatory oxygen concentrator may display as a first output one or more of a remaining capacity and an estimated remaining run time of the at least two adsorbent columns. In some embodiments, the user or the user caregiver may adjust the first input data through the user interface to obtain the desired remaining capacities or estimated remaining run time of the at least two adsorbent columns.

A second output may enable an automatic real-time adjustment of the portable ambulatory oxygen concentrator, which may be used to adjust the parameters, such as to reduce or eliminate any deviation from the desired value of the process variables and the production under a given operation condition. The operation condition may include pump operation, vacuum operation, switching of a plurality of valves open or close, specifically, it may include a plurality of parameters such as adsorption pressure, desorption pressure, step times, oxygen concentration and flow rate. The given operation condition, for example, may refer to maintaining a desired or predetermined adsorption pressure and desorption pressure. In some embodiments, the given operation condition may refer to a user desired oxygen concentration in the discharged oxygenated air, a desired flowrate of the discharged oxygenated air, or a desired discharge frequency of the oxygenated air input through the user interface. A third output may enable automatic process design, which permits configuration to generate optimum operation parameters upon receipt of updated user requirements.

Output parameters may be used to operate the portable ambulatory oxygen concentrator. Sensory data obtained from the portable ambulatory oxygen concentrator, including pressure, flowrate, product purity, etc., may be supplied back to the algorithm as real-time feedback. A column life monitor test (CLM) may be conducted periodically to gauge the adsorbent contamination level and may form part of the feedback data that allows the control algorithm to adjust oxygen output.

Figure 12:
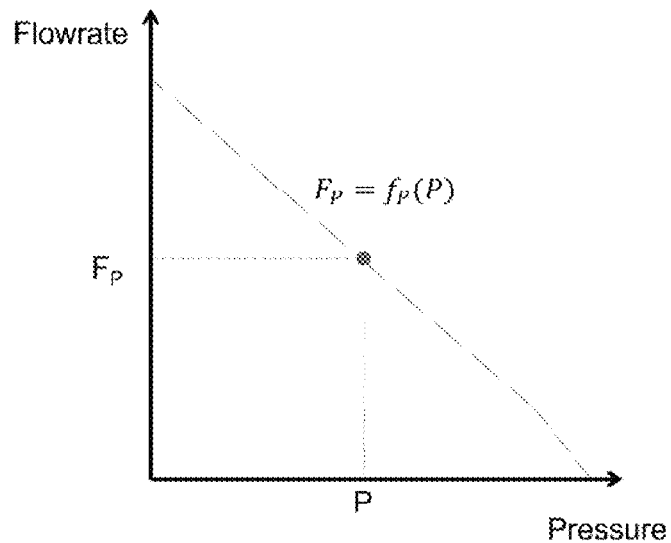
FIG. 12 depicts a pressure pump characteristic curve for a pressure pump ($f_P$), according to the embodiments of the current disclosure.

FIG. 12 depicts a pressure pump characteristic curve for a pressure pump ($f_P$), as may be obtained from the datasheet of a pressure pump manufacturer.

FIG. 12 demonstrates a correlation between downstream pressure and the flowrate that may be delivered by the pressure pump.

Figure 13:
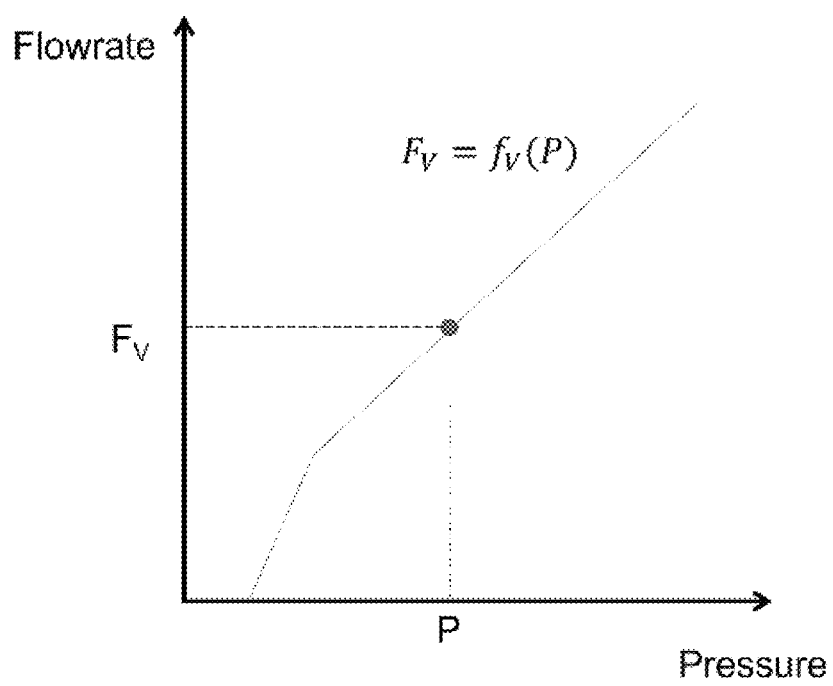
FIG. 13 illustrates a vacuum pump characteristic curve for vacuum pump characteristic ($f_V$), according to the embodiments of the current disclosure.

FIG. 13 illustrates a vacuum pump characteristic curve for vacuum pump characteristic ($f_V$), as may be obtained from the datasheet of a vacuum pump manufacturer. FIG. 13 demonstrates a correlation between upstream pressure and the flowrate that the vacuum pump may extract from the process.

Figure 14:
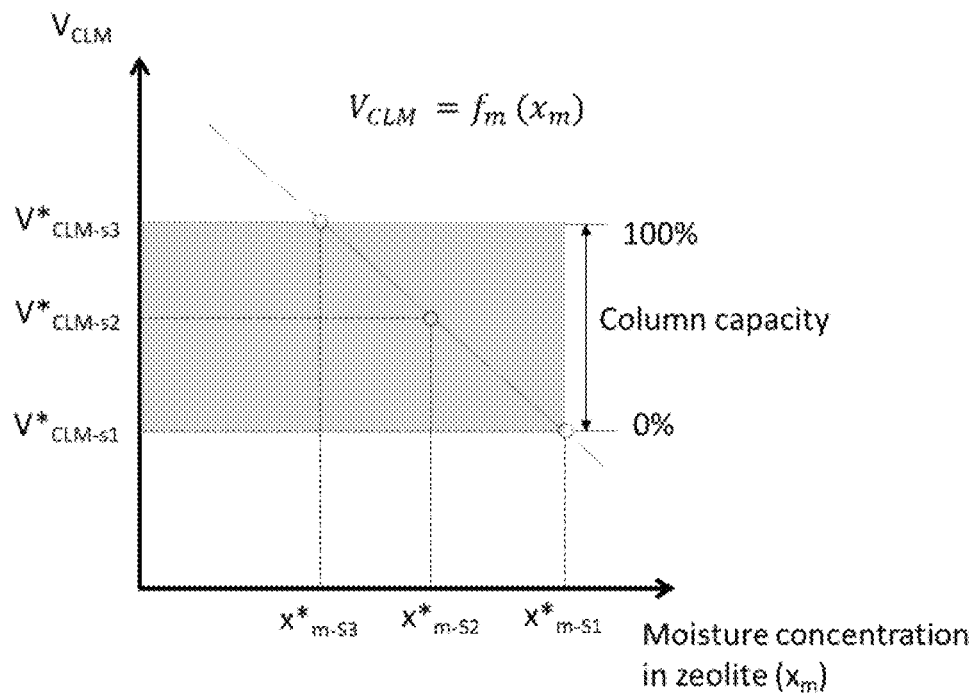
FIG. 14 depicts correlation related to moisture contamination ($f_m$), according to the embodiments of the current disclosure.

FIG. 14 depicts correlation related to moisture contamination ($f_m$), consistent with disclosed embodiments. To understand the relationship between the moisture concentration in adsorbent such as zeolite and its absorption capacity, a set of calibration experiments may be performed in which a pair of fresh columns are artificially contaminated gradually by moisture present in feed air. Column life monitor test (CLM) is then conducted on the columns at various states of contamination.

Correlation between the accumulated moisture concentration in adsorbent and the feed air volume that goes into the column in a column life monitor test ($V_{CLM}$) is illustrated in FIG. 14. A lower $V_{CLM}$ may signal a higher level of contamination, which means more moisture accumulated in the adsorbent. Moisture level corresponding to the lowest threshold product purity for user setting 1, 2 and 3 are also shown.

In some embodiments, it is preferable to obtain the moisture concentrations corresponding to the lowest acceptable product purity at set product flowrates. For example, assuming the process is running at a fixed product flowrate, the product purity gradually decreases with increasing levels of moisture contamination. When product purity ($y_{O2\text{-}PD}$) reaches the lowest threshold set by the user or clinician, the corresponding $V^*_{CLM}$ and $x^*_m$ at this moment of time should be recorded, as shown in FIG. 14.

A column capacity could be set arbitrarily in a way similar to that of a battery capacity. For example, $V^*_{CLM\text{-}S3}$ may be set as representing 100% capacity if setting 3 is the highest setting, and $V^*_{CLM\text{-}S1}$ may be set as representing 0% capacity. The column life could be reported in terms of the percentage contamination remaining as an indicator independent of operating conditions.

Figure 15:
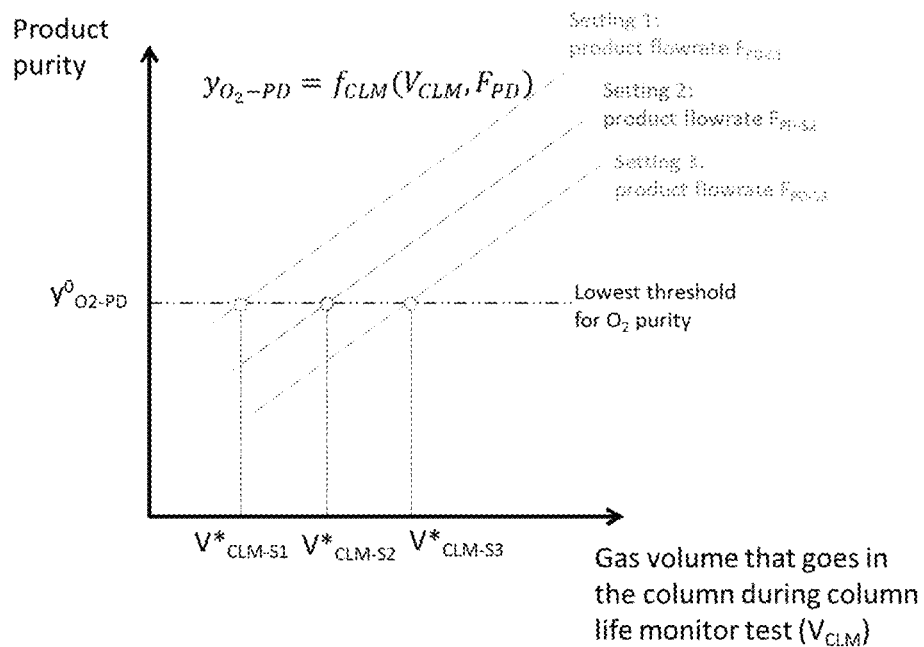
FIG. 15 illustrates correlation related to the effect of $V_{CLM}$ on product purity ($f_{CLM}$), according to the embodiments of the current disclosure.

FIG. 15 illustrates correlation related to the effect of $V_{CLM}$ on product purity ($f_{CLM}$). Specifically, pre-calibrated correlations may be set between product purity at fixed product flowrates ($F_{PD\text{-}S1}$ for setting 1, $F_{PD\text{-}S2}$ for setting 2, $F_{PD\text{-}S3}$ for setting 3) and gas volume that goes into the column during CLM test. $V_{CLM}$ corresponding to the lowest threshold product purity for settings 1, 2 and 3 are also shown. The portable ambulatory oxygen concentrator is performed at baseline conditions with fixed product flowrate such as $F_{PD\text{-}S1}$ (setting 1), $F_{PD\text{-}S2}$ (setting 2) and $F_{PD\text{-}S3}$ (setting 3). Product purity ($y_{O2\text{-}PD}$) in these tests is correlated to $V_{CLM}$ in that oxygen concentration at a fixed product flowrate decreases with $V_{CLM}$, the correlation of which is shown in FIG. 15.

A lowest threshold for product purity may be pre-determined by default setting or by user input. For example, in the case of a portable oxygen concentrator, clinicians may prescribe that the columns should be replaced once product oxygen purity drops below 70%. The corresponding $V_{CLM}$ for baseline conditions (settings 1, 2 and 3) is obtained from the curve in FIG. 15 as $V^*_{CLM\text{-}S1}$, $V^*_{CLM\text{-}S2}$ and $V^*_{CLM\text{-}S3}$. As seen in FIG. 14, these values correspond to the maximum allowable accumulated moisture concentration in adsorbent, such as zeolite, as $x^*_{m\text{-}S1}$, $X^*_{m\text{-}S2}$ and $x^*_{m\text{-}S3}$.

Figure 16:
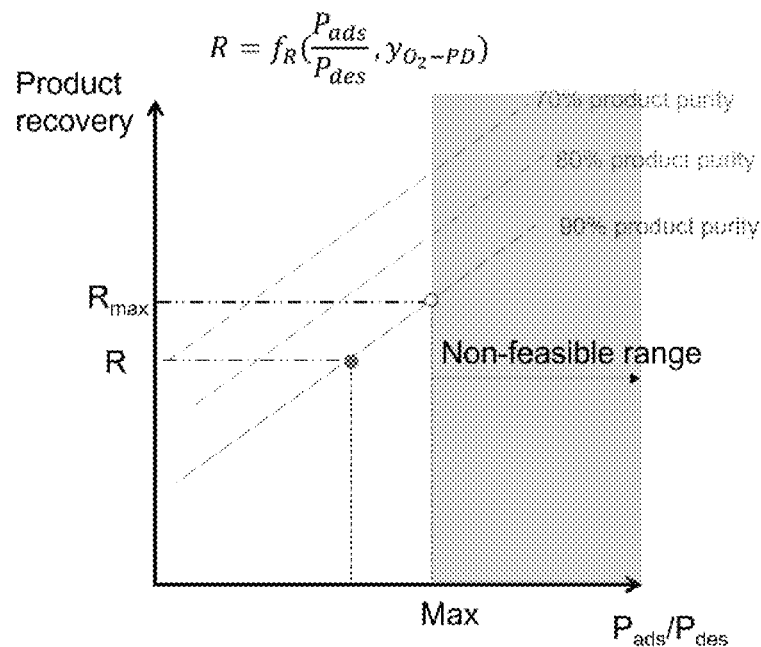
FIG. 16 illustrates the effect of pressure on product recovery ($f_R$), according to the embodiments of the current disclosure.

FIG. 16 illustrates the effect of pressure on product recovery ($f_R$) by demonstrating a pre-calibrated correlation between product recovery at a fixed oxygen concentration and the ratio of adsorption pressure over desorption pressure. The maximum recovery corresponding to the maximum pressure ratio is also shown. The process pressure is restricted by the equipment in use. For example, the maximum adsorption pressure may not exceed the pressure rating of the column/tubing/connectors, and the lowest desorption pressure needs to be within the working pressure range of the vacuum pump.

In some embodiments, the controller may be configured to determine an optimum purge volume based on a desorption pressure.

Figure 17:
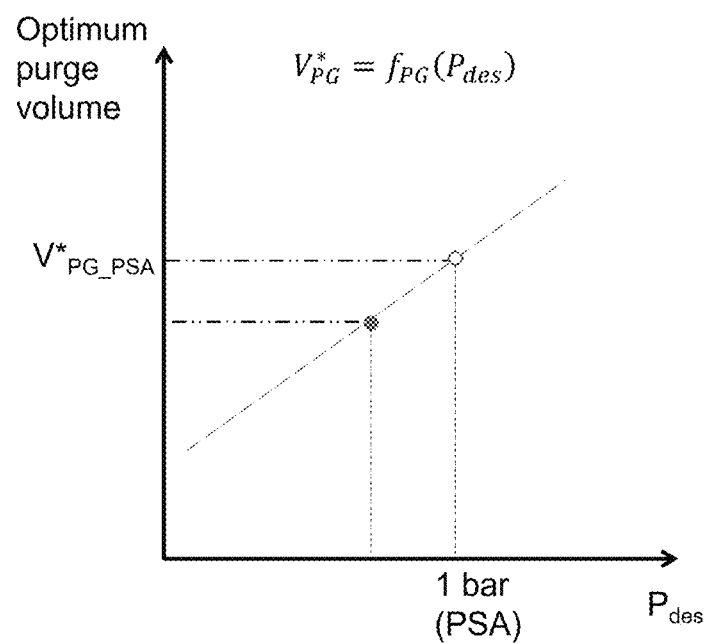
FIG. 17 illustrates the effect of desorption pressure on optimum purge volume ($f_{PG}$), according to the embodiments of the current disclosure.

FIG. 17 illustrates the effect of desorption pressure on optimum purge volume ($f_{PG}$) by showing a pre-calibrated correlation between optimum purge volume and desorption pressure. The optimum purge volume decreases as the desorption pressure is reduced. The optimum purge volume may be also dependent on the column contamination level, which is represented by $V_{CLM}$.

Flowrate calculated from differential pressure and valve $C_V$ ($f_F$)

$$F = f_F(\Delta P, C_V) \quad \text{(Eq. 1)}$$

Absolute humidity in air calculated from measured temperature and relative humidity ($f_{RH}$)

$$y_m = f_{RH}(T, RH) \quad \text{(Eq. 2)}$$

Consistent with disclosed embodiments, three functions of the automation corresponding to three sets of output parameters may be used in different contexts, which may include real-time column life monitor, automatic real-time adjustment, and automatic process design.

A Real-Time Column Life Monitor

In some embodiments, the controller may be configured to determine a remaining capacity of the at least two adsorbent columns based on a volume of feed gas going into the at least two adsorbent columns. In some embodiments, the controller may be configured to determine the estimated remaining run time of the at least two adsorbent columns based on the remaining column capacity and the operation conditions of the at least two adsorbent columns. This could also be achieved by measuring the time required for the columns to charge up to a certain pre-determined pressure. In this way in-built flow sensor may not be required. The controller is able to calculate V(CLM) using the measured charging time and the pressure pump characterisation curve (which determines the feed). Details of CLM test is described elsewhere in this disclosure.

Two indicators of a real-time column life monitor are proposed to report the remaining lifetime of the adsorbent in the column: remaining capacity and remaining run time. As shown in FIG. 14, a column working capacity may be set arbitrarily. The measured real-time volume of feed gas $V_{CLM}$ falls in between $V_{CLM\text{-}max}$ and $V_{CLM\text{-}min}$, which are the values corresponding to 0% and 100% capacity, respectively. The remaining capacity (RC) may be reported to the user as:

$$RC(\%) = \frac{V_{CLM} - V_{CLM\_min}}{V_{CLM\_max} - V_{CLM\_min}} \times 100\% \quad \text{(Eq. 5)}$$

The remaining capacity may be translated into remaining run time based on accumulated moisture concentration in the adsorbents, such as zeolite. According to FIG. 14, the measured $V_{CLM}$ indicates a corresponding moisture concentration $x_m$:

$$x_m = f_m^{-1}(V_{CLM}) \quad \text{(Eq. 6)}$$

The corresponding moisture concentration $x_m$ may be compared with $x^*_{m\text{-}s1}$, $x^*_{m\text{-}s2}$ and $x^*_{m\text{-}s3}$ to determine the remaining run time of the adsorbent in the columns before moisture concentration reaches the allowable maximum value. $x^*_{m\text{-}sN}$ (N=setting) is obtained via $V^*_{CLM}$, which comes from the following equation:

$$V^*_{CLM-sN} = f_{CLM}^{-1}(y^*_{O_2-PD(setting\ N)}, F_{PD-SN}) \quad \text{(Eq. 7)}$$

The remaining run time may then be reported in at least three ways, such as based on average operating conditions, based on real-time operating conditions, and based on the time interval between two consecutive CLM tests.

In some embodiments, the controller may be configured to determine the remaining run time further based on a measurement of one or more of a relative humidity, a temperature, a feed flowrate, and a production flowrate.

Average operating conditions includes at least but not limited to, ambient air relative humidity (RH), and temperature (T), which may be measured by humidity sensor and temperature sensor. The average ambient conditions during the previous operations may be used to calculate the average absolute humidity $\bar{y}_m$ (concentration of moisture in air) according to Eq. 2:

$$\bar{y}_m = f_{RH}(\bar{T}, \overline{RH}) \tag{Eq. 8}$$

Consistent with disclosed embodiments, the data of previous operation parameters, such as average feed flowrate ($\bar{F}_{feed}$) and the most used setting with production flowrate of $F_{PD-SN}$ (N=1, 2 or 3, or other settings) may be stored to calculate the average operating condition. The moisture concentration being accumulated in the adsorbent in time t is:

$$\Delta x_m = \bar{F}_{feed} \bar{y}_m t \tag{Eq. 9}$$

Therefore, the time before the adsorbent in the columns reaches maximum allowable moisture concentration is:

$$t_{life} = \frac{x^*_{m-SN} - x_m}{\bar{F}_{feed} \bar{y}_m} \tag{Eq. 10}$$

(N = 1 or 2 or 3 as the most commonly used setting)

In some embodiments, the remaining run time may be obtained by use of the real-time measurement.

$$t_{life} = \frac{x^*_{m-SN} - x_m}{F_{feed} y_m} \tag{Eq. 11}$$

(N = the currently used setting)

Consistent with disclosed embodiments, combining Eq. 2, Eq. 6-8 and Eq. 10-11 gives the remaining life of adsorbent in the columns as:

$$t_{life} = \frac{f_m^{-1}\left(f_{CLM}^{-1}\left(y^*_{O_2-PD(setting\ N)}, F_{PD-SN}\right)\right) - f_m^{-1}(V_{CLM})}{F_{feed} f_{RH}(T, RH)} \tag{Eq. 12}$$

In Eq. 12, $f_m$, $f_{CLM}$, $f_{RH}$ are pre-determined correlations; $y^*_{O_2-PD}$ represents the lowest oxygen purity threshold (for setting N), set by default or user input; $V_{CLM}$ is measured in the CLM test; $F_{feed}$, T, RH is the feed flowrate, ambient air temperature and relative humidity, either as average values for previous operations, or as real-time measurements.

The remaining run time may be obtained by using the time interval between two consecutive CLM tests. In some embodiments, the column is gradually contaminated at an approximately linear rate corresponding to the amount of time that has passed. The device records the time when the previous and current CLM tests are conducted. The time that has passed between these two tests are recorded as $t_{interval}$.

$$t_{life} = t_{interval} \frac{V_{CLM\_previous} - V_{CLM\_current}}{V_{CLM\_current} - V_{CLM\_min}} \tag{Eq. 13}$$

Automatic Real-Time Adjustment

The function of automatic real-time adjustment may be comprised of elements, such as the automatic adjustment of process operation, and the automatic adjustment of the product stream. Automatic real-time adjustment may be used to reduce the deviation of the device from its originally intended operating conditions caused by moisture contamination of the adsorbent columns. As a result, automatic real-time adjustment may be active constantly in the background, performing automatic adjustment whenever a CLM test is conducted and an updated $V_{CLM}$ value is supplied.

Automatic real-time adjustment is useful because columns can become increasingly contaminated by moisture, such that the adsorption capacity of the adsorbent in the column falls. Because of the contamination, a real-time adsorption pressure ($P_{ads}$) is expected to be higher than the target adsorption pressure, and a real-time desorption pressure ($P_{ads}$) is expected to be lower. For example, reduced adsorption capacity may cause column and buffer pressure to increase, which increases output flowrate and reduces output purity (because columns have no capacity to sustain a higher output rate). By adjusting the cycle time lower, target adsorption pressure can be achieved.

In some embodiments, a disclosed oxygen concentrator may not have a passive controlling facility due to the limitations on its size and weight needed to maintain it portability. Portable devices may be sensitive to small changes in operation parameters. For instance, higher $P_{ads}$ may result in the pressure pump delivering a lower feed air flowrate; the oxygen recovery may increase because of the higher adsorption pressure and lower desorption pressure; the purge volume may increase due to the larger pressure gap between two columns, which could cause waste of product gas; when oxygen tank pressure increases, the production flowrate delivered via pulse may also increase, and reduce the oxygen concentration as a result.

Changes in absorption or desorption pressure of disclosed oxygen concentrators may result in deviations from its initially intended operation parameters. In the case of moisture contamination, such deviations are largely ignored by existing oxygen concentrator devices in market. No commercial device is known to adjust the production of oxygen or other gases (or indicate the need to replace adsorbents) according to the adsorbent contamination level. The general practice is to present a generic statement to the user (e.g., "replace columns in 3-6 months"). To address this issue, real-time automatic adjustment is used in some disclosed embodiments to maintain the operation condition as closely aligned as possible with the initial design. In some embodiments, the controller may be configured to determine a real-time adsorption pressure and a real-time desorption pressure (e.g., using a feedback loop) based on the remaining capacity of the at least two adsorbent columns, and a pre-determined pressure.

In particular, the cycle time may be adjusted to maintain the desired $P_{ads}$ and $P_{des}$. There is an approximate linear correlation between the gas volume required to pressurize the column to a specific pressure and the pressure itself. As it is measured in the CLM test that $V_{CLM}$ is needed to pressurise the column to $P_{CLM}$, the volume of feed gas required in each cycle is:

$$V_{feed} = V_{CLM}\frac{P_{ads} - P_{EQ}}{P_{CLM}} = \frac{1}{2}V_{CLM}\frac{P_{ads}}{P_{CLM}} \quad \text{(Eq. 14)}$$

In Eq. 14, $P_{EQ}$ is approximately half of $P_{ads}$ due to the process configuration.

From the pressure pump characterisation (FIG. 12), there is the equation:

$$V_{feed} = \sum_0^{t_P} f_P(P)\Delta t \quad \text{(Eq. 15)}$$

In Eq. 15, $t_P$ is the phase time of pressurisation/vacuum step. At t=0, P(t)=$P_{EQ}$; at t=$t_P$, P(t)=$P_{ads}$. Combining equation 14 and 15 produces the equation:

$$P_{ads} = \frac{2P_{CLM}}{V_{CLM}}\sum_0^{t_P} f_P(P)\Delta t \quad \text{(Eq. 16)}$$

The same approach may be applied to the vacuum side to produce these equations:

$$V_{exhaust} = V_{CLM}\frac{P_{des}}{P_{CLM}} \quad \text{(Eq. 17)}$$

$$V_{exhaust} = \sum_0^{t_V} f_V(P)\Delta t \quad \text{(Eq. 18)}$$

At t=0, P(t)=0; at the end of vacuum step t=$t_V$, P(t)=$P_{des}$. Combining equation 17 and 18 produces these equations:

$$P_{des} = \frac{P_{CLM}}{V_{CLM}}\sum_0^{t_V} f_V(P)\Delta t \quad \text{(Eq. 19)}$$

The real-time adsorption pressure $P_{ads}$ and $P_{des}$ may be calculated from $V_{CLM}$ and pressurisation/vacuum step time ($t_P$ and $t_V$). Due to column contamination, $P_{ads}$ is expected to be higher than the target adsorption pressure and P des is expected to be lower. In this case, a 0.1-second interval reduction will be applied to both $t_P$ and $t_V$, followed by a recalculation of real-time $P_{ads}$ and $P_{des}$. Such process will be repeated until the predicted real-time $P_{ads}$ and $P_{des}$ are in line with the target adsorption/desorption pressures, which should be in a range (e.g., 2.5±0.1 bar and 0.5±0.05 bar) to allow some tolerance.

Figure 18:
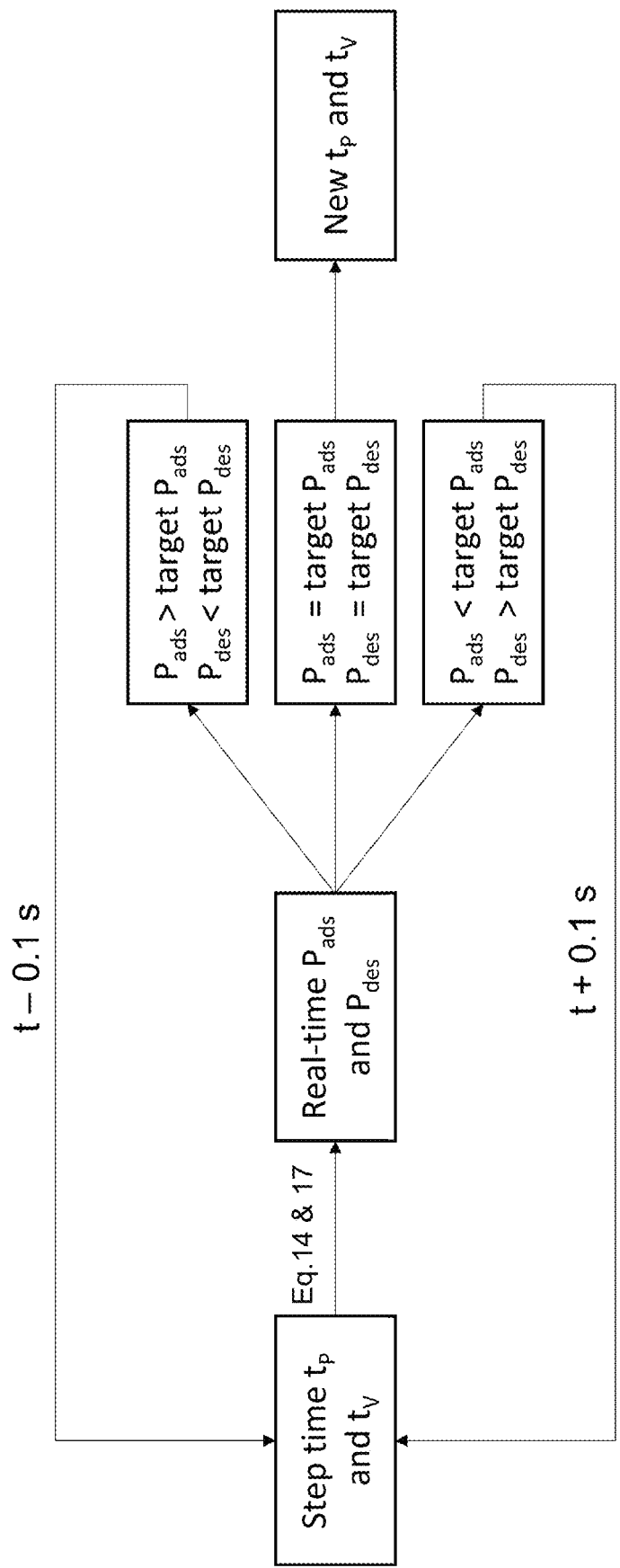
FIG. 18 depicts the iterative process of pressurisation/vacuum step time ($t_P$ and $t_V$), according to the embodiments of the current disclosure.

FIG. 18 depicts the iterative process of pressurisation/vacuum step time ($t_P$ and $t_V$). Once the pressurisation/vacuum step time is updated, the timings of the other steps may be kept the same as the designed values.

Figure 19:
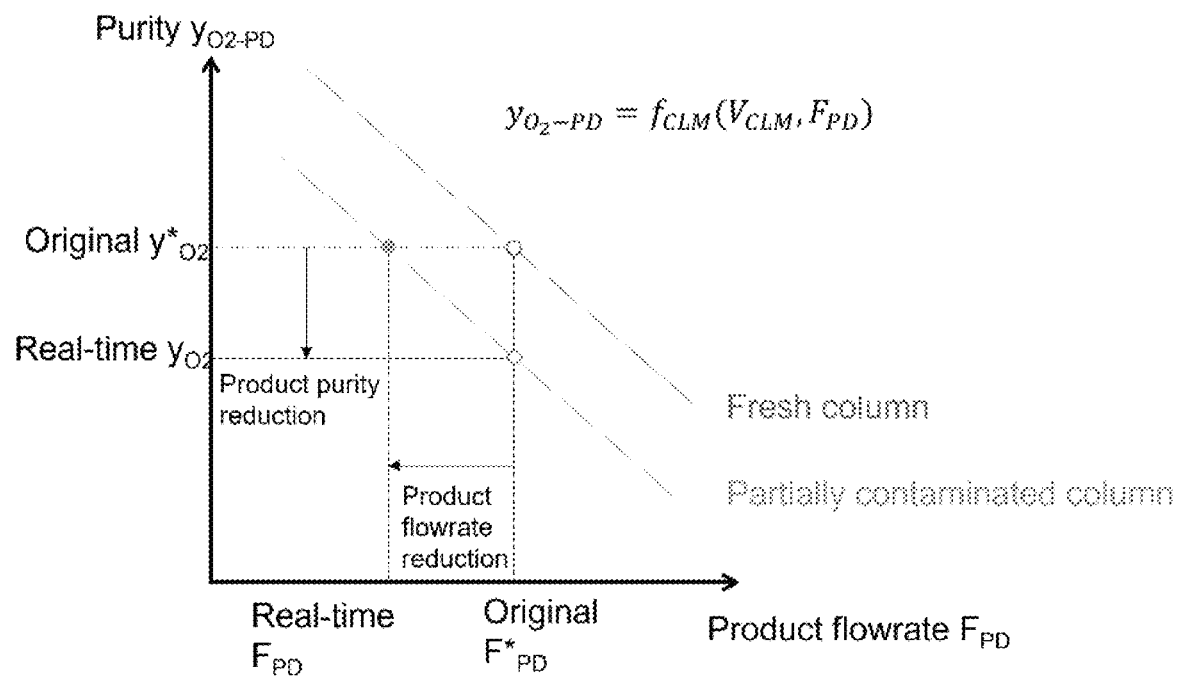
FIG. 19 illustrates a pre-calibrated correlation between product purity at fixed product flowrates and $V_{CLM}$.

As the adsorbent columns are gradually contaminated by moisture, their adsorption capacity decreases, which is reflected in the decline in output product flowrate and/or purity. In a portable ambulatory oxygen concentrator, the output product flowrate and its purity are inversely correlated. FIG. 15 may be plotted in another way to illustrate the correlation between product flowrate and purity, as shown in FIG. 19, which illustrates a pre-calibrated correlation between oxygen concentration at fixed product flowrates and $V_{CLM}$. Under a given operation condition, a higher output flowrate corresponds to a lower product purity, and vice versa. When a column undergoes contamination, the curve on FIG. 19 gradually moves downwards.

As output flowrate and oxygen concentration change, a user has the option to prioritize either flowrate or purity as the more significant parameter, which may be kept constant in the automatic adjustment to allow the other to decrease when the columns become contaminated. In this way the reduction in column capacity is reflected only in the less important parameter.

In some embodiments, if product flowrate is considered more important, it is kept constant in real-time automatic adjustment. In this case, the production valve opening time is maintained as the originally intended value. Since the adsorption pressure is adjusted to be kept the same as the design value, the output product flowrate F*PD is also kept the same. Oxygen concentration is allowed to drop when columns are contaminated, which is demonstrated in FIG. 19 by the move from the open blue datapoint to the open orange datapoint. The real-time purity is reflected in the equation:

$$y_{O_2} = f_{CLM}(F_{PD}^*, V_{CLM}) \quad \text{(Eq. 20)}$$

In some embodiments, if oxygen concentration is considered more important, the flowrate may be reduced to maintain the desired purity. In FIG. 19, the reduction is demonstrated by the move from the open blue datapoint to the close orange datapoint. The real-time product flowrate is reflected in the equation:

$$F_{PD} = f_{CLM}^{-1}(y_{O_2}^*, V_{CLM}) \quad \text{(Eq. 21)}$$

In order to obtain such flowrate, the production valve opening time $t_{pulse}$ needs to be adjusted accordingly.

$$F_{PD} = fF_{pulse}t_{pulse} = ft_{pulse}f_F(P_{ads}, C_{V-pulse}) \quad \text{(Eq. 22)}$$

In Eq. 22, f is the product delivery frequency, which may be set as default by the user or determined based on a real-time user profile (e.g., data representing a breathing pattern); and $C_{v\text{-}pulse}$ is the Cv for the production valve. Combining Eq. 21 and 22 gives the updated pulse time in the equation:

$$t_{pulse} = \frac{f_{CLM}^{-1}(y_{O_2}^*, V_{CLM})}{ff_F(P_{ads}, C_{V-pulse})} \quad \text{(Eq. 23)}$$

If the user requires continuous output flow, the production valve Cv may be adjusted to achieve the desired output flowrate under the same adsorption pressure.

Automatic Process Design

The function of automatic process design is configured to activate when a new set of user requirements is received. As a new target in production flowrate/purity is set, the process operation condition needs to be re-designed accordingly.

The control algorithm will choose the optimum adsorption pressure and desorption pressure and generate a set of cyclic sequence timings. The portable ambulatory oxygen concentrator is operated using these time sequences, while internal measurements are conducted to provide feedback to the algorithm so that the operation parameters may be fine-tuned.

In some embodiments, the automatic process design may generate the operation parameters for the highest setting from product requirements specified by the user for different settings. The automatic process design may provide lower settings by reducing the pump speed. The targets of the automatic process design may include the following in order: 1) achieve the oxygen concentration and flowrate specified by the user; 2) reduce power consumption to the maximum extent possible; 3) reduce the adsorbent contamination to the maximum extent possible.

The user may be provided the option to re-determine priority order of the above targets. Once the automatic process design is completed, the user may have the option to manually specify a particular operation parameter and override the algorithm-generated setting. However, the purpose of the portable ambulatory oxygen concentrator automation is to eliminate the time and cost for the user to choose and set up each operation parameter. Thus, while a user override may be provided, it is not expected to be a routine step in the automation process.

While not required, automatic portable ambulatory oxygen concentrator design is developed from the following test findings on disclosed portable ambulatory oxygen concentrators: 1) The optimum step sequence is generally similar in various portable ambulatory oxygen concentrators. Therefore, it is proposed that the step sequence remains the same in automatic process design. The operation parameters generated by the algorithm will mainly be the time of each step in the cyclic operation. 2) Pressurisation/vacuum time may be calculated according to the given adsorption pressure ($P_{ads}$) and desorption pressure ($P_{des}$), consistent with disclosed embodiments. 3) Optimum purge volume is dependent on the desorption pressure ($P_{des}$) and may be achieved via different combinations of purge flowrate and purge time. Effect of purge is irrelevant to flowrate or time as a single parameter. 4) Optimum equalisation time is dependent on the gap between adsorption pressure ($P_{ads}$) and desorption pressure ($P_{des}$). In most cases, 0.3-0.5 second is sufficient, and the effect of equalisation time is limited within this range. 5) The higher $P_{ads}$ results in higher oxygen tank's pressure (Pot). In consequence, the pulse flowrate, which is controlled by differential pressure of oxygen tank and ambient, also increases.

The automatic portable ambulatory oxygen concentrator design starts from the user requirements on product flowrate ($F_{PD}$) and purity ($y_{O2-PD}$). Based on a pre-determined correlation between the ratio of adsorption pressure to adsorption pressure and product recovery (FIG. 16), a maximum recovery rate ($R_{max}$) may be identified according to the maximum $P_{ads}/P_{des}$ that the process may sustain mechanically, and the user requirement for product purity.

Assuming that the highest adsorption pressure ($P^0_{ads}$) and lowest desorption pressure ($P^0_{des}$) are to be used in the process, the feed flowrate that may be delivered at $P^0_{ads}$ and the corresponding $P^0_{EQ}$ are calculated from the pressure pump characteristics (FIG. 12) as measured by these equations:

$$F_{P_{ads}} = f_P(P_{ads}) \tag{Eq. 24}$$

$$F_{P_{EQ}} = f_P(P_{EQ}) = \sim f_P\left(\frac{1}{2}P_{ads}\right) \tag{Eq. 25}$$

The average feed air flowrate may be estimated as the average of $F_{ads}$ and $F_{EQ}$ as measured by this equation:

$$F_{avg} = \frac{1}{2}\left(F_{P_{ads}} + F_{P_{EQ}}\right) \tag{Eq. 26}$$

Maximum product flowrate at the desired oxygen concentration is measured by this equation:

$$F_{PD} = \frac{y_{O_2-feed}}{y_{O_2-PD}} F_{ave} R_{max} \tag{Eq. 27}$$

If the calculated $F_{PD}$ in Eq. 27 is less than the user requirement of product flowrate, $P_{ads}$ will be reduced by 0.05 bar and $P_{des}$ will be increased by 0.05 bar before Eqs. 24-27 are recalculated. The process will be repeated until the calculated $F_{PD}$ is higher than or equal to the required value.

In some embodiments, the controller may be configured to determine a pressurization step time and a vacuum step time based on the real-time adsorption pressure and the real-time desorption pressure.

Figure 20:
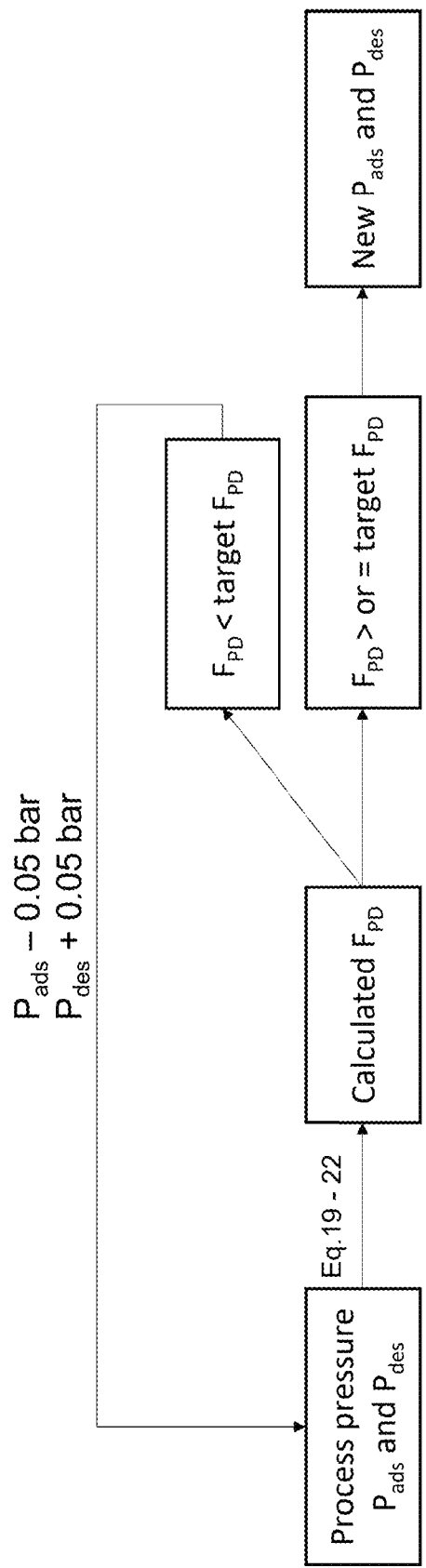
FIG. 20 depicts the iterative process of adsorption pressure ($P_{ads}$) and desorption pressure ($P_{des}$), according to the embodiments of the current disclosure.
Figure 21:
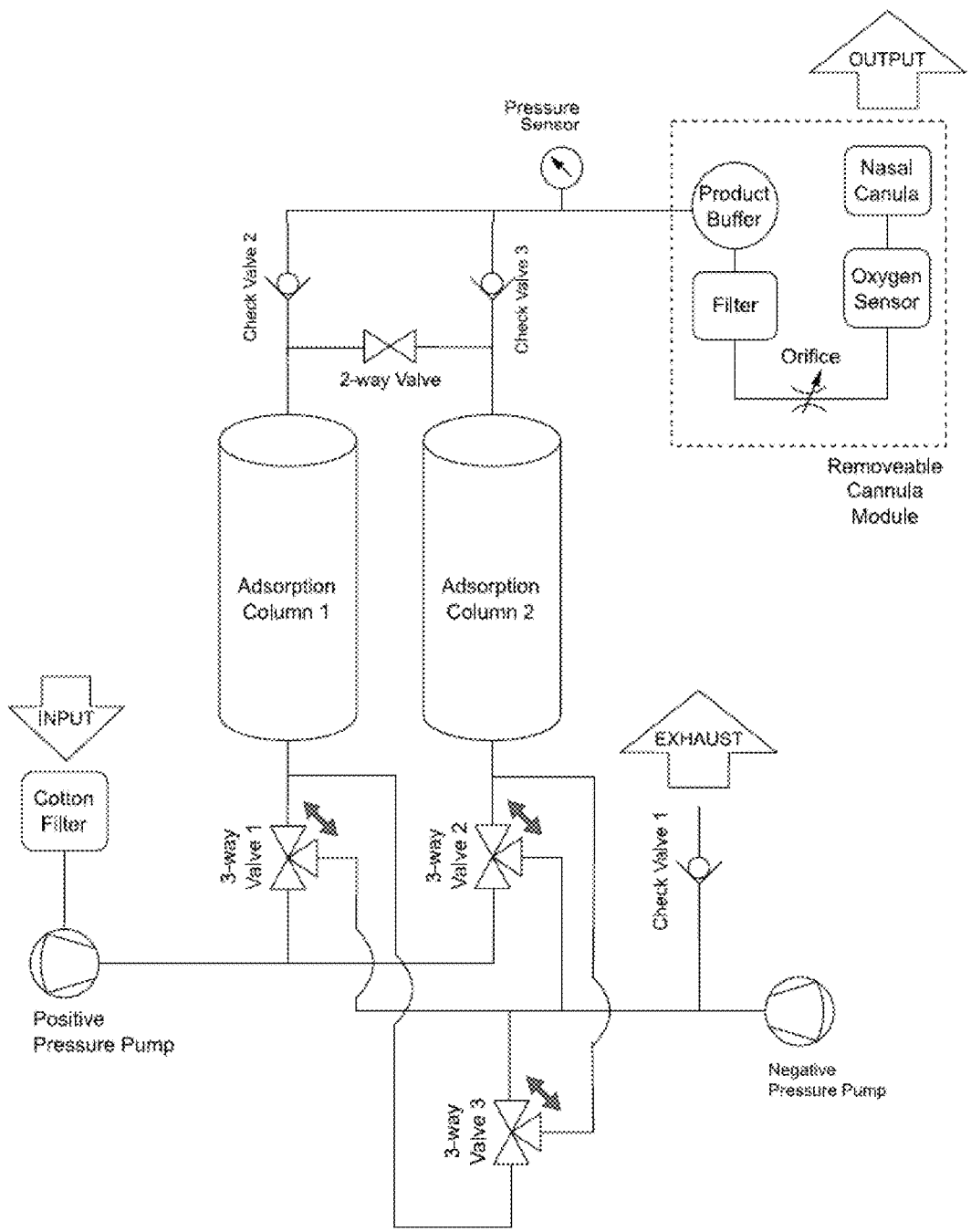
FIGS. 21 and 22 depict schematic diagrams of other exemplary disclosed oxygen concentrators of the current disclosure.
Figure 22:
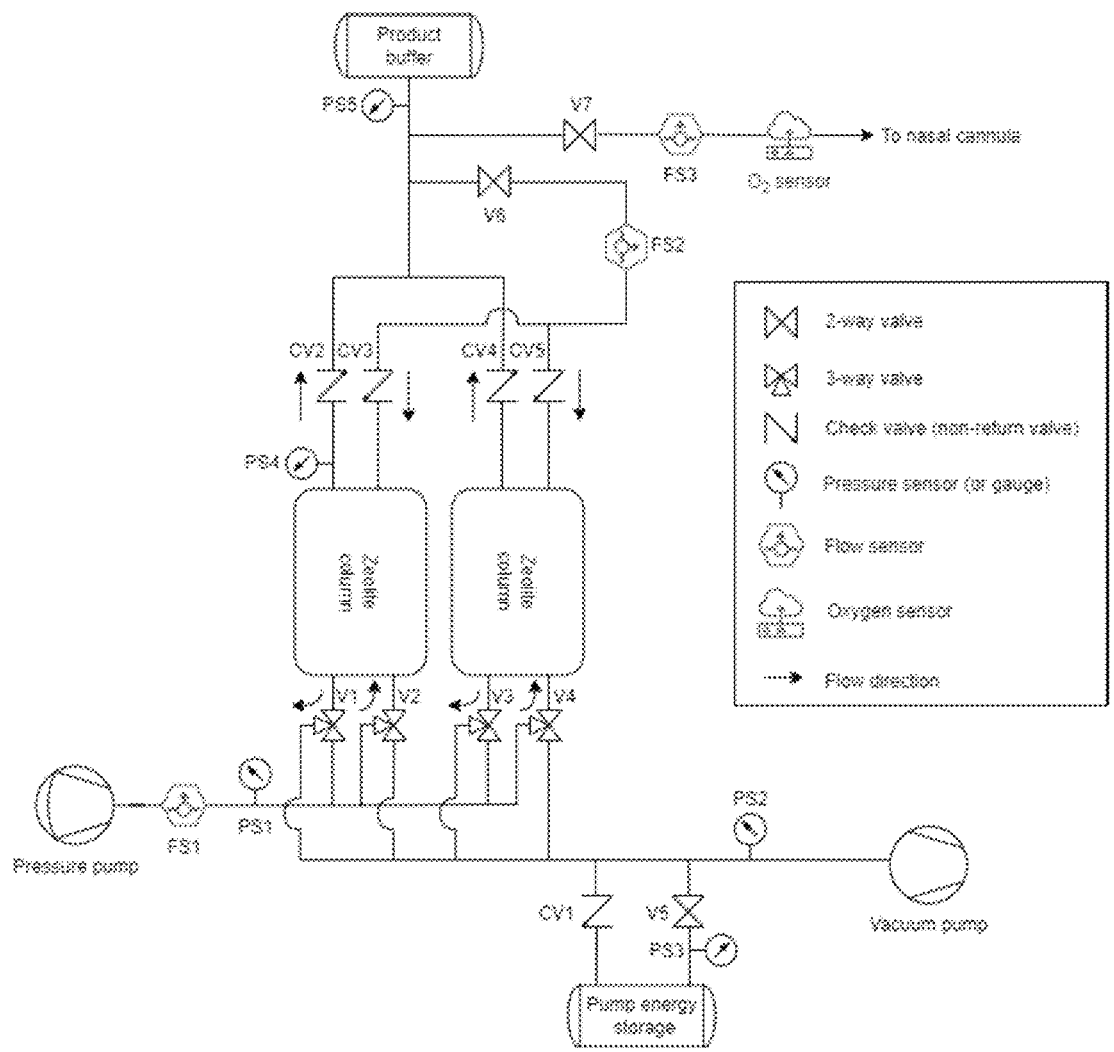

FIG. 20 depicts the iterative process of adsorption pressure ($P_{ads}$) and desorption pressure ($P_{des}$). Once $P_{ads}$ and $P_{des}$ are chosen, the following cyclic sequence is generated: 1) calculating pressurisation step time $t_P$ and vacuum step time $t_V$ as discussed above in the Eqs. 16 and 19; 2) calculating purge step time $t_{PG}$. 3) setting Equalisation time $t_{EQ}$; and 4) calculating pulse production time $t_{pulse}$.

Purge step time $t_{PG}$ may be obtained by the following steps. Optimum purge volume is found based on a pre-determined correlation as shown in FIG. 18, using the equation:

$$V^*_{PG} = f_{PG}(P_{des}) \tag{Eq. 28}$$

Purge flowrate may be calculated according to the differential pressure and the control valve or orifice size using Eq. 1 and the equation:

$$F_{PG} = f_F((P_{ads} - P_{des}), C_{v-PG}) \tag{Eq. 29}$$

In Eq. 29, $C_{v-PG}$ is the purge valve/orifice characteristic. Combining Eqs. 28 and 29 gives the purge step time using the equation:

$$t_{PG} = \frac{V^*_{PG}}{F_{PG}} = \frac{f_{PG}(P_{des})}{f_F((P_{ads} - P_{des}), C_v)} \tag{Eq. 30}$$

Equalisation time $t_{EQ}$ may be set as 0.4 second as the effect of $t_{EQ}$ is limited when in the range of 0.3-0.5 second.

The pulse flowrate may be calculated via Eq. 1 using pulse valve/orifice characteristic. Same as Eq. 22, and using the equation:

$$F_{pulse} = f_F(P_{ads}, C_{v-pulse}) \quad \text{(Eq. 31)}$$

The pulse time is calculated via the equation:

$$t_{pulse} = \frac{F_{PD}}{fF_{pulse}} = \frac{F_{PD}}{ff_F(P_{ads}, C_{v-pulse})} \quad \text{(Eq. 32)}$$

If the user requires continuous output, the production valve Cv may be adjusted to achieve the desired output flowrate.

After the time for each sequence step is generated, the process runs accordingly for 10-20 cycles and the adsorption pressure, desorption pressure, product flowrate and purity are measured. Apart from the pulse time $t_{pulse}$, the time for other steps is fine-tuned at 0.1 second intervals until the measured parameters fall in the desired range. The pulse time $t_{pulse}$ may be adjusted at 0.01 second interval until the desired product flowrate and purity are achieved.

Feedback

Two categories of feedback may be included in a closed-loop control system. The controller is configured to include the closed-loop control system based on an adsorbent column contamination level obtained from the periodic column life monitor (CLM) test, and the continuous sensor data of one or more of an oxygen concentration, a production flowrate, a temperature, an adsorption pressure and a desorption pressure.

The CLM test may be configured to provide real-time information on the adsorbent column contamination level, which forms the basis of real-time control of the portable ambulatory oxygen concentrator and the oxygen output. The CLM test should be performed periodically, for example, once per week, every time the device is turned on, or every time the first input data is received. It is worth noting that unlike sensor data, the CLM result may not be acquired during the operation of the portable ambulatory oxygen concentrator. This may be attributed to the requirement of the pressure pump and the adsorbent columns for conducting the CLM test, rendering them unavailable for simultaneous use in process operation.

In a CLM test, the two columns are pressurised in turn with feed gas from the ambient environment to a predetermined pressure ($P_{CLM}$) while the column product end is closed. An in-line pressure sensor measures the column pressure and sends a signal to the control board to stop the pump when pressure reaches $P_{CLM}$. An internal timer measures the time it takes for the test to be completed ($t_{CLM}$).

The volume of feed gas going into the column during CLM ($V_{CLM}$) may be obtained from either:

1) an in-line flow sensor; or $$V_{CLM} = \sum_0^{t_{CLM}} F(t)\Delta t \quad \text{(Eq. 3)}$$

2) a calculation based on the pressure pump characteristic curve as shown in FIG. 12. At any given time during CLM, the flowrate delivered by the pressure pump may be determined from the measured column pressure.

$$V_{CLM} = \sum_0^{t_{CLM}} f_P(P)\Delta t \quad \text{(Eq. 4)}$$

Continuous sensor data may be a category of feedback in a closed-loop control system. The control algorithm may generate output parameters that operate the portable ambulatory oxygen concentrator. In-built sensors may take real-time measurements of process variables, which may be supplied to the control algorithm as feedback information to allow the fine-tuning of output parameters. The sensor data from the portable ambulatory oxygen concentrator may include, but is not limited to, oxygen concentration (product purity), a product gas stream flowrate, a process pressure at various positions in the portable ambulatory oxygen concentrator such as the feed end and product end of the columns, and a process temperature at various positions in the portable ambulatory oxygen concentrator such as data from a thermocouple incorporated inside the adsorbent column to gauge local adsorbent temperature.

Valve and Pump Control

Consistent with disclosed embodiments, the control algorithm outputs a set of operation parameters, including adsorption pressure, desorption pressure, cycle time, step time, optimum purge (volume, time, flowrate), product delivery (flowrate, frequency), pump capacity (e.g., running at 50% of full capacity), etc. The operation of the portable ambulatory oxygen concentrator, which includes controlling of pump operation, vacuum operation, switching of a plurality of valves open or close, using the set of operation parameters determined by the control algorithm, may be converted into a set of instructions for controlling each valve and each pump in the portable ambulatory oxygen concentrator. As an example, the instructions may look like this:

|  | On time | Degree of valve opening/pump capacity |
|---|---|---|
| Valve 1 | 1.0 second | 50% |
| Valve 2 | 2.0 seconds | 100% |
| ... | ... | ... |
| Pump 1 | Always on | 80% |
| Pump 2 | 5.0 seconds | 100% |
| ... | ... | ... |

The portable ambulatory oxygen concentrator may operate following the set of instructions. The in-built sensors then collect a plurality of real-time measurements of the portable ambulatory oxygen concentrator as feedback information, as discussed herein.

Some embodiments of oxygen concentrators may include a single pressure sensor while other embodiments may include multiple pressure sensors. For example, a single pressure sensor may be incorporated in the buffer tank (e.g., oxygen storage tank 130), and this single pressure sensor may monitor the pressure of both columns 110, 120 and cut-off or stop pressurization when the adsorption pressure in a column is reached. Alternatively, a single vacuum pressure sensor may be incorporated in the vacuum line where it monitors the desorption pressure of both columns 110, 120 and cut-off or stop pressurisation/vacuum when the target desorption pressure in a column is reached. However, a single pressure sensor may not pick up the vacuum pressure of both columns in some embodiments; a single vacuum pressure sensor may not pick up the positive pressure of both columns in some embodiments. Thus, in some embodiments, a single pressure sensor configuration may not be able to determine when the columns reach adsorption or desorption pressure fully. In some embodiments, for more accurate monitoring, the device may include multiple pressure sensors. For example, in a two-column device (as illustrated in FIG. 1), the device may include two pressure sensors to measure the pressure of both columns individually. Since the two pressure sensors can detect the absolute pressure of the two columns, they will also detect both the adsorption and the desorption pressure of the columns (which indicates how "clean" the columns are at the end of desorption process).

When pressurization gets terminated when adsorption pressure is achieved in a column, there is a possibility that the adsorbent in both columns have different life (contamination) states to start off with. A dynamic sequence timing, which allows the two columns to operate with different cycle time, is considered the best approach to handle the imbalance between the two columns. In the setting of dynamic timing, the cycle time is adjusted according to the column that is undergoing adsorption phase; which means the cycle time is longer when the relatively less contaminated column undergoes adsorption, and the cycle time is shorter when the relatively more contaminated column undergoes adsorption. When pressurizing a column with adsorbent that is more contaminated, adsorption pressure may be achieved quicker with a shorter cycle time. In other words, the column with less contaminated adsorbent may not have enough time relatively to reach target desorption pressure. This means that the "better" column does not get the full pressure swing, thereby reducing recovery. As a result, purity of oxygen may decrease during production from the column with less contaminated adsorbent. However less feed air may be required to reach back to adsorption pressure from a weaker desorption pressure, plus longer cycle time due to more $N_2$ capacity, so it may slow down the contamination/aging effects on this column with less contaminated adsorbent. When pressurizing this column, the column with more contaminated adsorbent may get more than enough time to reach desorption pressure, and therefore may start off "fresher." In some cases, it may need more feed air thus advances aging. In some cases, a more sub-atmospheric state may "reverse" aging too. Fresher adsorbent like zeolites, with its increased pressure swing range (from its lower desorption pressure), may give better recovery thus better output purity.

Including a single sensor or multiple decoupled sensors in each column 110, 120 also enables the device to run different sets of parameters in each column, such as with dynamic sequence timing. In other words, the columns 110, 120 do not need to run the same set of parameters or on the same timing. Instead, they can run mismatched timing to achieve maximum output. The benefit of running different sets of parameters on the different columns is that the columns can be run at different life stages—as in one column may be more contaminated (by water) than the other to achieve maximum output and maximizing column lifetime.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware, but systems and methods consistent with the current disclosure may be implemented with hardware and software. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), and adaptations or alterations based on the current disclosure. The elements in the claims are to be interpreted broadly based on the language employed in the claims and not limited to examples described in the current specification or during the prosecution of the application, which examples are to be construed as nonexclusive. Further, the steps of the disclosed methods may be modified in any manner, including reordering steps or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Further, since numerous modifications and variations will readily occur from studying the current disclosure, it is not desired to limit the disclosure to the exact construction and operation illustrated and described, and accordingly, all suitable modifications and equivalents may be resorted to, falling within the scope of the disclosure.

As used herein, unless specifically stated otherwise, the term "or" encompasses all possible combinations, except where infeasible. For example, if it is stated that a component may include A or B, then, unless specifically stated otherwise or infeasible, the component may include A, or B, or A and B. As a second example, if it is stated that a component may include A, B, or C, then, unless specifically stated otherwise or infeasible, the component may include A, or B, or C, or A and B, or A and C, or B and C, or A and B and C.

It should be emphasized that the description above is only exemplary, and many variations and modifications are possible. For example, in some embodiments, the output of multiple (2, 3, 4, 5, etc.) disclosed oxygen concentrators may be fluidly coupled together for scaling up the produced product gas. In some embodiments, a 'T-shaped' connector may be used to daisy chain the multiple oxygen concentrators together and deliver the combined product gas, e.g., to a user or to a storage tank. In some embodiments, the multiple oxygen concentrators may be incorporated with battery cradle and sensor/software which is configured to detect the connection and sync the connecting devices. In some such embodiments, the multiple oxygen concentrators may be connected to a battery cradle and wheeled on a trolley to allow flexible scale up.

In some disclosed oxygen concentrators, purge and equalisation may be performed upstream of the buffer, for example, to prevent unnecessary fluctuation of the product flowrate.

In some embodiments, the columns may be reset when the device is turned off. For example, prior to turning off the disclosed oxygen concentrator, sufficient time may be provided to allow the vacuum pump to reduce the pressure of both the columns to the maximum extent (e.g., 0.3 bar), and then the system may be turned off to allow for full desorption.

In some embodiments, a bio-compatible filter material (e.g., an off-the-shelf biocompatible filter material) may be used in the zeolite columns.

In some embodiments, the cycle time of the disclosed oxygen concentrator may be tuned to match the user's breathing profile. For example, the cycle time may be automatically adjusted to match user's breathing profile (either detected by breathing sensor or pre-loaded by clinician for the particular disease type) so that the peak of production flow coincides with the user breathing in. In such an approach, a smaller volume product storage tank may be used.

In some embodiments, the zeolite columns may be cycled with hot air to dry out the zeolites and maximise output and column life.

In some embodiments, the disclosed oxygen concentrator may include a water removal desiccant column which may be housed in a secondary column. This secondary column may be rejuvenated separately, either by introducing, for example, hot air to dry the desiccant or may be removed from the oxygen concentrator or rejuvenation/servicing.

In some embodiments, the disclosed oxygen generators may be provided with a flight/high altitude mode. For example, barometric pressure sensors may make corrections to oxygen output to compensate for cabin pressure or lower $FiO_2$ at high altitudes. In some embodiments, the barometric pressure sensors may be incorporated in the device. In some embodiments, the disclosed oxygen concentrators may be equipped with a transceiver and may be configured to wirelessly send and receive data (e.g., send operating parameters and performance metrics to an external controller, receive instructions to vary operating parameters, etc.). In some such embodiments, the barometric pressure sensor may be an external sensor (e.g., wirelessly sending signals to the oxygen concentrator).

In some embodiments, the disclosed oxygen generator may be attached or integrated with a high-flow (e.g., flow range 2-60 L/min) nasal therapy device, such as a humidifier with an integrated flow generator which delivers high-flow, warmed and humidified respiratory gases to spontaneously breathing patients. The addition of the disclosed oxygen concentrator provides a portable device that instantaneously produces oxygen and provides portability, versatility, and continuity of care.

In some embodiments, the disclosed oxygen concentrator may be configured as a sport training device. For example, the disclosed oxygen concentrator may be configured as a sports training aid to create a hypoxic $FiO_2$ 15% environment and simulate high altitude training. oxygen separated from the air stream from the adsorption process may be discarded and the adsorbed $N_2$ released to the user ($N_2$-concentrated gas). In some embodiments, such a device may be configured as a bedside device (e.g., larger device) with an increased focus on operating quieter (e.g., to not disturb sleep) and may use larger columns.

In some embodiments, 3D printed lattice structures may be used as dampeners to reduce vibration. Reducing vibration may contribute to reducing sound of the overall device. For example, 3D printed rubber arranged in a lattice structure (e.g., in an open Kelvin Cell pattern) may be used to absorb and dissipate mechanical energy and thereby damp mechanical vibrations produced by the oxygen concentrator. The use of a Kelvin cell lattice structure may have the advantages of storing energy with its elastic deformation and may return to its original shape quickly, like a spring, when force is removed. Such a design may be customizable where the 3D printed structure may be formed around the pump and act as both a dampener and also as a structure to hold it in situ, keeping the pump suspended thereby further reducing vibrations. In some embodiments, the 3D printed lattice structures may be configured such that it can channel cooling air flow more efficiently to cool down the pumps.

In some embodiments, the disclosed oxygen concentrators may include a customised power pack that may be incorporated into the device, e.g., by replacing the back cover.

In some embodiments, a replaceable module within the disclosed oxygen concentrator may be used to switch from continuous to automated titration mode. For example, a replaceable module, sitting under the cannula exit port, that can be replaced with a 'smart' module that contains oxygen sensors and 2-way valves to activate automated titrations and replaceable filters. Such a module may allow the device to switch from a continuous device to a pulse-dose device with the ability to detect breath, adjust oxygen flow and titrate.

Other embodiments will be apparent from consideration of the specification and practice of the embodiments disclosed herein. It is intended that the specification and examples be considered as example only, with a true scope and spirit of the disclosed embodiments being indicated by the following claims.

The invention claimed is:

1. A portable oxygen concentrator, comprising:
    a first column and a second column, wherein the first column and the second column include an adsorbent;
    one or more pumps;
    a product buffer;
    a plurality of valves fluidly coupling the first column, the second column, the one or more pumps, and the product buffer; and
    a controller configured to cycle repeatedly through:
        (a) raising pressure in the first column by connecting the first column to a positive pressure pump and releasing concentrated oxygen in the first column to the product buffer,
        (b) equalizing the pressure in the first column and the second column by connecting the first column to the second column,
        (c) lowering the pressure in the first column by connecting the first column to a negative pressure pump, and
        (d) equalizing the pressure in the first column and the second column by connecting the first column to the second column,
    wherein the product buffer is contained in a removable module, the removable module further comprising a filter, an inflatable oxygen reservoir, and a check valve.

2. The portable oxygen concentrator of claim 1, wherein the controller is further configured to lower pressure in the second column by connecting the second column to the negative pressure pump when raising the pressure in the first column.

3. The portable oxygen concentrator of claim 1, wherein the controller is further configured to raise the pressure in the second column by connecting the second column to the positive pressure pump and release the concentrated oxygen to the product buffer, when lowering the pressure in the first column.

4. The portable oxygen concentrator of claim 1, wherein the product buffer is configured to be filled with an adsorbent to increase storage capacity of the product buffer, to enhance the purity of oxygen, or to stabilize a flow rate of the concentrated oxygen.

5. The portable oxygen concentrator of claim 1, wherein the inflatable oxygen reservoir is an inflatable balloon.

6. The portable oxygen concentrator of claim 1, wherein the inflatable oxygen reservoir is stretchable from a single circular spot on a flow path tube.

7. The portable oxygen concentrator of claim 1, wherein the check valve is a one-way duck bill valve that is configured to inflate the inflatable oxygen reservoir.

8. The portable oxygen concentrator of claim 1, wherein the check valve requires a cracking pressure before allowing air to pass the check valve.

9. The portable oxygen concentrator of claim 7, wherein the check valve is located at a distal point along the flow path tube without covering a filling aperture of the inflatable oxygen reservoir.

10. The portable oxygen concentrator of claim 1, wherein the positive pressure pump and the negative pressure pump is on a single dual-head pump.

11. A method for operating a portable oxygen concentrator, performed by a controller, wherein the portable oxygen concentrator comprises one or more pumps and a plurality of valves fluidly coupling a first column that includes an adsorbent, a second column that includes an adsorbent, and a product buffer, the method comprising cycling repeatedly through:
(a) raising pressure in the first column to by connecting the first column to a positive pressure pump and releasing concentrated oxygen in the first column to the product buffer,
(b) equalizing the pressure in the first column and the second column by connecting the first column to the second column,
(c) lowering the pressure in the first column by connecting the first column to a negative pressure pump, and
(d) equalizing the pressure in the first column and the second column by connecting the first column to the second column,
wherein the product buffer is contained in a removable module, the removable module also comprising a filter, an inflatable oxygen reservoir, and a check valve.

12. The method for operating a portable oxygen concentrator of claim 11, wherein the controller is further configured to lower pressure in the second column by connecting the second column to the negative pressure pump when raising pressure in the first column.

13. The method of operating a portable oxygen concentrator of claim 11, wherein the controller is further configured to raise the pressure in the second column by connecting the second column to the positive pressure pump and release the concentrated oxygen to the product buffer when lowering the pressure in the first column.

14. The method of operating a portable oxygen concentrator of claim 11, wherein the product buffer is configured to be filled with an adsorbent to increase storage capacity of the product buffer, to enhance purity of oxygen or to stabilize a flow rate of the concentrated oxygen.

15. The method of operating a portable oxygen concentrator of claim 11, wherein the inflatable oxygen reservoir is an inflatable balloon.

16. The method of operating a portable oxygen concentrator of claim 15, wherein the inflatable oxygen reservoir is stretchable from a single circular spot on a flow path tube.

17. The method of operating a portable oxygen concentrator of claim 11, wherein the check valve is a one-way duck bill valve configured to inflate the inflatable oxygen reservoir.

18. The method of operating a portable oxygen concentrator of claim 11, wherein the check valve requires a cracking pressure before allowing air to pass the check valve.

19. The method of operating a portable oxygen concentrator of claim 11, wherein the check valve is located at a distal point along the flow path tube without covering a filling aperture of the inflatable oxygen reservoir.

20. The method for operating a portable oxygen concentrator of claim 11, wherein the positive pressure pump and the negative pressure pump are on a single dual-head pump.

21. A portable oxygen concentrator, comprising:
a first column and a second column, wherein the first column and the second column include an adsorbent;
one or more pumps;
a plurality of valves fluidly coupling the first column, the second column, and the one or more pumps; and
a removable module, comprising
a product buffer filled with adsorbent,
an inflatable oxygen reservoir, and
a duck-bill valve with cracking pressure that is configured to inflate the inflatable oxygen reservoir.

22. The portable oxygen concentrator of claim 21, wherein the inflatable oxygen reservoir is an inflatable balloon.

23. The portable oxygen concentrator of claim 22, wherein the inflatable oxygen reservoir is stretchable from a single circular spot on a flow path tube.

24. The portable oxygen concentrator of claim 21, wherein the duck-bill valve requires the cracking pressure before allowing air to pass the duck-bill valve.

25. The portable oxygen concentrator of claim 21, wherein the duck-bill valve is located at a distal point along the flow path tube without covering a filling aperture of the inflatable oxygen reservoir.

26. The portable oxygen concentrator of claim 22, wherein the flow path tube has a reduced inner diameter around an opening of the inflatable oxygen reservoir.

27. The portable oxygen concentrator of claim 21, wherein the portable oxygen concentrator includes a pressure sensor next to the removable module, a high pressure change rate detected by the pressure sensor indicates a replacement timing of the removable module.

* * * * *